US011134950B2

(12) United States Patent
Blatter et al.

(10) Patent No.: US 11,134,950 B2
(45) Date of Patent: *Oct. 5, 2021

(54) METHODS OF ATTACHING AN IMPLANT TO A VESSEL

(71) Applicant: Advent Access Pte. Ltd., Singapore (SG)

(72) Inventors: Duane D. Blatter, Salt Lake, UT (US); Trent J. Perry, Kaysville, UT (US); Nathaniel P. Young, Salt Lake City, UT (US); Jeffrey E. Ransden, Fairfield, CT (US)

(73) Assignee: Advent Access Pte. Ltd., Singapore (SG)

( * ) Notice: Subject to any disclaimer, the term of this patent is extended or adjusted under 35 U.S.C. 154(b) by 363 days.

This patent is subject to a terminal disclaimer.

(21) Appl. No.: 16/352,693

(22) Filed: Mar. 13, 2019

(65) Prior Publication Data

US 2019/0274686 A1  Sep. 12, 2019

Related U.S. Application Data

(63) Continuation of application No. 14/720,969, filed on May 25, 2015, now abandoned, which is a
(Continued)

(51) Int. Cl.
*A61B 17/11* (2006.01)
*A61M 39/02* (2006.01)
(Continued)

(52) U.S. Cl.
CPC ............ *A61B 17/11* (2013.01); *A61B 17/115* (2013.01); *A61M 39/02* (2013.01);
(Continued)

(58) Field of Classification Search
CPC .................. A61B 17/11; A61B 17/115; A61B 2017/1107; A61B 17/0218; A61B 2017/1135; A61M 39/02; A61M 39/0247
See application file for complete search history.

(56) References Cited

U.S. PATENT DOCUMENTS 484,681 A   10/1892  Smith
544,148 A    8/1895  Welter
(Continued)

FOREIGN PATENT DOCUMENTS

CN         1213319      4/1999
DE    102008034364 A1   2/2009
(Continued)

OTHER PUBLICATIONS

Brunette et al., "Titanium in Medicine: Material Science, Surface Science, Engineering, Biological Responses and Medical Applications," Berlin; Springer, 2001, ISBN 3-540-66936-1, p. 727.
(Continued)

*Primary Examiner* — George J Ulsh
*Assistant Examiner* — Rachel S Highland
(74) *Attorney, Agent, or Firm* — Cesari & McKenna, LLP

(57) ABSTRACT

A method of attaching an implant to a vessel can include clamping a portion of a wall of a vessel within a patient. The method can also include positioning an implant adjacent to an outer surface of the wall of the vessel, and the implant can include an access port. The method can also include cutting the wall of the vessel about the portion of the wall that has been clamped, passing the portion of the wall that has been clamped and that has been cut about through the implant to remove the portion of the wall from the patient and to provide an opening in the vessel, and securing the implant
(Continued)

to the vessel such that the access port is in direct fluid communication with an interior of the vessel via the opening in the vessel.

10 Claims, 47 Drawing Sheets

Related U.S. Application Data continuation of application No. 14/181,401, filed on Feb. 14, 2014, now Pat. No. 9,039,717, which is a continuation of application No. 13/781,575, filed on Feb. 28, 2013, now Pat. No. 8,668,706, which is a continuation of application No. 12/480,678, filed on Jun. 8, 2009, now Pat. No. 8,409,228.

(60) Provisional application No. 61/059,590, filed on Jun. 6, 2008.

(51) Int. Cl.
   *A61B 17/115* (2006.01)
   *A61B 17/02* (2006.01)

(52) U.S. Cl.
   CPC ..... *A61M 39/0247* (2013.01); *A61B 17/0218* (2013.01); *A61B 2017/1107* (2013.01); *A61B 2017/1135* (2013.01)

(56) References Cited

U.S. PATENT DOCUMENTS

| | | |
|---|---|---|
| 669,586 A | 3/1901 | Levasseur |
| 2,828,744 A | 4/1958 | Hirsch |
| 3,094,122 A | 6/1963 | Gauthier |
| 3,782,381 A | 1/1974 | Winnie |
| 3,998,222 A | 12/1976 | Shihata |
| 4,013,080 A | 3/1977 | Froning |
| 4,164,221 A | 8/1979 | Bentley |
| 4,183,357 A | 1/1980 | Bentley |
| 4,318,401 A | 3/1982 | Zimmerman |
| 4,405,319 A | 9/1983 | Cosentino |
| 4,423,730 A | 1/1984 | Gabbay |
| 4,484,912 A | 11/1984 | Raible |
| RE31,855 E | 3/1985 | Osborne |
| 4,559,033 A | 12/1985 | Stephen |
| 4,667,673 A | 5/1987 | Li |
| 4,781,695 A | 11/1988 | Dalton |
| 4,822,341 A | 4/1989 | Colone |
| 4,846,799 A | 7/1989 | Tanaka |
| 4,878,904 A | 11/1989 | Callaway |
| 4,906,236 A | 3/1990 | Alberts |
| 4,973,317 A | 11/1990 | Bobrove |
| 5,092,849 A | 3/1992 | Sampson |
| 5,127,412 A | 7/1992 | Cosmetto |
| 5,222,963 A | 6/1993 | Brinkerhoff |
| 5,222,974 A | 6/1993 | Kensey |
| 5,232,442 A | 8/1993 | Johnson |
| 5,263,930 A | 11/1993 | Ensminger |
| 5,275,322 A | 1/1994 | Brinkerhoff |
| 5,281,199 A | 1/1994 | Ensminger |
| 5,282,827 A | 2/1994 | Kensey |
| 5,306,254 A | 4/1994 | Nash |
| 5,334,217 A | 8/1994 | Das |
| 5,350,360 A | 9/1994 | Ensminger |
| 5,356,381 A | 10/1994 | Ensminger |
| 5,441,517 A | 8/1995 | Kensey |
| 5,527,277 A | 6/1996 | Ensminger |
| 5,534,008 A | 7/1996 | Acksel |
| 5,540,715 A | 7/1996 | Katsaros |
| 5,630,833 A | 5/1997 | Katsaros |
| 5,662,616 A | 9/1997 | Bousquet |
| 5,676,689 A | 10/1997 | Kensey |
| 5,707,393 A | 1/1998 | Kensey |
| 5,741,228 A | 4/1998 | Lambrecht |
| 5,792,104 A | 8/1998 | Speckman |
| 5,817,113 A | 10/1998 | Gifford, III |
| 5,823,983 A | 10/1998 | Rosofsky |
| 5,848,989 A | 12/1998 | Villani |
| 5,861,004 A | 1/1999 | Kensey |
| 5,882,341 A | 3/1999 | Bousquet |
| 5,910,133 A | 6/1999 | Gould |
| 5,989,213 A | 11/1999 | Maginot |
| 6,004,301 A | 12/1999 | Carter |
| 6,004,341 A | 12/1999 | Zhu |
| 6,007,563 A | 12/1999 | Nash |
| 6,007,576 A | 12/1999 | McClellan |
| 6,019,788 A | 2/2000 | Butters |
| 6,090,130 A | 7/2000 | Nash |
| 6,099,508 A | 8/2000 | Bousquet |
| 6,156,016 A | 12/2000 | Maginot |
| 6,190,371 B1 | 2/2001 | Maginot |
| 6,213,973 B1 | 4/2001 | Eliasen |
| 6,261,255 B1 | 7/2001 | Mullis |
| 6,261,257 B1 | 7/2001 | Uflacker |
| 6,287,322 B1 | 9/2001 | Zhu |
| 6,355,020 B1 | 3/2002 | Bousquet |
| 6,425,901 B1 | 7/2002 | Zhu |
| 6,475,207 B1 | 11/2002 | Maginot |
| 6,508,790 B1 | 1/2003 | Lawrence |
| 6,524,326 B1 | 2/2003 | Zhu |
| 6,527,754 B1 | 3/2003 | Tallarida |
| 6,544,206 B1 | 4/2003 | Johnston, Jr. |
| 6,551,334 B2 | 4/2003 | Blatter |
| 6,569,173 B1 | 5/2003 | Blatter |
| 6,585,705 B1 | 7/2003 | Maginot |
| 6,595,941 B1 | 7/2003 | Blatter |
| 6,623,494 B1 | 9/2003 | Blatter |
| 6,626,863 B1 | 9/2003 | Berler |
| 6,626,921 B2 | 9/2003 | Blatter |
| 6,656,151 B1 | 12/2003 | Blatter |
| 6,682,489 B2 | 1/2004 | Tenerz |
| 6,723,084 B1 | 4/2004 | Maginot |
| 6,726,704 B1 | 4/2004 | Loshakove |
| 6,726,711 B1 | 4/2004 | Langenbach |
| 6,733,515 B1 | 5/2004 | Edwards |
| 6,743,218 B2 | 6/2004 | Maginot |
| 6,743,244 B2 | 6/2004 | Blatter |
| 6,764,500 B1 | 7/2004 | Muijs Van De Moer |
| 6,913,609 B2 | 7/2005 | Yencho |
| 6,960,185 B2 | 11/2005 | Adaniya |
| 6,964,675 B2 | 11/2005 | Zhu |
| 6,979,338 B1 | 12/2005 | Loshakove |
| 6,997,914 B2 | 2/2006 | Smith |
| 7,008,412 B2 | 3/2006 | Maginot |
| 7,022,131 B1 | 4/2006 | Derowe |
| 7,025,741 B2 | 4/2006 | Cull |
| 7,044,916 B2 | 5/2006 | Tenerz |
| 7,060,084 B1 | 6/2006 | Loshakove |
| 7,063,711 B1 | 6/2006 | Loshakove |
| 7,073,509 B2 | 7/2006 | Tenerz |
| 7,118,546 B2 | 10/2006 | Blatter |
| 7,128,734 B1 | 10/2006 | Wilson |
| 7,160,311 B2 | 1/2007 | Blatter |
| 7,261,705 B2 | 8/2007 | Edoga |
| 7,285,097 B2 | 10/2007 | Tenerz |
| 7,331,981 B2 | 2/2008 | Cates |
| 7,396,359 B1 | 7/2008 | Derowe |
| 7,708,722 B2 | 5/2010 | Glenn |
| 7,828,781 B2 | 11/2010 | Edoga |
| 7,901,417 B2 | 3/2011 | Blatter |
| 7,909,804 B2 | 3/2011 | Stats |
| 7,922,734 B2 | 4/2011 | Blatter |
| 8,034,064 B2 | 10/2011 | Blatter |
| 8,277,437 B2 | 10/2012 | Saal |
| 8,337,464 B2 | 12/2012 | Young |
| 8,337,465 B2 | 12/2012 | Young |
| 8,343,028 B2 | 1/2013 | Gregoric |
| 8,348,882 B2 | 1/2013 | Bardy |
| 8,398,654 B2 | 3/2013 | Franklin |
| 8,409,228 B2 | 4/2013 | Blatter |
| 8,574,204 B2 | 11/2013 | Bourne |
| 8,585,663 B2 | 11/2013 | Powers |

(56) References Cited

U.S. PATENT DOCUMENTS

| | | |
|---|---|---|
| 8,668,706 B2 | 3/2014 | Blatter |
| 8,690,816 B2 | 4/2014 | Dakin |
| 8,747,359 B2 | 6/2014 | Pakter |
| 9,033,931 B2 | 5/2015 | Young |
| 9,039,717 B2 | 5/2015 | Blatter |
| 9,179,901 B2 | 11/2015 | Young |
| 9,937,296 B2 | 4/2018 | Peh |
| 2001/0007931 A1 | 7/2001 | Blatter |
| 2001/0037094 A1 | 11/2001 | Adaniya |
| 2001/0056266 A1 | 12/2001 | Tallarida |
| 2002/0077658 A1 | 6/2002 | Ginn |
| 2002/0087127 A1 | 7/2002 | Finch |
| 2003/0004520 A1 | 1/2003 | Haarala |
| 2003/0023208 A1 | 1/2003 | Osypka |
| 2003/0078597 A1 | 4/2003 | Blatter |
| 2003/0089757 A1 | 5/2003 | Whitman |
| 2004/0097994 A1 | 5/2004 | Blatter |
| 2004/0102804 A1 | 5/2004 | Chin |
| 2004/0133173 A1 | 7/2004 | Edoga |
| 2004/0199140 A1 | 10/2004 | Rue |
| 2004/0254537 A1 | 12/2004 | Conlon |
| 2004/0260333 A1 | 12/2004 | Dubrul |
| 2005/0125060 A1 | 6/2005 | Perry |
| 2005/0171565 A1 | 8/2005 | Yencho |
| 2005/0177176 A1 | 8/2005 | Gerbi |
| 2005/0283188 A1 | 12/2005 | Loshakove |
| 2006/0247605 A1 | 11/2006 | Edoga |
| 2007/0083156 A1 | 4/2007 | Muto |
| 2007/0123811 A1 | 5/2007 | Squitieri |
| 2007/0154509 A1 | 7/2007 | Wilcher |
| 2007/0265584 A1 | 11/2007 | Hickman |
| 2008/0051811 A1 | 2/2008 | Blatter |
| 2008/0086075 A1 | 4/2008 | Isik |
| 2008/0086100 A1 | 4/2008 | Isaacson |
| 2008/0147114 A1 | 6/2008 | Derowe |
| 2008/0195124 A1 | 8/2008 | Borghi |
| 2008/0243080 A1 | 10/2008 | Chang |
| 2008/0249509 A1 | 10/2008 | Glenn |
| 2008/0269659 A1 | 10/2008 | Bergin |
| 2009/0076466 A1 | 3/2009 | Quebbemann |
| 2009/0118683 A1 | 5/2009 | Hanson |
| 2009/0131919 A1 | 5/2009 | Davey |
| 2009/0192473 A1 | 7/2009 | Crocker |
| 2009/0195124 A1 | 8/2009 | Abramovich |
| 2009/0209918 A1 | 8/2009 | Berglund |
| 2009/0270835 A1 | 10/2009 | Kushner |
| 2010/0027422 A1 | 2/2010 | Fodil |
| 2010/0121358 A1 | 5/2010 | Blatter |
| 2010/0152640 A1 | 6/2010 | Golding |
| 2010/0152658 A1 | 6/2010 | Hanson |
| 2010/0191166 A1 | 7/2010 | Phillips |
| 2010/0191179 A1 | 7/2010 | Young |
| 2010/0191191 A1 | 7/2010 | Young |
| 2010/0274223 A1 | 10/2010 | Teitelbaum |
| 2010/0318016 A1 | 12/2010 | Nugent |
| 2011/0184347 A1 | 7/2011 | Mason |
| 2011/0213309 A1 | 9/2011 | Young |
| 2011/0288462 A1 | 11/2011 | Riesinger |
| 2012/0101525 A1 | 4/2012 | Jenson |
| 2012/0245536 A1 | 9/2012 | Gerber |
| 2013/0060200 A1 | 3/2013 | Dalton |
| 2013/0066282 A1 | 3/2013 | Dalton |
| 2013/0184725 A1 | 7/2013 | Blatter |
| 2013/0245550 A1 | 9/2013 | Young |
| 2013/0245572 A1 | 9/2013 | Young |
| 2014/0163588 A1 | 6/2014 | Blatter |
| 2014/0207086 A1 | 7/2014 | Stats |
| 2014/0309609 A1 | 10/2014 | Hsu |
| 2015/0190587 A1 | 7/2015 | Peh |
| 2018/0264246 A1 | 9/2018 | Lim |
| 2018/0272056 A1 | 9/2018 | Peh |
| 2018/0289550 A1 | 10/2018 | Ye |

FOREIGN PATENT DOCUMENTS

| | | |
|---|---|---|
| EP | 0356810 | 3/1990 |
| EP | 2583646 A1 | 4/2013 |
| GB | 2282760 | 4/1995 |
| JP | 5395592 | 1/1977 |
| JP | S5720272 | 2/1982 |
| JP | 08501008 | 2/1996 |
| JP | H11500031 | 1/1999 |
| JP | 2004518476 | 6/2004 |
| JP | 2005349121 | 12/2005 |
| WO | 9535126 | 12/1995 |
| WO | 1998018506 | 5/1998 |
| WO | 1999033512 | 7/1999 |
| WO | 03082127 A1 | 10/2003 |
| WO | 2006045608 | 5/2006 |
| WO | 2006092724 | 9/2006 |
| WO | 2007109164 | 9/2007 |
| WO | 2009149474 | 12/2009 |
| WO | 2010011995 | 1/2010 |
| WO | 2010088532 | 8/2010 |
| WO | 2010088541 | 8/2010 |
| WO | 2010107698 | 9/2010 |
| WO | 2011094712 | 8/2011 |
| WO | 2012516223 | 7/2012 |
| WO | 2013128292 | 9/2013 |
| WO | 2014017986 | 1/2014 |
| WO | 2015089372 | 6/2015 |

OTHER PUBLICATIONS

International Search Report dated Apr. 8, 2010 in International Application No. PCT/US2010/022607, which claims priority to U.S. Appl. No. 61/148,372, filed Jan. 29, 2009 and U.S. Appl. No. 61/229,023, filed Jul. 28, 2009. (3 pages).
International Preliminary Report on Patentability dated Aug. 2, 2011 in International Application No. PCT/US2010/022607, which claims priority to U.S. Appl. No. 61/148,372, filed Jan. 29, 2009 and U.S. Appl. No. 61/229,023, filed Jul. 28, 2009. (9 pages).
International Search Report dated Jul. 31, 2009 in International Application No. PCT/US2009/046664, which claims priority to U.S. Appl. No. 61/059,590, filed Jun. 6, 2008. (3 pages).
International Preliminary Report on Patentability dated Dec. 6, 2010 in International Application No. PCT/US2009/046664, which claims priority to U.S. Appl. No. 61/059,590, filed Jun. 6, 2008. (8 pages).
International Search Report and the Written Opinion of the International Searching Authority dated Dec. 13, 2018 in International Application No. PCT/IB2018/000437 (pp. 1-18).
International Search Report and the Written Opinion of the International Searching Authority dated Apr. 8, 2010 in International Application No. PCT/US2010/022622, now published as WO 2010/088541. (3 pages).
International Preliminary Report on Patentability dated Aug. 11, 2011 in International Application No. PCT/US2010/022622, now published as WO 2010/088541. (11 pages).
International Search Report and the Written Opinion of the International Searching Authority dated Mar. 25, 2011 in International Application No. PCT/US2011/023228, now published as WO 2011/094712. (9 pages).
International Preliminary Report on Patentability dated Jul. 31, 2012 in International Application No. PCT/US2011/023228. (7 pages).
Extended European Search Report dated Jul. 2, 2014 in European Application No. 11737838.0. (6 pages).
Extended European Search Report dated Mar. 4, 2015 in European Application No. 10736487.9. (6 pages).
Vascular Access 2006, American Journal of Kidney Disease, vol. 48 No. 1, Jul. 2006, S180-S182.
Form PCT ISA 206—International Application No. PCT/IB2018/000437; International Filing Date: Apr. 4, 2018 (10 pages).
Jennings, et al., "The Venous Window Needle Guide, a hemodialysis cannulation device for salvage of uncannulatable arteriovenous fistulas", Journal of Vascular Surgery, Oct. 2014, vol. 60, No. 4, pp. 1024-1032.

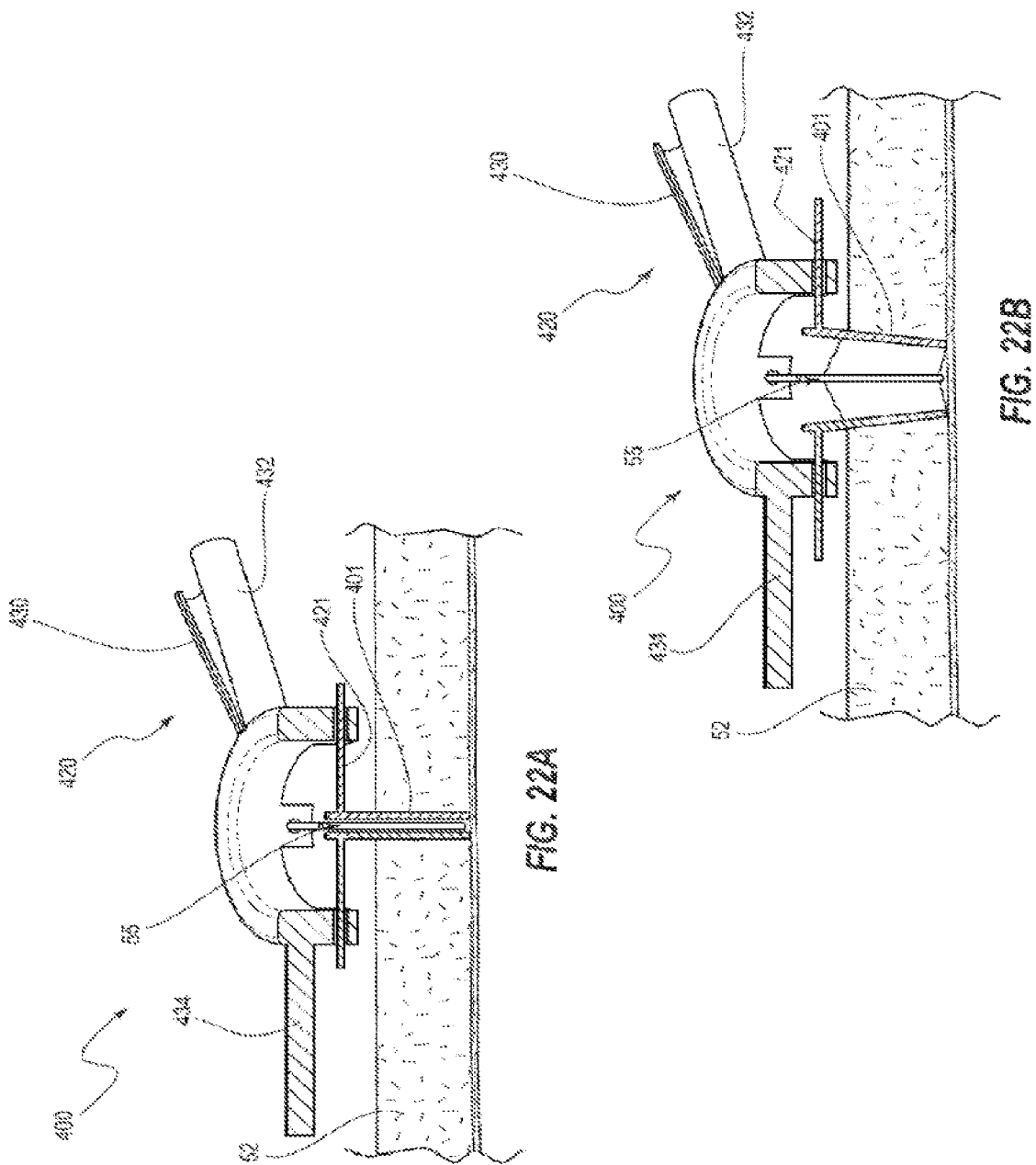

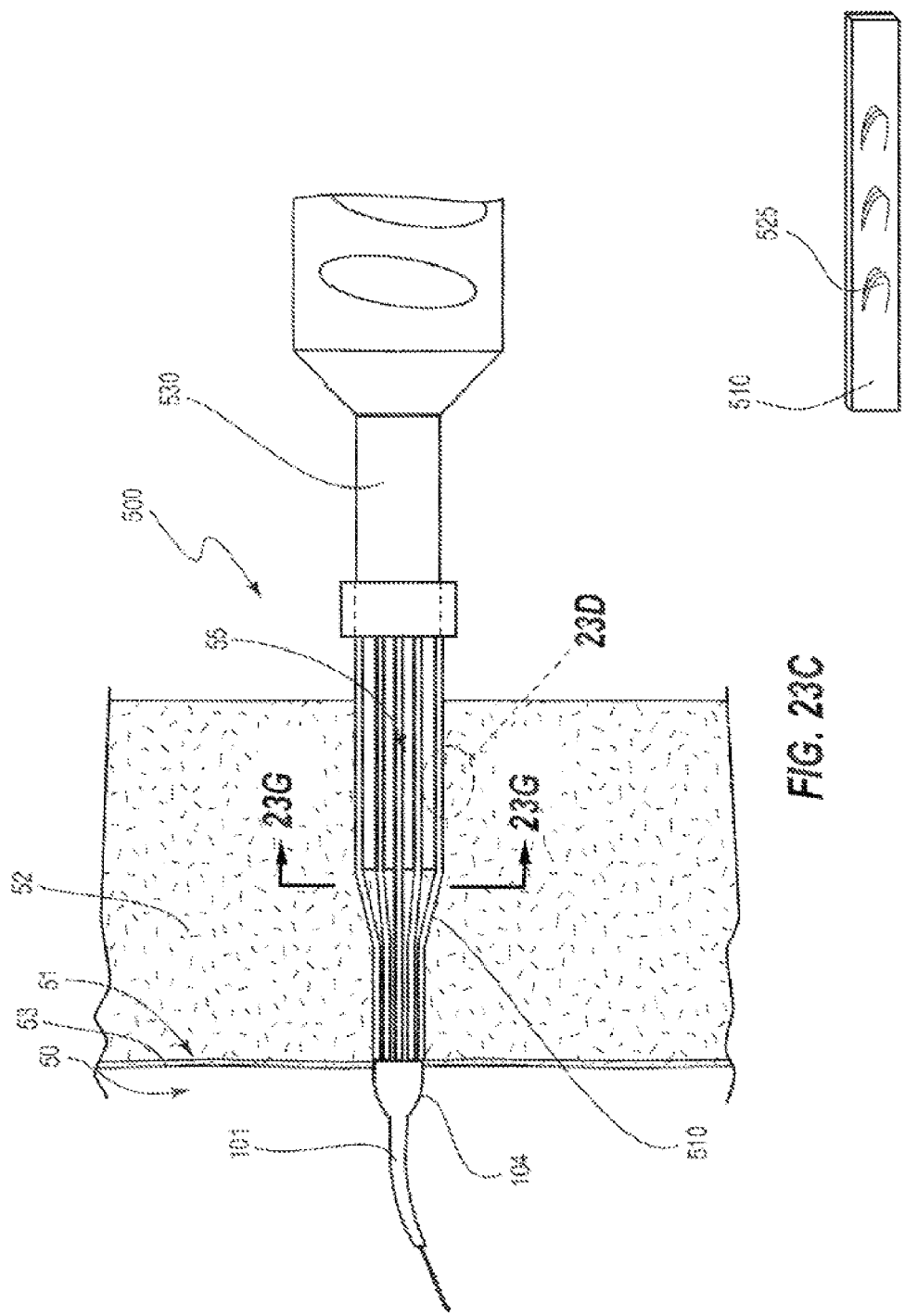

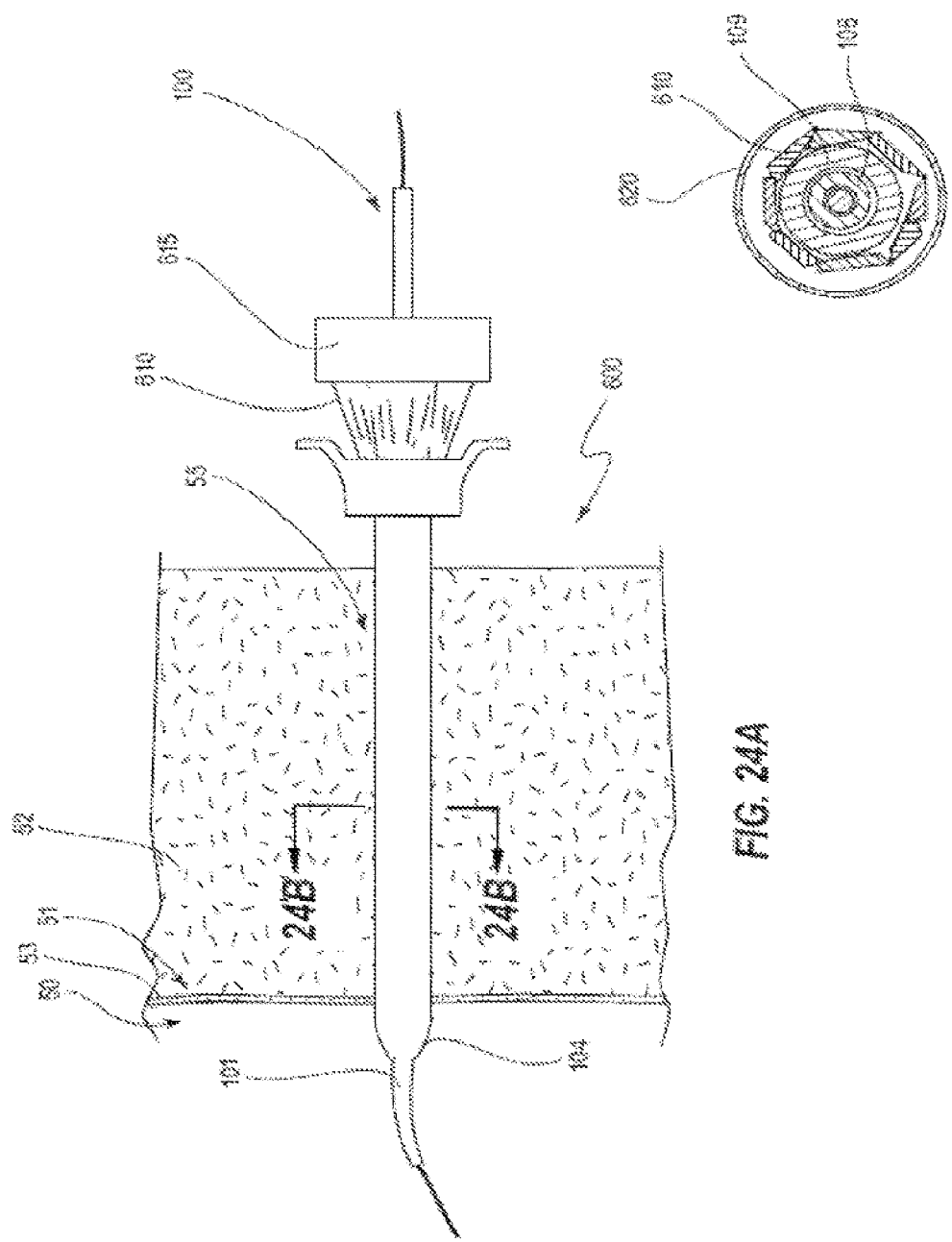

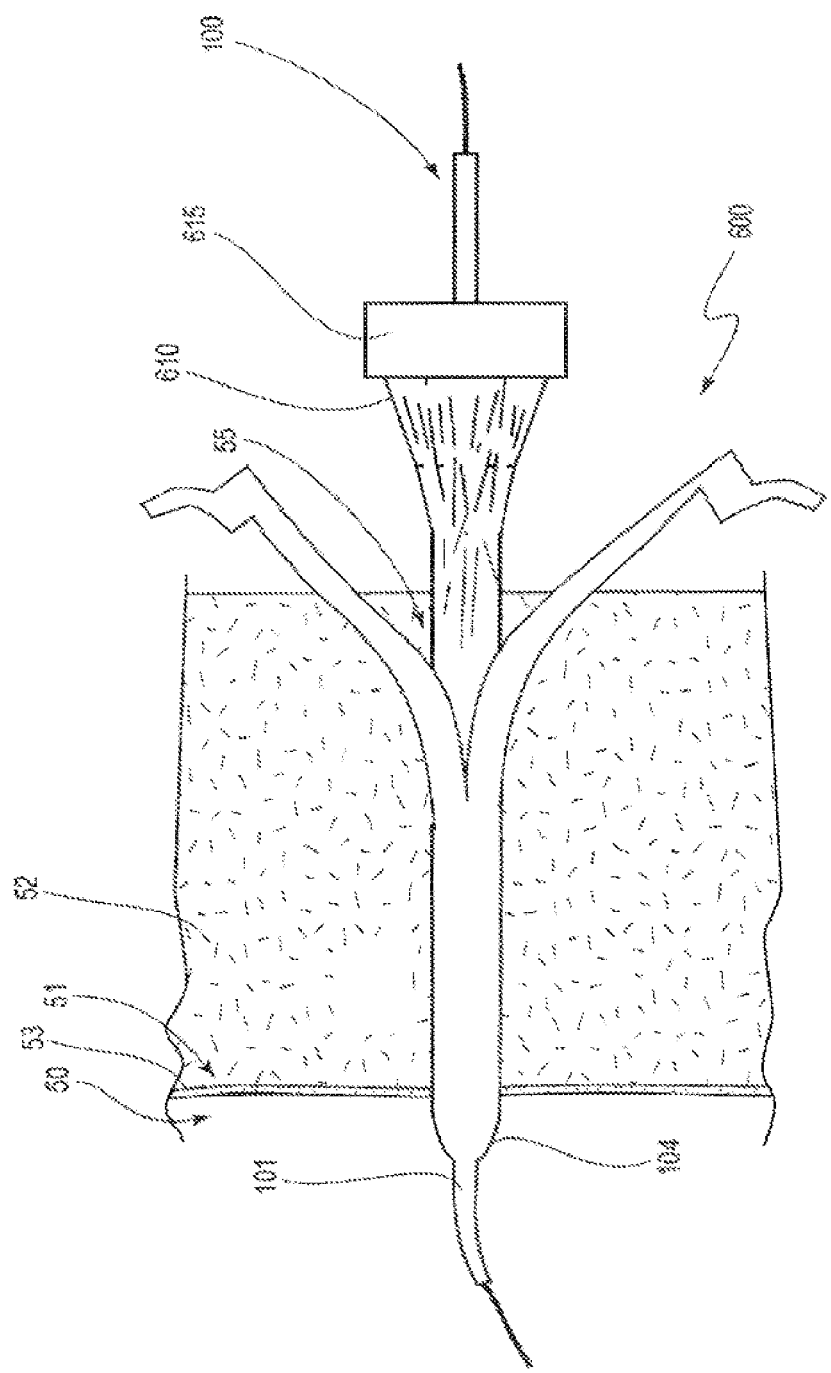

METHODS OF ATTACHING AN IMPLANT TO A VESSEL

CROSS-REFERENCE TO RELATED APPLICATIONS

This application is a continuation of U.S. patent application Ser. No. 14/720,969, filed on May 15, 2015, titled METHODS OF ATTACHING AN IMPLANT TO A VESSEL, now abandoned, which is a continuation of U.S. patent application Ser. No. 14/181,401, filed on Feb. 14, 2014, titled TISSUE MANAGEMENT APPARATUS FOR VASCULAR ACCESS, corresponding to U.S. Pat. No. 9,039,717, which is a continuation of U.S. patent application Ser. No. 13/781,575, filed on Feb. 28, 2013, titled TISSUE MANAGEMENT APPARATUS FOR VASCULAR ACCESS, now U.S. Pat. No. 8,668,706, which is a continuation of U.S. patent application Ser. No. 12/480,678, filed on Jun. 8, 2009, titled TISSUE MANAGEMENT METHODS, APPARATUS, AND SYSTEMS, now U.S. Pat. No. 8,409,228, which claims the benefit under 35 U.S.C. § 119(e) of U.S. Provisional Patent Application No. 61/059,590, filed on Jun. 6, 2008, titled VASCULAR ACCESS METHODS, APPARATUS AND SYSTEMS, the entirety of each of which is hereby incorporated by reference herein.

STATEMENT REGARDING FEDERALLY SPONSORED RESEARCH OR DEVELOPMENT

The invention was made with support from the U.S. Government under Grant No. SBIR R43 CA 139608 and Grant No. SBIR R44 CA 139608, which were awarded by the National Institutes of Health. The U.S. Government has certain rights in the invention.

TECHNICAL FIELD

The present disclosure relates to methods, apparatus, and systems for managing tissue.

SUMMARY

Disclosed herein are embodiments of methods, apparatus, and systems for managing tissue, such as, for example, for preparing a vessel for anastomosis and/or for creating an anastomosis with a vessel.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 22A is a perspective view of another embodiment of a tract dilator that includes a ratchet mechanism;

FIG. 22B is a perspective view of the tract dilator of FIG. 22A in another operational state;

FIG. 23C illustrates an elevation view of the tract dilator of FIG. 23A being expanded by the insertion of a plunger therein;

FIG. 23D is a perspective view of a portion of a ribbon of an embodiment of the tract dilator of FIG. 23A that includes barbs to resist backout of the tract dilator;

FIG. 24A illustrates an elevation view and a cross-sectional view of another embodiment of a tract dilator that includes a sleeve retained in a non-expanded or folded state by a separable sheath;

FIG. 24B is a cross-sectional view of the same;

FIG. 24C is an elevation view of the tract dilator of FIG. 24A showing the separable sheath being removed from the sleeve;

DETAILED DESCRIPTION

Described herein are certain embodiments of methods, apparatus and systems for managing tissue in connection with attaching an access device to the vasculature of a patient or to some other suitable site within the patient. In some embodiments, an access tube is anastomosed to a vessel and can be used for repeated access thereto, such as for hemodialysis or other procedures. In other embodiments, an access port is anastomosed to a vessel. In various embodiments, the access tube or the access port can be joined to the vessel via percutaneous procedures and/or devices.

Although many of the examples provided herein relate to the anastomosis of devices to blood vessels, this method of disclosure is employed for the sake of convenience and efficiency, but should not be construed as limiting of the types of procedures with which embodiments may be used. Indeed, embodiments of the methods, systems, and apparatus disclosed herein can be used with vessels other than blood vessels, and may be used with organs such as, for example, the intestine or the bladder. As used herein, the term vessel is a broad term that can include any hollow or walled organ or structure of a living organism.

Figure 4:
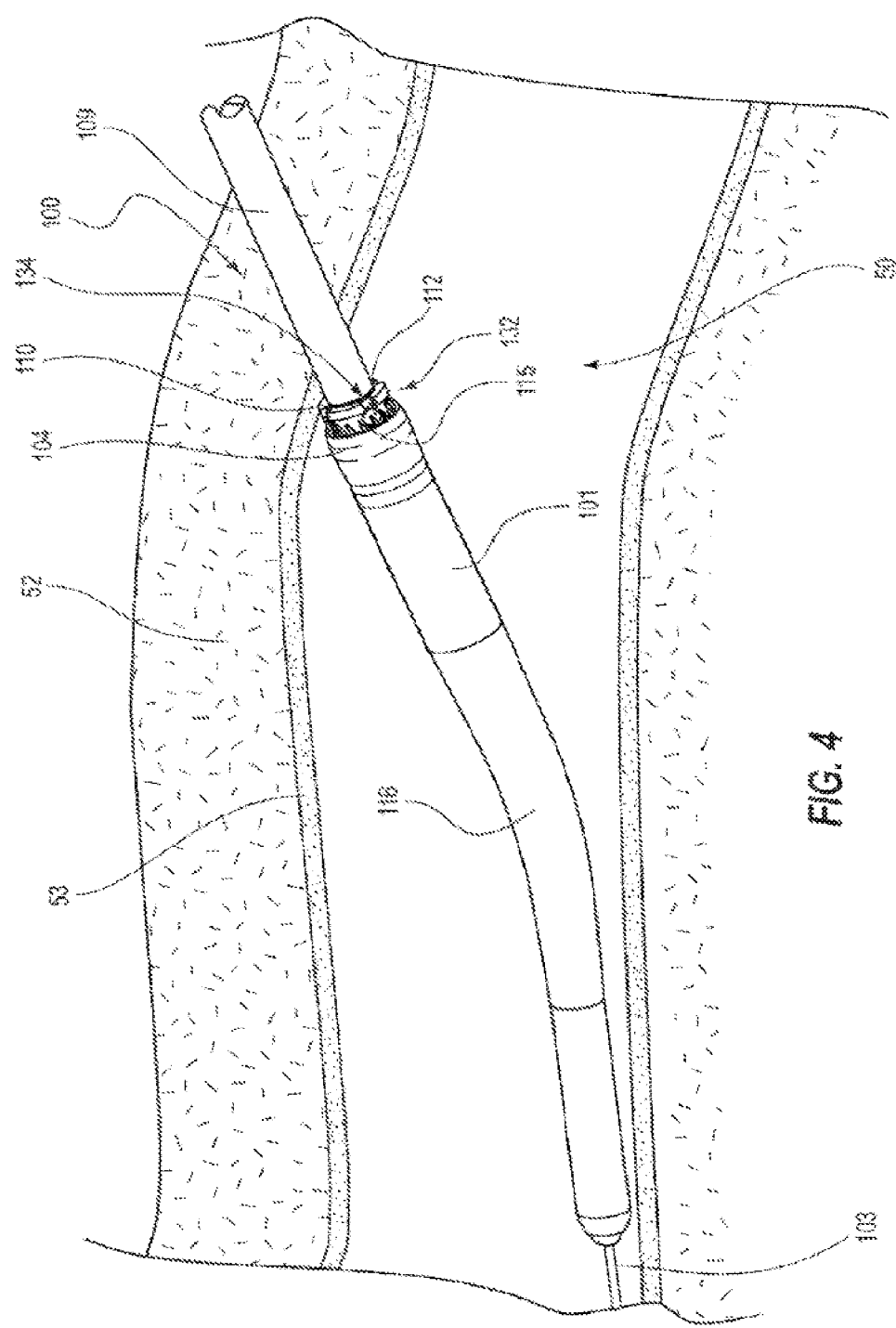
FIG. 4 is a perspective view of a portion of the clamp assembly of FIG. 1 being inserted into a blood vessel that is shown in cross-section.

In some embodiments, an opening is formed in a wall of a blood vessel and at least a portion of a clamp device is inserted therein (see, e.g., FIG. 4). The clamp device can capture and secure a portion of the blood vessel wall (see, e.g., FIG. 7). A dilation device can be used to expand tissue surrounding the clamp device so as to expose a larger area of the blood vessel wall and create a tract through which an access device can be inserted and moved to a position adjacent the vessel (see, e.g., FIG. 11). A connection, approximation, or anastomosis actuation device can be configured to attach the access device to the vessel (see, e.g., FIGS. 14-19). The clamping device, dilation device, and anastomosis actuation device can be removed from the patient upon completion of the anastomosis.

Certain embodiments are suitable for hemodialysis or similar procedures. In some embodiments, a conduit is anastomosed to a vessel and a proximal end thereof can be accessible outside of a patient's body. An obturator can be positioned within the conduit to maintain patency of the anastomosis and conduit. If desired, the obturator can be removed and a hemodialysis catheter can be inserted through the conduit into the patient's vessel. The catheter may be connected to a hemodialysis machine and hemodialysis can be conducted. Upon completion of the hemodialysis, the catheter can be removed from the patient's vessel and entirely or partially removed from the conduit. The obturator can then be used to again occlude the anastomosis until further vascular access is desired or required. In other embodiments, a port is anastomosed to the blood vessel. The port can be implanted within the patient such that no portion of it extends outside of the skin of the patient.

The term anastomosis is used broadly herein, and includes the ordinary meaning of this term. In some cases, an anastomosis can be an operative union of two hollow or tubular structures, which can provide substantially uninterrupted flow through the structures. In other cases, an anastomosis can act as a portal to selectively introduce one or more devices, such as, for example, catheters or needles, from one tubular structure into another. In some embodiments, the hollow or tubular structure is relatively long and can extend percutaneously between the blood vessel and an exterior of a patient, whereas in other embodiments, the hollow or tubular structure that is anastomosed to the vessel can be relatively short and/or relatively small and can be fully implanted within the patient.

Figure 1:
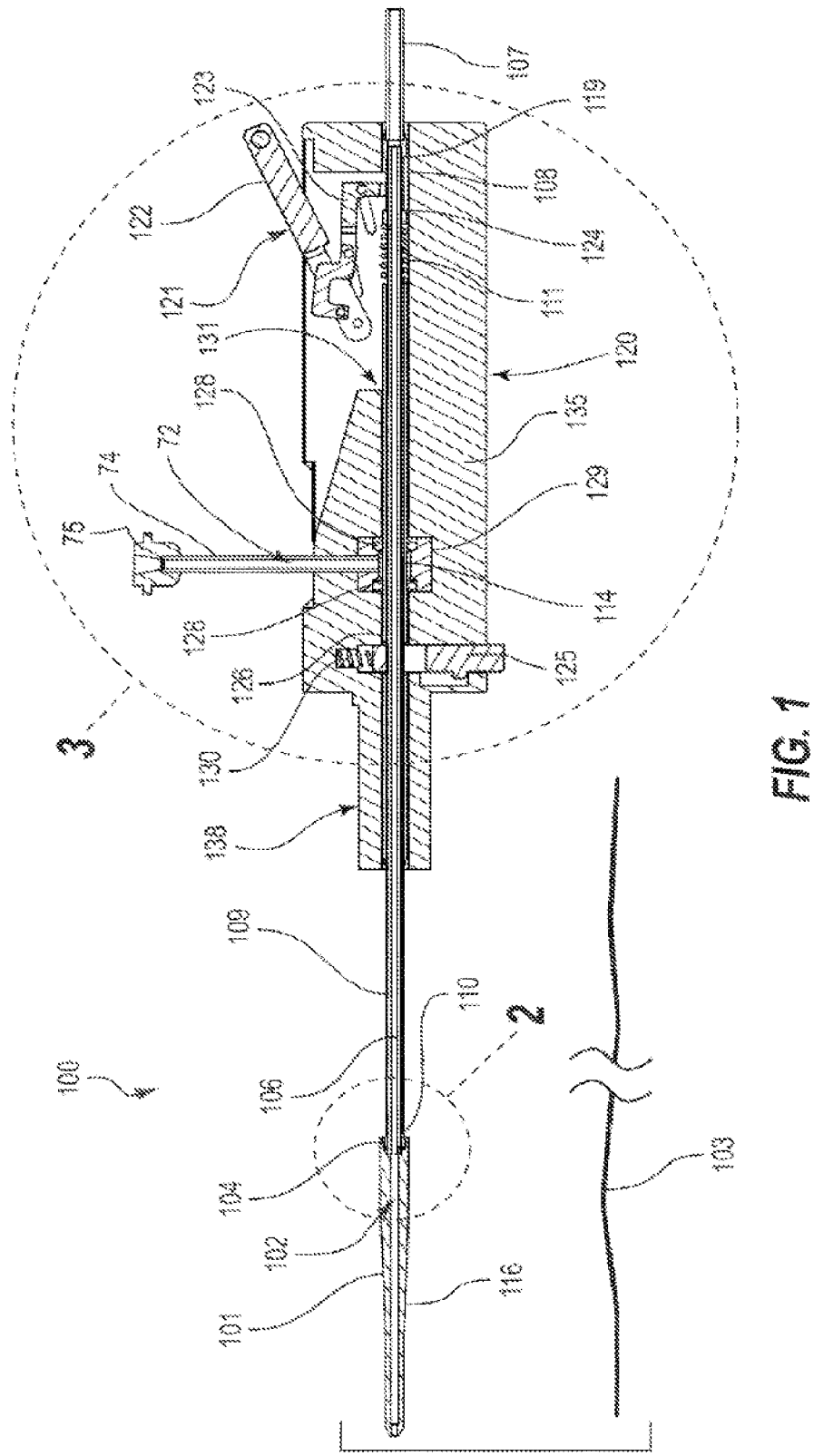
FIG. 1 is a cross-sectional view of an embodiment of a clamp assembly and an embodiment of a clamp actuation device coupled therewith.
Figure 2:
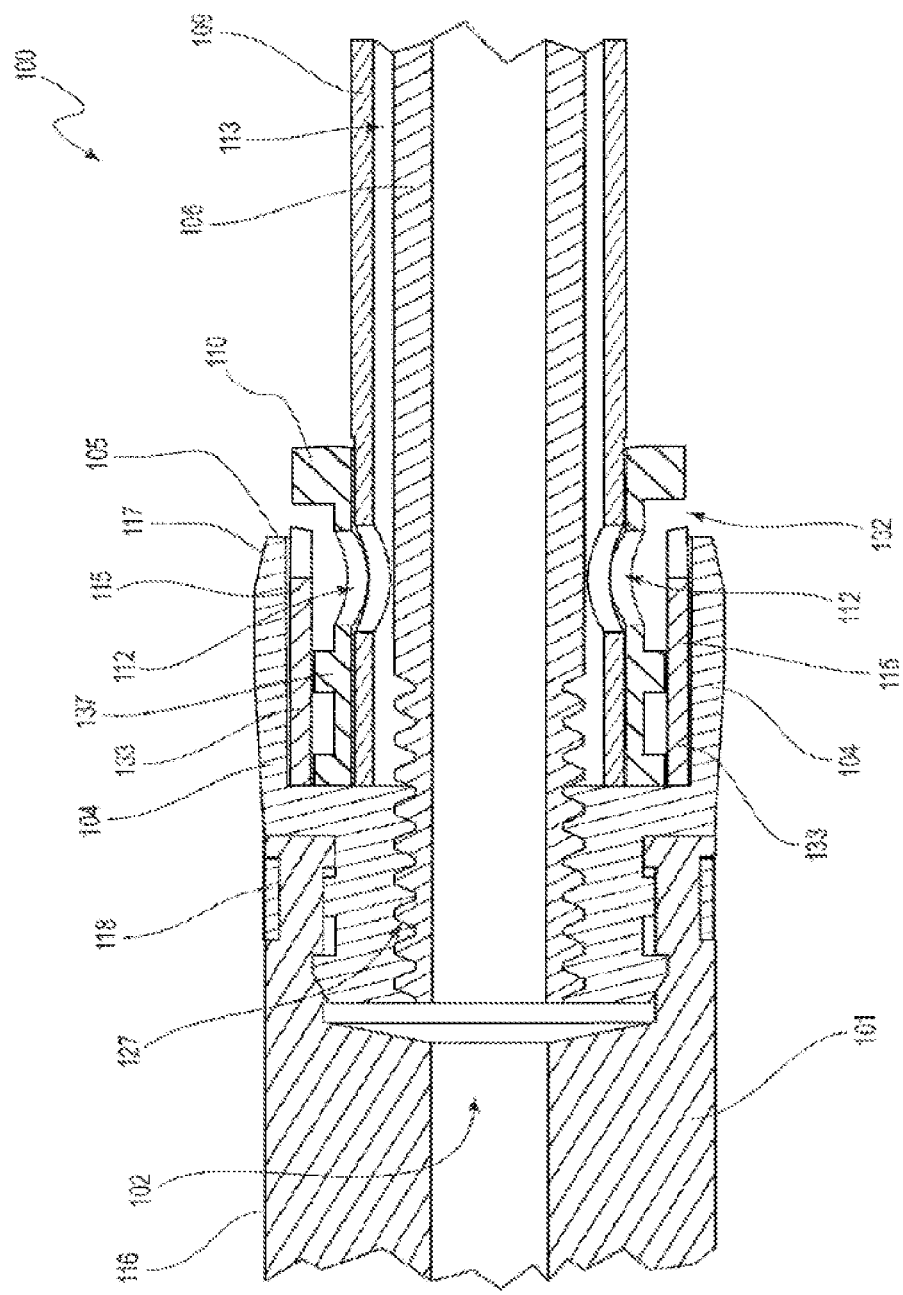
FIG. 2 is an enlarged cross-sectional view of an anvil region of the clamp assembly of FIG. 1 in a closed configuration.

With reference to FIGS. 1 and 2, in certain embodiments, a clamp assembly 100 can comprise an insertion or introducer tip 101, an anvil 104, an anvil pull member 106, a clamp tube 109, and a clamp foot 110. As further discussed below, in certain embodiments, the introducer tip 101 is connected to the anvil 104, which in turn is connected to the anvil pull member 106 such that movement of the anvil pull member 106 effects movement of the introducer tip 101 and the anvil 104. The anvil pull member 106 and the clamp tube 109 can move independently of each other. For example, in the illustrated embodiment, the anvil pull member 106 is positioned within the clamp tube 109 and is substantially coaxial therewith, and the anvil pull member 106 can slide or otherwise move axially relative to (e.g., telescopically within) the clamp tube 109. Relative movement of the anvil pull member 106 and the clamp tube 109 can alter the relative spacing of the anvil 104 and the clamp foot 110.

With reference to FIGS. 1, 2, and 4, the introducer tip 101 can be located at a distal end of the clamp assembly 100. The introducer tip 101 can be flexible so as to readily deform to follow a lumen 50 of a blood vessel 51 once inserted therein, and it can be substantially atraumatic to an inner surface of a wall 53 of the vessel 51 so as to be able to follow the inner surface substantially without damaging the wall 53. For example, in various embodiments, the introducer tip 101 can comprise a flexible material such as polyurethane, thermoplastic elastomer, or silicone rubber. The introducer tip 101 can define at least a portion of a lumen 102 of the clamp assembly 100 through which a guidewire 103 may pass. Accordingly, in some embodiments, the introducer tip 101 can be inserted into the blood vessel 51 over the guidewire 103, and may bend or otherwise deform to follow a contour of the guidewire 103 and/or a contour of the vessel wall 53.

An exterior surface 116 of the introducer tip 101 may be tapered in such a manner that the introducer tip 101 provides its own dilation of skin tissue 52 and the vessel wall 53. The tapered surface 116 of the tip can expand from a relatively small diameter near a distal end of the introducer tip 101 to a larger diameter at or near a proximal end of the introducer tip 101, which can be adjacent the anvil 104. The term "diameter" is used broadly herein, and does not necessarily imply that the measured item is cylindrical or otherwise circularly symmetric. For example, the term can include the maximum transverse dimension of an item, where the transverse dimension is defined as a distance between two points on a periphery of the item, as measured along a straight line that extends through a longitudinal axis of the item in a direction that is substantially perpendicular to the longitudinal axis.

In certain embodiments, at least a portion of the introducer tip 101 is radiopaque. For example, in various embodiments, the introducer tip 101 can comprise one or more radiopaque agents such as barium sulfate, bismuth trioxide, titanium dioxide, or the like. In other or further embodiments, the introducer tip 101 can be coated with a lubricious coating, such as a hydrophilic polymer, silicone oil, or other suitable lubricious material. The coating can facilitate a smooth passage of the introducer tip 101 through the skin tissue 52, the vessel wall 53, and into the vessel lumen 50.

With reference to FIG. 2, in some embodiments, the introducer tip 101 is connected to the anvil 104. The introducer tip 101 can be secured to the anvil 104 utilizing a crimp band 118, adhesive, solvent bonding, and/or any other suitable technique. In various embodiments, the anvil 104 can be made from a material comprising one or more of, for example, Delrin® (available from DuPont™ of Wilmington, Del.), polyurethane, polyvinylchloride, or other similar materials. The anvil 104 can be manufactured using any suitable manufacturing method, such as, for example, injection molding, machining, or casting. In some embodiments, the outer surface 116 of the introducer tip 101 can smoothly transition to an outer surface of the anvil 104, which can facilitate insertion of the anvil 104 into the vessel lumen 50.

With continued reference to FIG. 2, in certain embodiments, a proximal surface 105 of the anvil 104 is substantially flat or substantially planar, and the plane defined thereby can be perpendicular to a longitudinal axis of the anvil 104. In some embodiments, a proximal portion of the anvil 104 can include a chamfer 117, which can extend around all or substantially all of a periphery of the anvil 104. The chamfer 117 is discussed further below. In other embodiments, the proximal surface 105 can be rounded (e.g., dome-shaped) or angled (e.g., conical or frustoconical).

The anvil 104 can be generally hollow such that a distal portion of the clamp tube 109 can be received therein. In some embodiments, the anvil 104 can receive a distal portion of the anvil pull tube 106 and the distal end of the anvil 104 can be attached thereto. In the illustrated embodiment, the anvil 104 is attached to the anvil pull tube 106 via a threaded connection 127. In other or further embodiments, the anvil 104 and the pull tube 106 can be attached to each other via an adhesive, welding, and/or in any other suitable manner. In some embodiments, the anvil 104 is over molded onto the distal end of the anvil pull tube 208.

The anvil pull tube 106 can be hollow so as to define at least a portion of the lumen 102, which can allow for the passage of the guidewire 103 through the clamp assembly 100. The anvil pull tube 106 can be substantially rigid and can have sufficient columnar strength to impart an insertion force to the introducer tip 101. The anvil pull tube 106 can comprise stainless steel and/or any other suitable rigid material.

Figure 3:
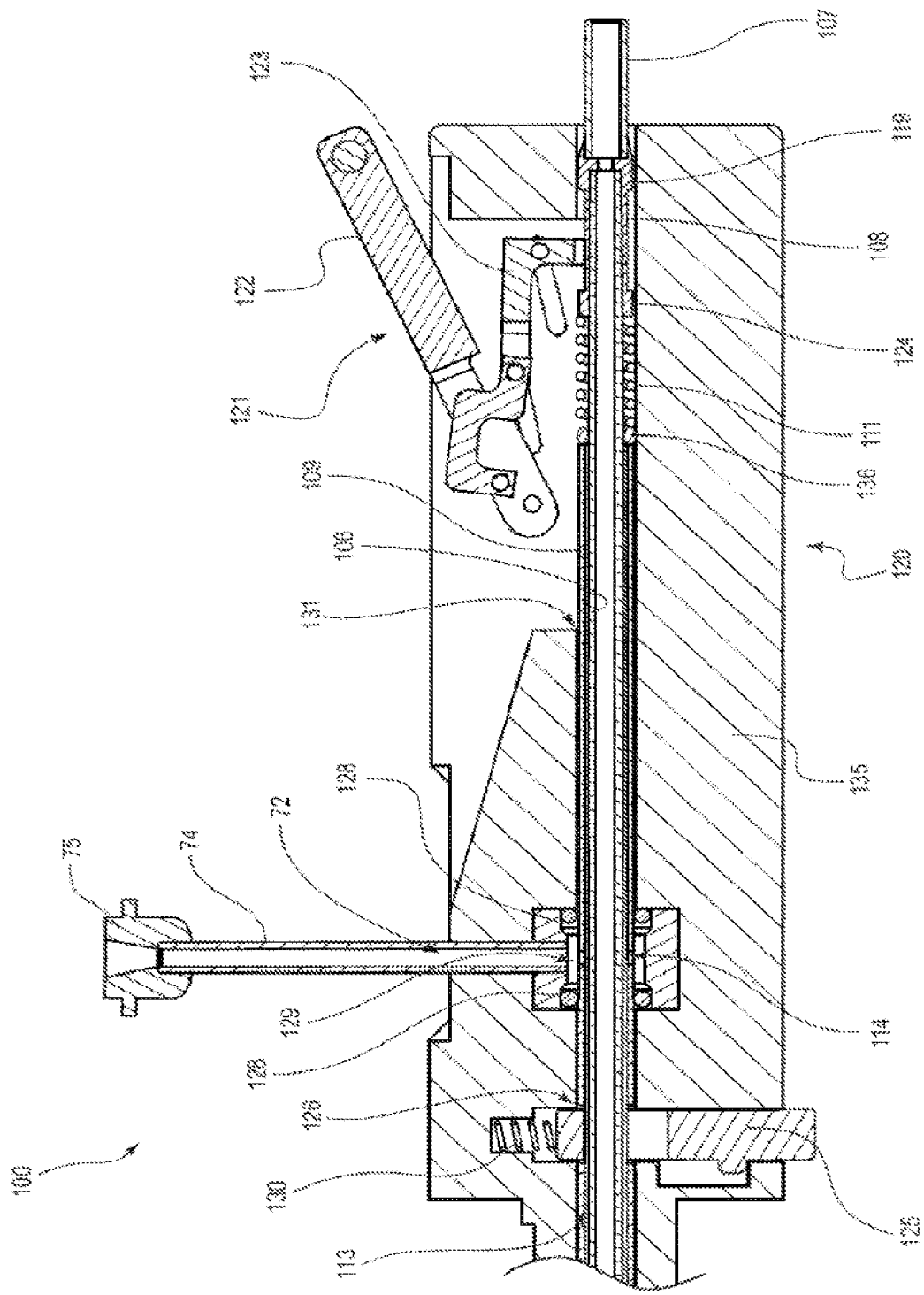
FIG. 3 is an enlarged cross-sectional view of a portion of the actuation device of FIG. 1.

With reference to FIGS. 1 and 3, an extender tube 107 can be secured to a proximal end of the anvil pull tube 106. In various embodiments, the tube 107 can comprise plastic, such as, for example, polyetheretherketone (PEEK), and/or similar materials. In certain embodiments, a clutch 108 can be positioned at or near the connection site of the anvil pull tube 106 and the extender tube 107, or it can itself serve as a connector between the tubes 106, 107. The clutch 108 can include a proximal shoulder 119 and a distal shoulder 124. The clutch 108 can be made of any suitable material, such as one or more of PEEK, metal, or the like. The clutch 108 can be attached to the proximal end of the anvil pull tube 106 in any suitable manner, such as, for example, via a threaded connection and/or an adhesive. In other embodiments, the extender tube 107 can be eliminated. For example, the anvil pull tube 106 can itself extend proximally beyond the clutch 108.

With reference to FIGS. 1-3, the clamp tube 109 can be positioned over or outside of the anvil pull tube 106. In some embodiments, an inner diameter of the clamp tube 109 is only slightly larger than an outer diameter of the anvil pull tube 106 such that the tubes 106, 109 are in sliding engagement with each other, and contacting surfaces or the interface of the tubes 106, 109 can be relatively resistant to the passage of air or fluid thereby. In other embodiments, the inner diameter of the clamp tube 109 is sufficiently larger than the outer diameter of the anvil pull tube 106 such that friction between the tubes 106, 109 is reduced or eliminated. For example, in the illustrated embodiment, the tubes 106, 109 define a channel 113 through which air and/or fluid may be conducted, as further discussed below. In the illustrated embodiment, the channel 113 is substantially annular due to the substantially concentric cylindrical structures of the clamp tube 109 and the anvil pull member 106. Other arrangements are possible.

As shown in FIG. 2, the clamp tube 109 can include a clamp foot 110 at or near its distal end. The clamp foot 110 can be substantially disk-shaped and can have a larger diameter than more proximal portions of the clamp tube 109. In some embodiments, the clamp foot 110 is integrally formed with the clamp tube 109. In the illustrated embodiment, the clamp foot 110 extends radially outwardly from a proximal end of a clamp foot body 137 that is securely attached to the clamp tube 109. As further discussed below, in some embodiments, the clamp foot 110 can include one or more openings or notches 134 therein (see FIGS. 4, 5, and 7).

With reference to FIGS. 1 and 3, in some embodiments, a clamp actuation device 120 can be selectively positioned over a portion of the clamp assembly 100. In some embodiments, the clamp actuation device 120 can include a housing 135 that is configured to be slid or otherwise moved over a proximal end of the clamp assembly 100 (e.g., over the tube 107) and into a secured position. In certain embodiments, the housing 135 is sized and shaped to be gripped as a handle. The clamp actuation device 120 can be releasably secured (e.g., selectively fixedly attached) to the clamp tube 109 in any suitable manner such that the clamp actuation device 120 and the clamp tube 109 are substantially stationary relative to each other when in a secured orientation.

In the illustrated embodiment, selective engagement and disengagement of the clamp actuation device 120 to and from the clamp tube 109 is achieved via an engagement actuator 125, such as a button. In the illustrated embodiment, the actuator 125 is coupled with a biasing element 130, such as a compressed spring, that urges the actuator 125 away from a longitudinal axis of the clamp actuation device 120. In some embodiments, when the actuator 125 is in a natural or non-actuated state, it protrudes through a base wall of the housing 135 such that a user can manipulate the actuator 125 by depressing it inwardly toward the longitudinal axis of the housing 135. In some embodiments, an opening is defined through the actuator 125, and depressing the actuator 125 inwardly against the bias of the biasing element 130 aligns the opening with a channel 131 defined by the housing 135, thereby opening the channel 131 to allow the proximal end of the clamp assembly 100 to pass through the channel 131 in a proximal direction. In some embodiments, the clamp tube 109 includes a notch or depression 126 that extends inwardly toward a central axis of the clamp tube 109. The actuator 125 can be released such that the biasing element 130 urges a portion of the actuator 125 into the clamp tube depression 126 to thereby secure the clamp actuation device 120 in place. To remove the clamp actuation device 120, the actuator 125 can be depressed to align the opening thereof with the channel 131, and the clamp actuation device 120 can be moved in a proximal direction and removed over the proximal end of the clamp assembly 100. Other suitable arrangements of the actuator 125 are possible.

The clamp actuation device 120 can include a clamp actuator 121, which in the illustrated embodiment comprises a lever having an outer arm 122 and an inner arm 123 that are pivotally coupled to each other. The clamp actuator 121 can be moved between an open or accessible state and a clamped, approximated, or closed state, which can move the clamp assembly 100 between an open or accessible orientation and a clamped, approximated, or closed orientation, respectively. In the illustrated embodiment, the clamp actuator 121 is in the open state when the outer arm 122 is rotated forward toward a distal end of the clamp actuation device 120 and is in the closed state when the outer arm 122 is rotated rearward toward a proximal end of the clamp actuation device 120 (i.e., rotated to the position illustrated in FIGS. 1 and 3).

With reference to FIG. 3, in some embodiments, a biasing element 111 can be configured to bias the anvil pull member 106 proximally relative to the clamp actuation device 120.

In the illustrated embodiment, the biasing element 111 comprises a compression spring. A distal end of the biasing element 111 is positioned at and/or is secured to the proximal end of the clamp tube 109. As previously mentioned, the clutch 108 can be secured to the anvil pull member 106, and a distal end of the clutch 108 can be positioned at and/or secured to the proximal end of the biasing element 111. Accordingly, the biasing element 111 can provide a proximally directed biasing force on the clutch 108, and hence on the anvil pull member 106. The biasing force can in turn urge the anvil 104 toward the clamp foot 110 (see FIG. 2).

In the illustrated embodiment, moving the actuator 121 from the closed state to the open state comprises rotating the outer arm 122 forwardly, which causes the inner arm 123 to engage or contact the distal shoulder 124 of the clutch 108. Continued forward rotation of the outer arm 122 can cause the inner arm 123 to urge the clutch 108, and hence the anvil pull member 106, distally against the bias provided by the biasing element 111.

With reference to FIG. 2, such distal movement of the anvil pull member 106 can cause the anvil 104 to move distally away from a clamp foot 110, and can thereby create, or can broaden or widen, an opening or gap 132 between the anvil 104 and the clamp foot 110 when the actuator 121 is in the open state. The gap 132 can be reduced in size or closed by movement of the actuator 121 to the closed state.

In other embodiments, the distal end of the biasing element 111 can be attached directly to the clamp actuation device 120 (e.g., to the housing 135) and may or may not be at or near the proximal end of the clamp tube 109. In still other embodiments, the anvil pull member 106 can be selectively fixed relative to the clamp actuation device 120 such that actuation of the actuator 121 effects movement of the clamp tube 109 relative to the anvil pull member 106. The actuator 121 thus can move the clamp foot 110 relative to the anvil 104. For example, in some embodiments, when the actuator 121 is moved from the closed position to the open position, the clamp foot 110 is moved away from the anvil 104 in a proximal direction, thereby creating or broadening the gap 132 between the clamp foot 110 and the anvil 104.

Figure 5:
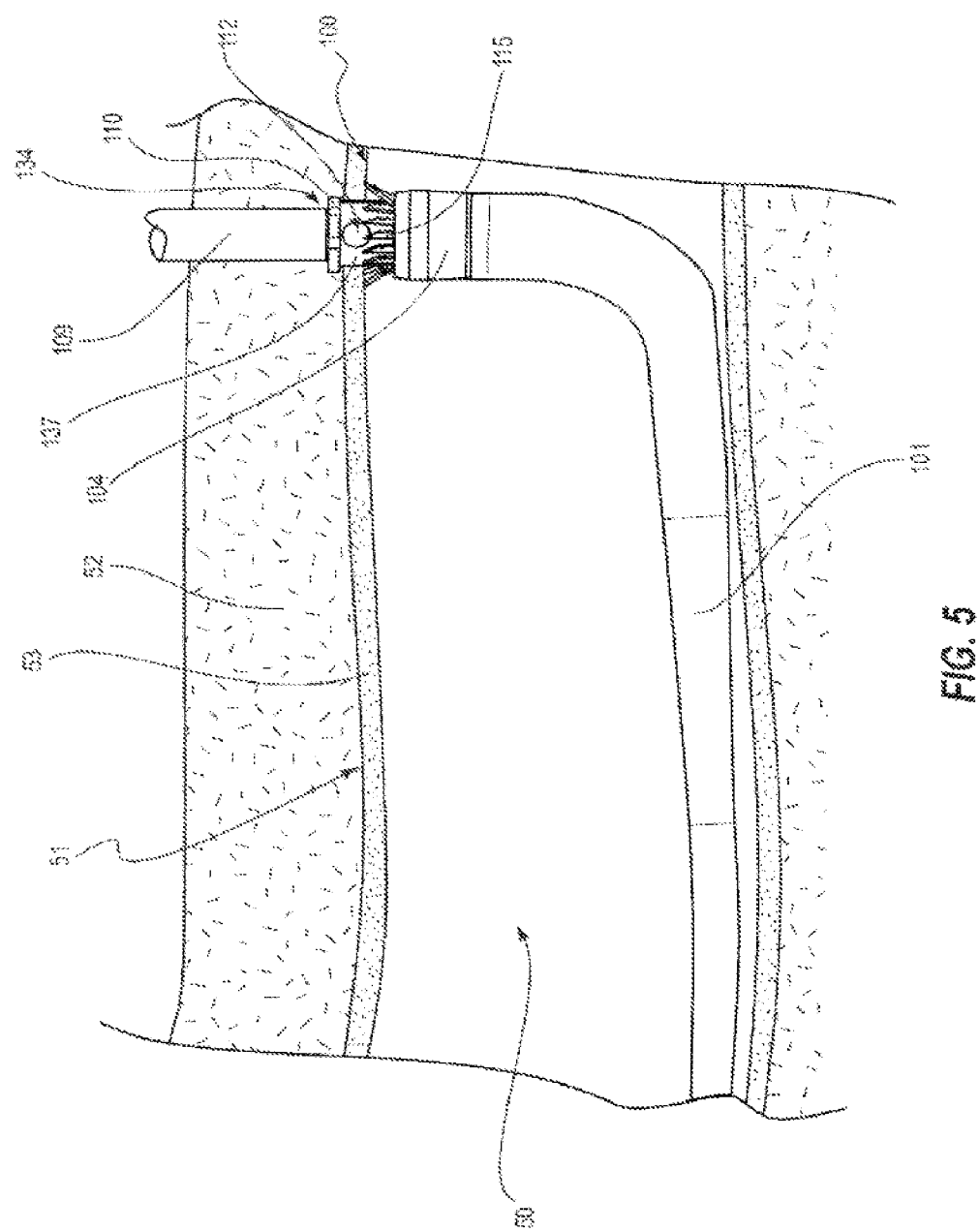
FIG. 5 is a perspective view of a portion of the clamp assembly of FIG. 1 shown in an open configuration with an embodiment of a clamp foot separated from an embodiment of an anvil such that a wall of the blood vessel is between the clamp foot and the anvil.
Figure 6:
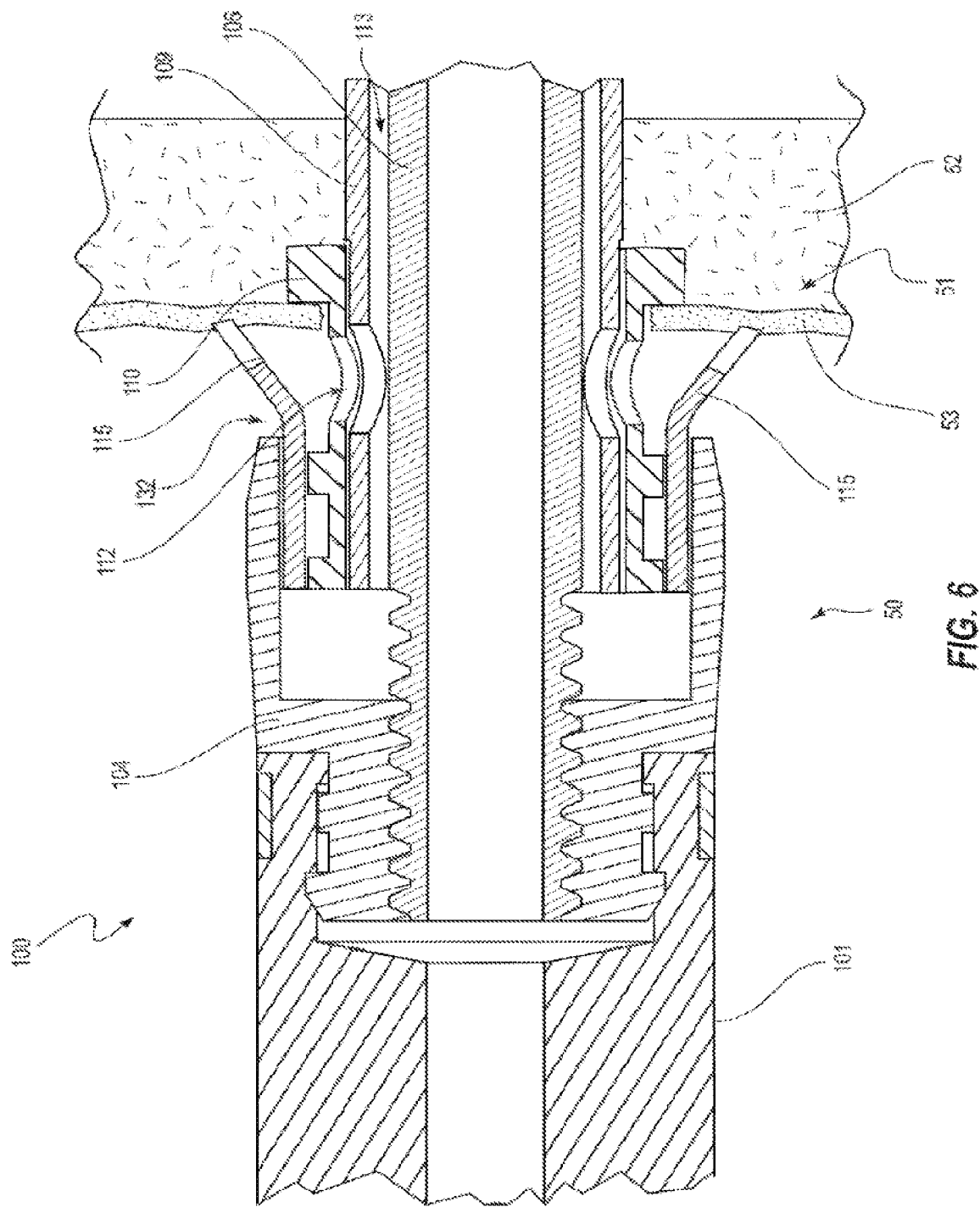
FIG. 6 is a cross-sectional view of a portion of the clamp assembly shown in FIG. 5.

Referring, for example, to FIGS. 2, 5, and 6, in some embodiments, the clamp assembly 100 includes one or more teeth 115 that extend proximally. The teeth 115 can have one or more sharp or pointed ends or, in some embodiments, barbs (see FIG. 5), that can penetrate into or otherwise engage the vessel wall 53. The teeth 115 can comprise one or more of a variety of materials, including, for example, stainless steel, Nitinol, or the like.

As shown in FIG. 2, in the illustrated embodiment, the teeth 115 extend proximally from a ring or tubular structure 133, and the tubular structure 133 is coupled with the clamp tube 109 such that the tubular structure 133 is fixed relative thereto and moves therewith. As shown in FIGS. 5 and 6, one or more of the teeth 115 can be configured to flex outwardly. For example, in some embodiments, one or more of the teeth 115 can be bent outwardly or otherwise biased toward a radially expanded state during manufacture. The teeth 115 can be received within the anvil 104 into a compressed state when the clamp foot 110 and the anvil 104 are in close proximity. When the anvil 104 and the clamp foot 110 are separated to create or expand the gap 132, the teeth 115 (or a portion thereof) can emerge from a position within the anvil 104 so as to expand outwardly to their natural, preconditioned, or expanded state. Stated otherwise, movement of the anvil 104 and the clamp foot 110 away from each other can remove a restriction provided by the anvil 104 that maintains the teeth 115 in a constricted arrangement, thus permitting the teeth 115 to flex outwardly to their natural expanded configuration. In various embodiments, the teeth comprise a shape memory material or super elastic metal alloy, such as, for example, Nitinol.

In other embodiments, a position or orientation of the teeth 115 relative to either the anvil pull tube 106 or the clamp tube 109 may be substantially fixed such that the teeth do not expand or contract as the clamp assembly 100 is moved between the open and closed states. In still other embodiments, the clamp assembly 100 may be devoid of teeth 115. For example, other friction enhancing features may be applied to the anvil 104 and/or the clamp foot 110, and/or the shape and relative orientations of the anvil 104 and the clamp foot 110 can provide sufficient gripping of the vessel wall 53 throughout an anastomosis procedure.

With reference again to FIGS. 2, 5, and 6, in some embodiments, the tips of the teeth 115 are relatively close to the clamp foot 110 when the clamp foot 110 and the anvil 104 are in a closed or approximated orientation. Moving the clamp foot 110 and the anvil 104 to the open position so as to effect expansion of the teeth 115 can cause the tips of the teeth 115 to move away from the clamp foot 110 in a radial direction (e.g., away from a longitudinal axis of the assembly 100) and/or in an axial direction (e.g., distally). Such movement of the teeth 115 can provide access to sharpened ends thereof. The expanded configuration of the teeth 115 can facilitate improved capture of the vessel wall 53 in the gap 132 between the anvil 104 and the clamp foot 110.

In other embodiments, the teeth 115 are fixed relative to the anvil 104. For example, in some embodiments the tubular structure 133 is attached to the anvil 104. The teeth 115 can define an inner periphery that is sized and shaped to receive an outer periphery of the clamp foot 110. For example, in some embodiments, the teeth 115 form a ring around the clamp foot 110 when the clamp foot 110 and the anvil 104 are in the closed or approximated state. When the clamp foot 110 and the anvil 104 are moved to the separated or open state so as to create the gap 132, the teeth 115 can maintain their original position relative to the anvil 104. Due to the greater exposure of the tips of the teeth 115, such movement can allow the teeth 115 to grip, capture, embed within, or otherwise hold a portion of the vessel wall 53 that is introduced into the gap 132 (e.g., the movement can provide access to tips of the teeth 115). Certain of such embodiments can be formed by attaching the tubular structure 133 in FIG. 2 to the anvil 104 rather than the clamp foot body 137, by slightly reducing the diameter of the clamp foot 110, and by extending the teeth 115 in a proximal direction such that the tips thereof encircle the clamp foot 110 when the clamp assembly 100 is in the closed state.

With reference to FIG. 2, in some embodiments, one or more holes or openings 112 through a wall of the clamp tube 109 can be provided. The openings 112 can extend through the clamp foot body 137 at a position distal of the clamp foot 110, and may be sized to permit bodily fluids (e.g., blood) or air to flow from the outside of the clamp tube 109 into the channel 113 between the anvil pull member 106 and the clamp tube 109. As shown in FIG. 4, at least a portion of the one or more openings 112 can be exposed (e.g., can be positioned within the gap 132) when the clamp assembly 100 is in the closed or approximated orientation. In some embodiments, the notches 134 in the clamp foot 110 can improve blood flow into the one or more openings 112. In other embodiments, the one or more openings 112 can be fully enclosed by the anvil 104 when the clamp assembly 100 is in the closed or approximated position. For example, this can be the case for certain of the embodiments described at the end of the previous paragraph, in which the tips of the teeth 115 encircle the clamp foot 110 when the clamp assembly 100 is in the closed state. In such embodiments, the notches 134 can provide a channel through which blood can flow from outside of the anvil 104 and the clamp foot 110 into the openings 112 and the channel 113.

With reference to FIG. 3, the channel 113 can extend to a proximal end of the clamp tube 109. In some embodiments, a sealing member 136 seals the proximal end of the channel 113. The sealing member 136 can be configured to provide a substantially liquid-tight or airtight seal while permitting relative movement of the clamp tube 109 and the anvil pull member 106. In the illustrated embodiment, the sealing member 136 comprises an o-ring.

One or more openings 114 in the clamp tube 109 can provide fluid communication between the channel 113 and a bodily fluid marker chamber 129 defined by the housing 135. The bodily fluid marker chamber 129 can be in fluid communication with a tube 74 having a connector 75 at an end thereof. The tube 74 can define a channel 72 that provides fluid communication between the bodily fluid marker chamber 129 and the connector 75. In some embodiments, sealing devices 128, such as, for example, o-rings, can create a seal around the clamp tube 109 at either side of the holes 114, and thus can prevent the blood or air from leaking from the bodily fluid marker chamber 129 into other portions of the channel 131 defined by the housing 135.

A bodily fluid, such as blood from a blood vessel, or air can be drawn to the exterior of the clamp actuation device 120 via the channel 113, the bodily fluid marker chamber 129, and the tube channel 72 so as to be visualized as a bodily fluid marker by a clinician. Such bodily fluid marker visualization can be advantageous when the location of the anvil 104 and the clamp foot 110 relative to a vessel wall is not visually observable by a user of the clamp assembly 100, as the skin of a patient or the vessel wall itself may obscure the location of the anvil 104 and the clamp foot 110. In such cases, the bodily fluid marker can function as a method to confirm the location of the anvil 104 and the clamp foot 110, as further discussed below.

In certain embodiments, in order to draw blood (in the case of a blood vessel) or some other bodily fluid for visualization, negative pressure can be applied to the channel 113 via the connector 75. For example, a syringe (not shown) can be connected to the connector 75 and a plunger of the syringe withdrawn in order to create negative pressure sufficient to draw blood through the bodily fluid marker chamber 129 for visualization. Other suitable methods for applying negative pressure via the connector 75 so as to visualize the presence of blood or air in the vicinity of the clamp foot 110 are also possible.

Methods for clamping the vessel wall 53 can include positioning the guidewire 103 within a target blood vessel 51 utilizing a well known micropuncture technique for vascular access. The insertion tract around the guidewire 103 can be dilated (e.g., serially dilated). As shown in FIG. 4, the clamp assembly 100 can then be passed over a proximal end of the guidewire 103 via the lumen 102. The clamp assembly 100 can be inserted through the skin tissue 52, the vessel wall 53 and into the lumen 52 of the target vessel 51 over the guidewire 103.

In certain embodiments, it can be desirable for the clamp assembly 100 to be in the closed or approximated state during its insertion into the blood vessel 51. As previously discussed, the tips of the teeth 115 can be relatively inaccessible when the clamp assembly 100 is closed. The tips thus are less likely to inadvertently capture the tissue 52 as the clamp assembly 100 is inserted into the blood vessel 51. In some embodiments, it can be desirable to ensure that the clamp assembly 100 remains closed during insertion. In certain of such embodiments, the clamp foot 110 can be inserted into the blood vessel 51 as the clamp assembly 100 remains closed during the insertion. Although the clamp foot 110 can have a larger diameter than the portion of the clamp tube 109 that is proximal thereto, the vessel wall 53 can be sufficiently resilient to close around the clamp tube 109 after the clamp foot 110 has passed through the wall 53 into the vessel 51, as shown in FIG. 4. The interface between the vessel wall 53 and the clamp tube 109 thus can substantially prevent egress of blood from the vessel 51.

With continued reference to FIG. 4, when the clamp foot 110 is inside the vessel lumen 50, blood can be withdrawn from the vessel 51 through the openings 112. Withdrawal of blood, rather than air, can indicate that the clamp assembly 100 is in a desirable position for opening. The clamp actuator 121 can then be moved to the open position, thereby moving the anvil 104 distally away from the clamp foot 110. The gap 132 thus can be enlarged (as in the illustrated embodiment) or created, and access to the teeth 115 can be provided.

In some embodiments, it is possible to properly position the clamp assembly 100 for clamping the vessel wall 53 without fully, or even partially, inserting the clamp foot 110 through the vessel wall 53 or into the vessel lumen 50. For example, in the illustrated embodiment, the openings 112 can be within the lumen 50 when a distal surface of the clamp foot 110 is substantially even with an inner surface of the vessel wall 53. At such a stage of insertion of the clamp assembly 100, blood can be withdrawn from the vessel 51 via the channel 113 so as to indicate that the clamp assembly 100 can be moved to the open configuration.

With reference to FIGS. 5 and 6, the clamp assembly 100 can remain in the open configuration and can be moved proximally so as to pull the clamp foot 110 and the anvil 104 toward the vessel wall 53. In some embodiments, once the clamp foot 110 has passed through the vessel wall 53 in a proximal direction, the vessel wall 53 can resiliently close around the clamp foot body 137 within the region of the gap 132. In some embodiments, it can be desirable for the clamp foot body 137 to have a slightly enlarged diameter of sufficient size to allow the vessel wall 53 to resiliently close in around and contact it around substantially the full periphery of the clamp foot body 137. This can aid in properly centering and positioning the vessel wall 53 for subsequent cutting. Additional proximal movement of the clamp assembly 100 can cause the vessel wall 53 to be captured or otherwise retained on the teeth 115. Such capturing of the vessel wall 53 can be sensed by an operator of the clamp actuation device 120 as an increased resistance to proximal movement of the clamp assembly 100, which increased resistance can be provided by the blood vessel 51. In some embodiments, another indicator that the vessel wall 53 has been captured can be the stoppage of blood flow through the channel 113 and/or an initiation of air flow through the channel 113, which can occur if the openings 112 are sufficiently small and/or are spaced sufficiently far from the anvil 104 so as to no longer be positioned within the lumen 50 of the vessel 51 when the vessel wall 53 has been captured.

Figure 7:
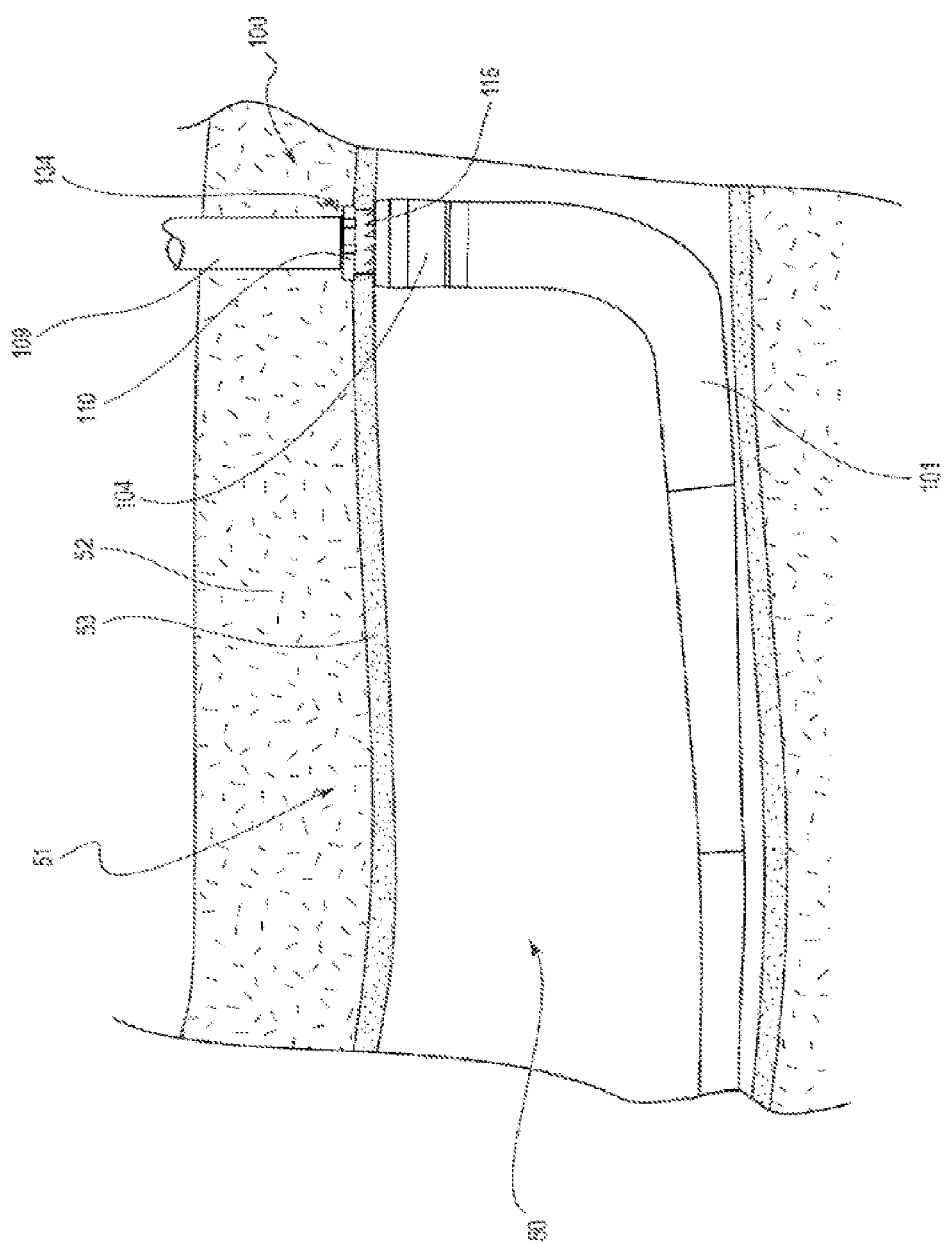
FIG. 7 is a perspective view of a portion of the clamp assembly of FIG. 1 shown in a closed configuration with the wall of the blood vessel clamped between the clamp foot and the anvil.
Figure 8:
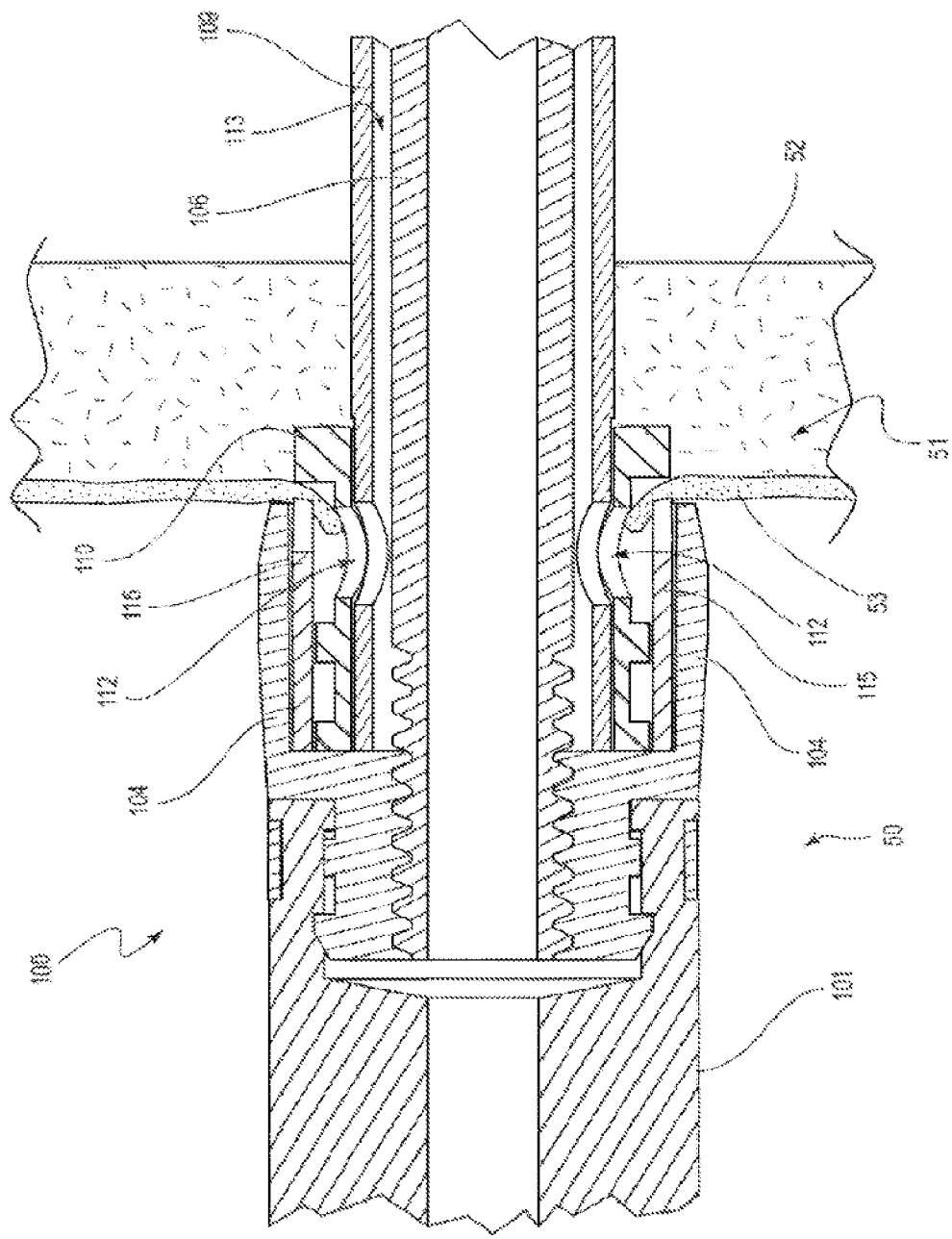
FIG. 8 is a cross-sectional view of a portion of the clamp assembly of FIG. 7.

With reference to FIGS. 7 and 8, once the vessel wall 53 has been captured on the teeth 115, the clamp actuator 121 (see FIG. 3) can be moved to the closed state, thereby permitting the anvil 104 to move proximally under the bias provided by the biasing member 111 (see FIG. 3) toward the clamp foot 110. As the anvil 104 sheaths increasingly greater portions of the teeth 115, the teeth 115 can be move or rotated radially inward so as to return to a constricted configuration. As a result, a portion of the vessel wall 53 that was captured within a periphery defined by the sharpened tips of the teeth 115 can be constricted or drawn inward toward a longitudinal axis of the clamp assembly 100. As previously discussed, in other embodiments, the teeth 115 do not expand and contract as the clamp assembly 100 is opened and closed, respectively, such that a periphery of a captured portion of the vessel wall 53 may remain substantially constant during closure of the clamp assembly 100. In either case, closure of the clamp assembly 100 can be clamped, or securely hold, the vessel wall 53 between the anvil 104 and the clamp foot 110.

In some embodiments, the guide wire 103 is removed from the vessel 51 through the clamp assembly 100 once the vessel wall 53 has been clamped. In other embodiments, the guide wire 103 can be removed at some other stage of an anastomosis procedure. With reference to FIG. 3, once the vessel wall 53 has been clamped, the actuator 125 can be depressed and the clamp actuation device 120 can be moved in a proximal direction and removed from the clamp assembly 100. As further discussed below, the clamp actuation device 120 can be replaced with an anastomosis actuation device 300 for addition stages of an anastomosis procedure.

Figure 9:
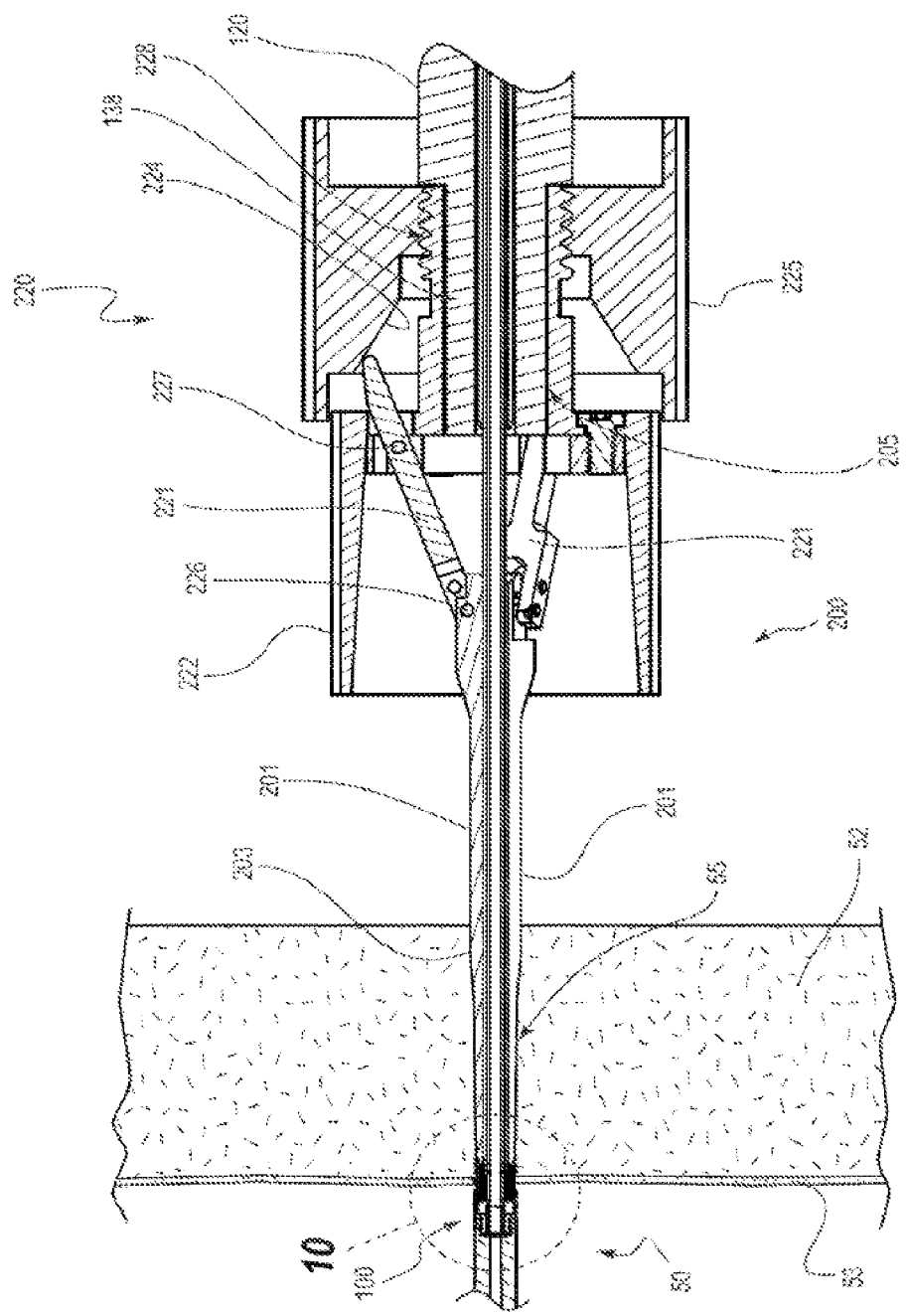
FIG. 9 is a cross-sectional view of an embodiment of a tract dilator assembly in a non-expanded or constricted state.

With reference to FIG. 9, in some embodiments, a dilation device, tract dilation assembly, or tract dilator 200 can be positioned over the clamp assembly 100. In some embodiments, the tract dilator 200 can be positioned over the clamp assembly 100 after the vessel wall 53 has been clamped and after the clamp actuation device 120 has been removed from the clamp assembly 100. Such an arrangement is illustrated in FIGS. 1-8, as the tract dilator 200 is not present during the clamping of the blood vessel wall 53.

Figure 10:
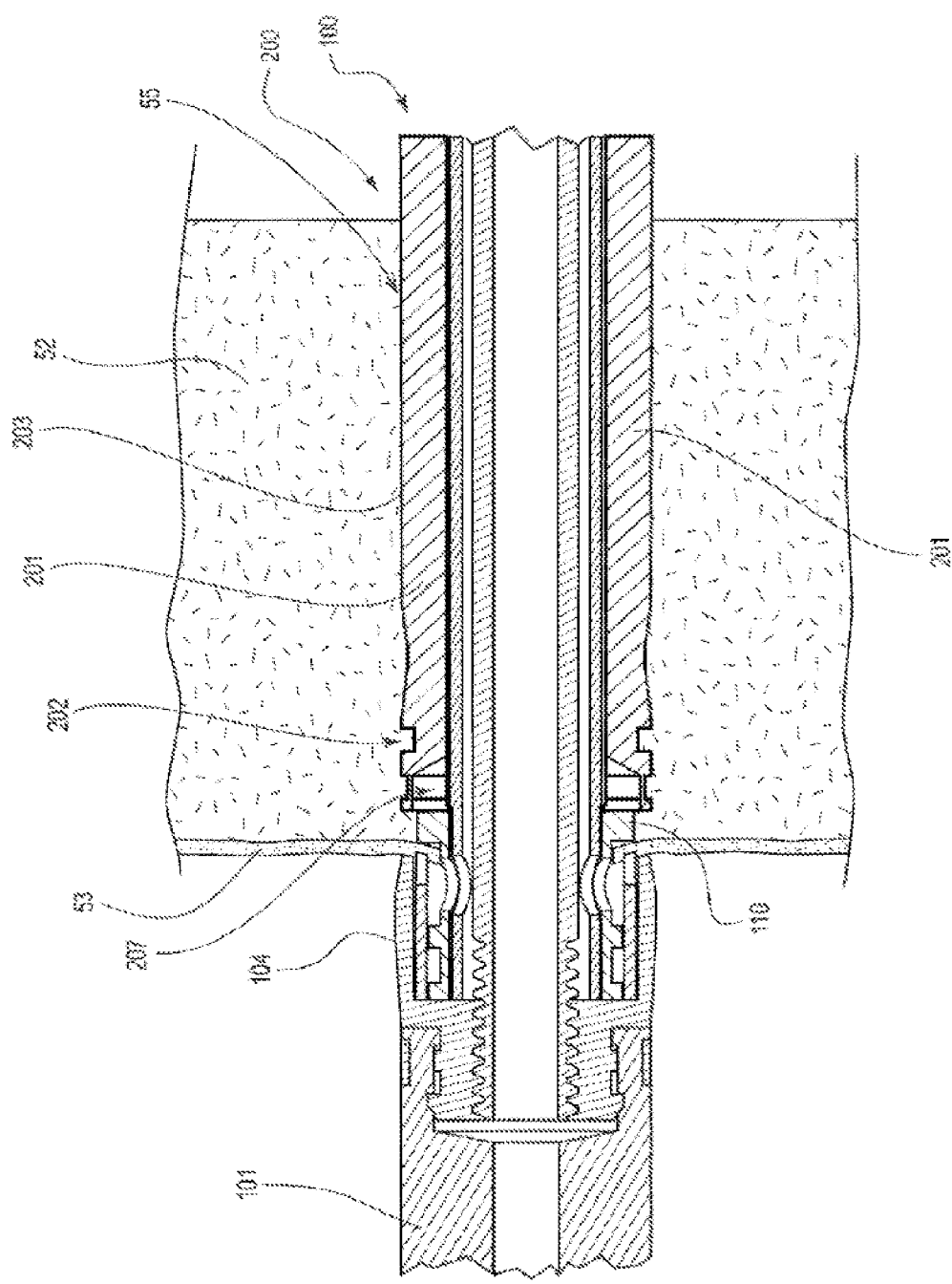
FIG. 10 is a cross-sectional view of a distal region of the tract dilator of FIG. 9.
Figure 11:
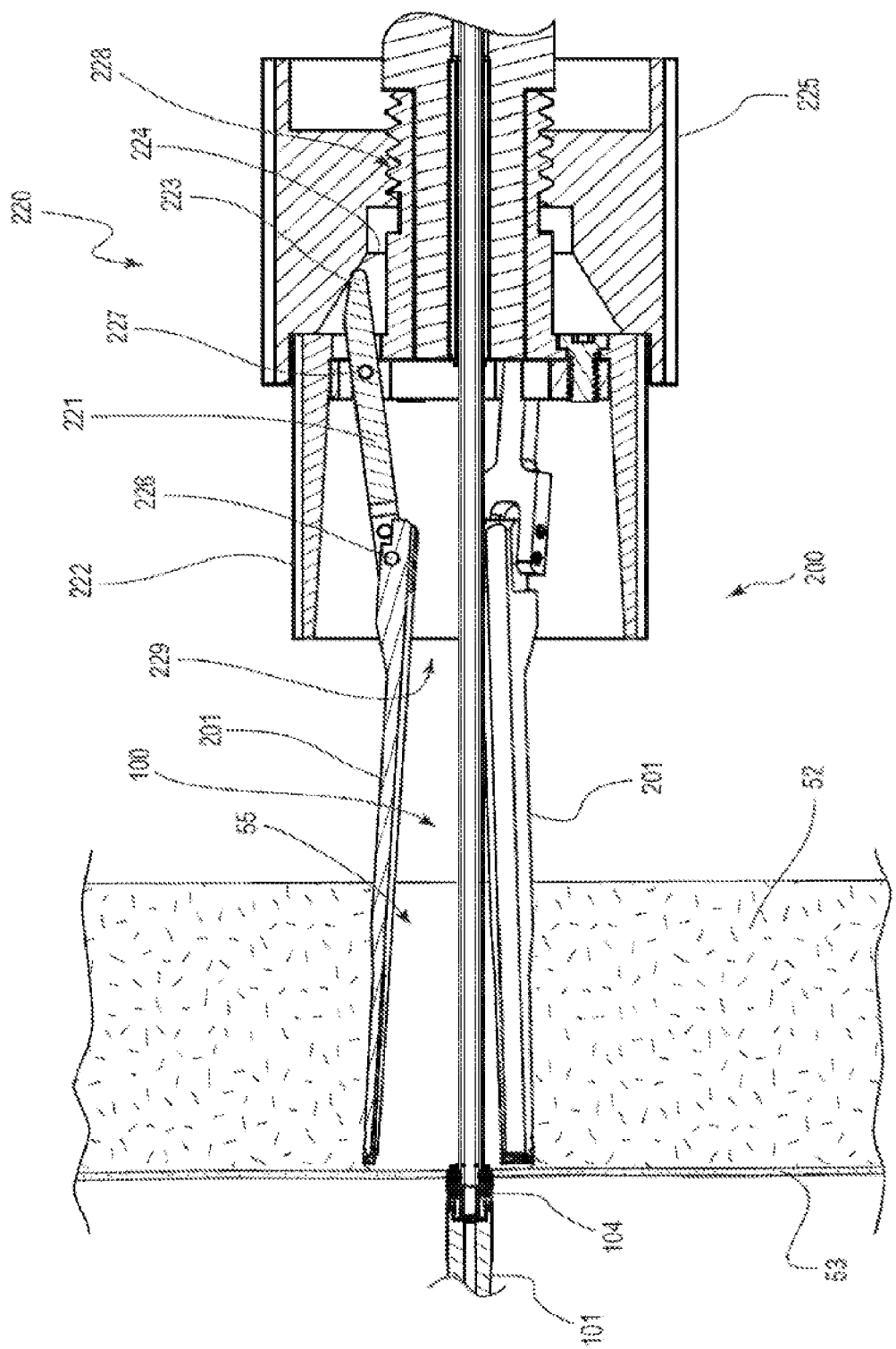
FIG. 11 is a cross-sectional view of the distal region of the tract dilator assembly of FIG. 9 shown in an expanded state.

In other embodiments, such as the embodiment illustrated in FIGS. 9-11, both the clamp actuation device 120 and the tract dilator 200 can be positioned over the actuation assembly 100 during the clamping of the vessel wall 53. The tract dilator 200 can be at a position that is distal of the clamp actuation device 120. In some embodiments, the clamp actuation device 120 is separable from the tract dilator 200, whereas in other embodiments, the tract dilator 200 and the clamp tube handle 120 are securely attached to each other, or can define an integral unit. With reference to FIG. 9, in the illustrated embodiment, the tract dilator 200 defines an alignment channel 205 sized and shaped to receive therein a distal nose 138 of the clamp actuation device 120 (see also FIG. 1). The distal nose 138 and the alignment channel 205 can cooperate to define a longitudinal axis that is common to both the clamp actuation device 120 and the tract dilator 200. The clamp actuation device 120 can be friction fit to or otherwise selectively or temporarily coupled with the tract dilator 200.

The tract dilator 200 can include one or more legs 201 that are configured to move from a closed, contracted, or constricted state (e.g., FIGS. 9 and 10) to an open or expanded state (e.g., FIG. 11) in order to expand the size of an insertion tract 55 through the skin tissue 52 and thereby provide greater access to the blood vessel 51. In the illustrated embodiment, the tract dilator 200 includes three legs 201, which are shown in the various views of FIGS. 9-11. More or fewer legs 201 are possible. For example, in various embodiments, the tract dilator 200 includes two or more legs 201, three or more legs 201, four or more legs 201, or five or more legs 201.

With reference to FIGS. 9 and 10, when the legs 201 are in the closed or constricted state, they can extend substantially parallel to a longitudinal axis of the clamp assembly 100, and the distal ends thereof can be adjacent the clamp foot 110. As shown in FIG. 10, in some embodiments, the distal end of each leg 201 includes a recess or depression 207. Together, the depressions 207 can define a cavity at a proximal end of the clamp foot 110. The cavity can be sized to receive the clamp foot 110 therein such that the distal ends of the legs 201 can more closely approach or contact the vessel wall 53, which can aid in displacement of adventitia from the vessel wall 53 when the legs are moved to the expanded state. The distal ends of the legs 201 can define notches 202 or other suitable engaging features, which can catch or grip the tissue 52 as the legs are radially expanded and can aid in securing the dilation device 200 in a substantially fixed position during an anastomosis procedure.

An outer surface 203 of the legs 201 can be radiused, and the legs 201 can fit closely together to form a substantially smooth or substantially continuous structure that surrounds or encircles the clamp assembly 100 when the legs 201 are in the constricted state. A distal portion of the structure formed by the legs 201 can have a diameter that is about the same size as the diameter of the anvil 104, in some embodiments, or slightly smaller than the diameter of the anvil 104 in other embodiments, which can facilitate insertion of the legs 201 into the skin tissue 52. In some embodiments, the distal ends of the legs 201 can be inserted into the vessel lumen during the initial insertion of the clamp assembly 100 into the vessel. Accordingly, the size and shape of the distal ends of the legs 201 can facilitate such insertion into the vessel. Insertion of the distal ends of the legs 201 can aid in positioning the legs 201 sufficiently close to the vessel wall to clear away the skin tissue 52.

The diameter at the distal end of the legs 201 can be smaller than a diameter than the proximal portion thereof. For example, in some embodiments, an outer surface 203 of the legs 201 can be tapered outward such that the legs 201 increase in thickness from a distal end to a proximal end thereof. The larger thickness of the proximal portion of the legs 201 can increase their flex strength. The legs 201 can be made from any suitable rigid material, such as, for example, stainless steel.

In some embodiments, a thin tearable sheath (not shown) can surround the distal portion of the legs. The sheath can prevent or inhibit inadvertent radial expansion of the legs 201 and can facilitate a smooth insertion of the legs 201 into the insertion tract 55. The sheath can be made from heat shrink tubing. In some embodiments, the legs 201 can be coated with a lubricant, such as, for example, a hydrophilic polymer or silicone oil, to facilitate their smooth insertion through the insertion tract 55.

With reference to FIGS. 9 and 11, in some embodiments, the tract dilator 200 comprises a dilation actuator 220 configured to move the legs 201 between the constricted state and the expanded state. Any suitable form of dilation actuator 220 may be used to alter the orientation of the legs 201. In the illustrated embodiment, a distal end of each leg 201 is pivotally coupled to an arm 221 at a pivot point 226, and each arm 221 is pivotally coupled to a distal housing 222 at a pivot point 227. Also coupled to the distal housing 222 is a proximal housing 225. The distal and proximal housings 222, 225 are coupled to each other via a threaded interface 228 so as to be able to rotate and translate relative to each other about and along a central axis of the tract dilator 200. In some embodiments, the distal and proximal housings 222, 225 are sized and shaped to be gripped as handles, and can include surface features, such as grooves, to aid with the gripping. The proximal housing 225 can include a cam surface 224 that tapers inwardly toward a central axis of the dilator device 200 in a proximal direction.

As shown in FIG. 9, when the legs 203 are in the constricted state, the proximal ends of the arms 221, which can be rounded or radiused, contact a distal end of the cam surface 224. The proximal housing 225 can be rotated about the central axis of the dilator device 200 so as to be advanced distally along the threaded interface 228, which likewise advances the cam surface 224 in a distal direction. As shown in FIG. 11, the decreasing diameter or inward slope of the cam surface 224 urges the proximal ends of the arms 221 radially inward, thereby causing the arms 221 to pivot about the pivot points 227 such that the distal ends of the arms 221 move radially outwardly. The outward movement of the distal ends of the arms 221 can urge the legs 201 radially outwardly, thereby compressing or otherwise moving the skin tissue 52 outwardly to expand the insertion tract 55. The skin tissue 52 can resist the expansion of the insertion tract 55, thereby applying an inward force on the distal ends of the legs 201. This inward force can cause the legs 201 to pivot somewhat about the pivot point 226. As a result of this latter pivoting, the insertion tract 55 can have a more uniform cross sectional area (in a direction transverse to a longitudinal axis of the clamp assembly 100) than it would otherwise.

A geometry of the expanded insertion tract 55 can depend on the number and configuration of the legs 201. In the illustrated embodiment, the three legs 201 form an expanded insertion tract 55 shaped substantially as the base of a triangular pyramid. In other embodiments, the expanded insertion tract 55 can resemble the base of a square pyramid, such as when four legs 201 are used. In still further embodiments, use of additional legs 201 can result in the expanded insertion tract 55 more closely resembling a base of a cone. As shown in FIG. 11, the insertion tract 55 can be wider at a distal end of the legs 201 (e.g., at or near the vessel wall 53) than at a more proximal portion thereof. In various embodiments, a maximum diameter of the expanded insertion tract 55 can be between about 12 French and about 30 French, no less than about 12 French, no less than about 15 French, no less than about 20 French, or no less than about 30 French.

Movement of the legs 201 to the expanded orientation can distance the proximal ends of the legs 201 from the clamp assembly 100, which can open an insertion corridor 229 between the legs 201 and the clamp assembly 100. As discussed further below, a periphery of the corridor 229, which can be defined by the proximal ends of the legs 201, can be sufficiently large to allow passage of a distal end of an anastomosis actuation device 300 (see FIG. 12) through it toward the vessel wall 53.

In use, embodiments of the tract dilator 200 can be positioned over the clamp assembly 100 such that the distal end of the legs 201 are adjacent the clamp foot 110. The clamp assembly 100 can be inserted into the vessel 51 and the vessel wall 53 can be clamped in a manner described above. Due to the positioning of the tract dilator 200 relative to the clamp assembly 100, insertion of the clamp assembly 100 into the vessel 51 and insertion of the tract dilator 200 into the skin tissue 52 can take place at the same time or during the same stage. As previously discussed, however, in other embodiments, the tract dilator 200 can be inserted into the skin tissue 52 subsequent to clamping the vessel wall 53 via the clamp assembly 100. In either case, when the legs 201 are within the insertion tract 55, the dilation actuator 220 can be actuated. For example, as previously discussed, the proximal housing 225 can be rotated relative to the distal housing 222, thereby causing the cam surface 224 to move distally and drive the proximal ends of the arms 221 radially inward and the distal ends of the legs 201 radially outward to dilate the insertion tract 55.

Figure 12:
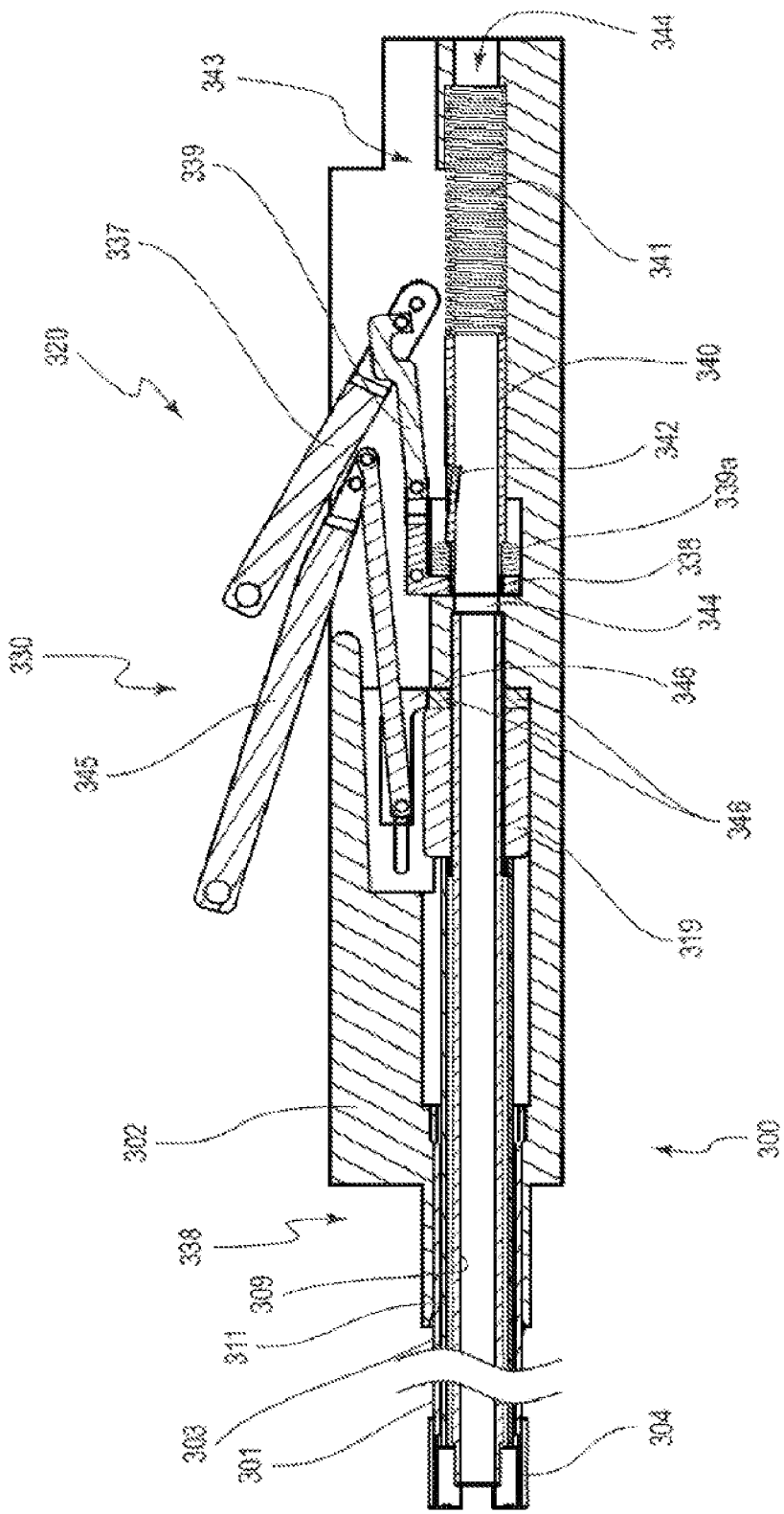
FIG. 12 is a cross-sectional view of an embodiment of an anastomosis actuation device.
Figure 40:
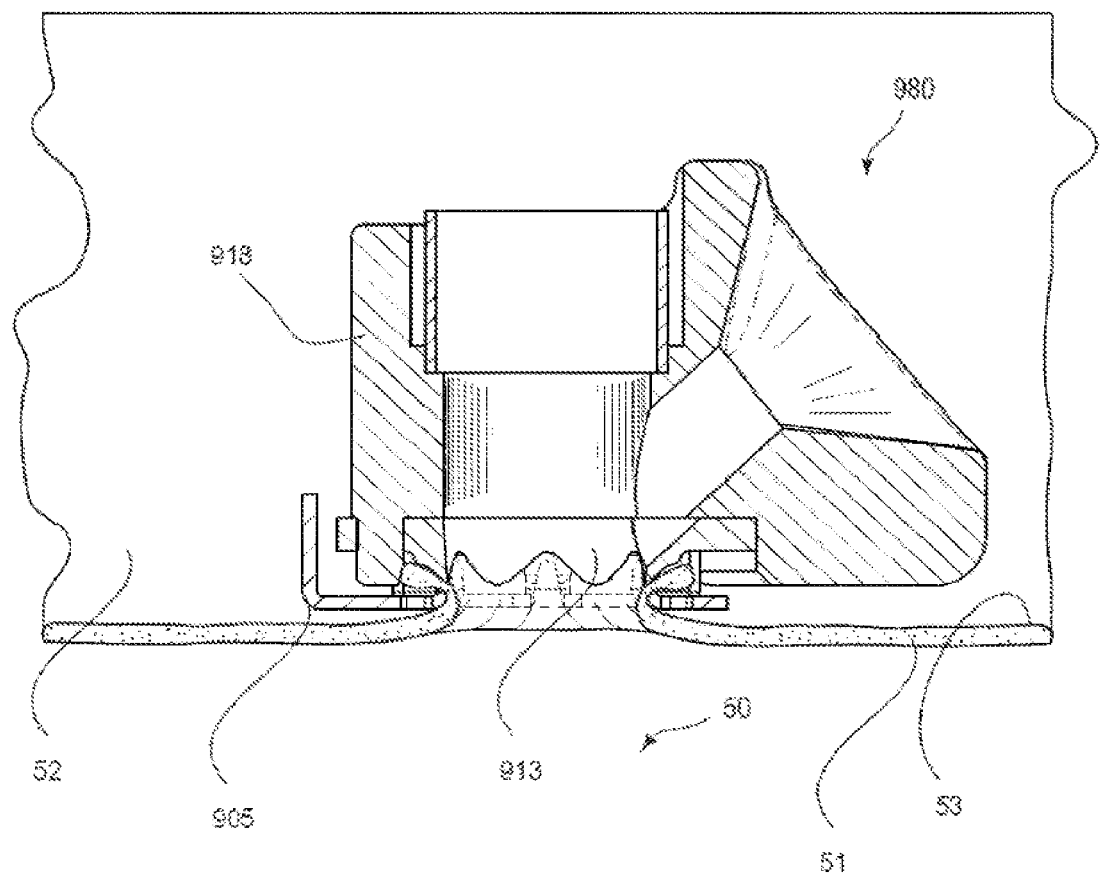
FIG. 40 is a cross-sectional view of an embodiment of a fully implanted access port anastomosed to a blood vessel.

In certain embodiments, once the insertion tract 55 is dilated, the clamp actuation device 120 can be removed from the clamp assembly 100 (in a manner such as discussed above) and replaced with an anastomosis actuation device 300, an embodiment of which is illustrated in FIG. 12. The anastomosis actuation device 300 can be used to attach an access device to the blood vessel 51. The access device can comprise a conduit 318 that is anastomosed to the blood vessel 51 in an end-to-side anastomosis, and the conduit 318 can extend through the skin tissue 52 so as to be accessible from a position outside of the patient once the anastomosis procedure is complete (see FIG. 17). In other embodiments, the anastomosis actuation device 300 can be configured to implant an access device, such as an anastomosis implant 918, beneath or within the skin tissue 52 (see FIG. 40).

With reference to FIG. 12, in certain embodiments, the anastomosis actuation device 300 comprises a housing 302, which can be sized and shaped to be gripped as a handle. The housing 302 can include a distal nose 338, which can be configured substantially identically to the distal nose 138 of the clamp actuation device 120. Accordingly, the distal nose 338 of the anastomosis actuation device 300 can be received within the alignment channel 205 of the tract dilator 200 in any suitable manner, such as those described above with respect to the distal nose 138 of the clamp actuation device 120 (see FIG. 9).

An adapter tube 303 can be fixedly attached to the housing 302 so as to be substantially stationary relative thereto. An approximation tube or actuator tube 311 can be positioned within the adapter tube 303, and may be coaxial therewith. The actuator tube 311 can be configured to move relative to the adapter tube 303. For example, the actuator tube 311 can be configured to move from an initial or un-actuated position to one or more distal positions, such as a region of approximation and an ejection position, which are discussed further below. Depending on the relative inner diameter of the adapter tube 303 and the outer diameter of the actuator tube 311, the tubes 303, 311 can be in sliding engagement with each other, or they may be sufficiently radially spaced from one another to move relative to each other without frictional engagement.

A cutter tube 309 can be positioned within the actuator tube 311. In the illustrated embodiment, the cutter tube 309 is fixedly attached to the housing 302 at its proximal end. A distal end of the cutter tube 309 can have a sharpened blade 310, which is discussed further below (see also, e.g., FIG. 16). In some embodiments, the blade 310 extends distally beyond a distal end of the adapter tube 303. However, a retaining adapter 304, which can also be referred to as a temporary retainer, can be fixedly attached to the distal end of the adapter tube 303, and the retaining adapter 304 thus can extend distally beyond the blade 310 so as to substantially shield or encircle the blade 310. A conduit 318 (see FIG. 15) can be positioned within the adapter tube 303, and further, can be positioned between the actuator tube 311 and the cutter tube 309 (see FIG. 16). However, for clarity, the conduit 318 is not shown in FIG. 12. Likewise, the clamp assembly 100 can be received within the anastomosis actuation device 300, but is not shown in FIG. 12 for the sake of clarity. In the illustrated embodiment, the clamp assembly 100 can be positioned within the cutter tube 309 and can extend through a channel 344 defined by the housing 302.

The anastomosis actuation device 300 can include a cutter actuator 320, which can include any suitable arrangement of structures configured to cooperate to effect movement of a clutch coupler or clutch coupling tube 340. In the illustrated embodiment, the cutter actuator 320 includes an outer lever 337 that is pivotally coupled to one or more inner links 339. A locking or compression member 339a, such as one or more Bellville washers, can be positioned between an inner link 339 and a distal end of the clutch coupling tube 340. A biasing device 341, such as a compression spring, can be positioned at a proximal end of the clutch coupling tube 340. The biasing device 341 can be secured to or otherwise contact the housing 302 at its proximal end. The clutch coupling tube 340 can include a catch member 342, which can include a living hinge or a biased finger that extends radially inwardly toward a longitudinal axis of the clutch coupling tube 340.

As previously discussed, the anastomosis actuation device 300 can replace the clamp actuation device 120 once the clamp assembly 100 has been coupled with a vessel wall 53. The anastomosis actuation device 300 can be advanced in a distal direction over the clamp assembly 100 until the nose 338 of the housing 302 is received within the alignment channel 205 of the tract dilator 200 and until the catch member 342 of the clutch coupling tube 340 is received within a recess of the clutch 108 that is defined between the proximal and distal shoulders 119, 124 thereof (see, e.g., FIG. 3).

When the anastomosis actuation device 300 is coupled to the clamp assembly 100, the cutter actuator 320 can be moved from an un-actuated or resting state to a cutting, embedding, or actuated state. In the illustrated embodiment, the cutter actuator 320 is in the resting state when the outer lever 337 is in a forward or distal position. The cutter actuator 320 can be moved to the actuated state by rotating the outer lever 337 in a proximal direction. In the illustrated embodiment, the housing 302 defines a channel 343 at a proximal end thereof which can receive the outer lever 337. Accordingly, the outer lever 337 can be substantially parallel to a longitudinal axis of the clamp assembly 100 when the cutter actuator 320 is actuated.

Movement of the cutter actuator 320 to the actuated state can cause the clutch coupling tube 340 to move proximally against a distally directed bias of the biasing member 341. In some embodiments, the cutter actuator 320 can be locked or selectively maintained in the actuated position. For example, in the illustrated embodiment, when the cutter actuator 320 is in the actuated state, the nearly parallel alignment of the outer lever 320 with the axially directed force of the biasing member 341 can reduce or eliminate any torque on the outer lever 337 that might otherwise be provided by the links 339, which would tend to urge the outer lever 337 to move in a distal direction. Any other or additional suitable locking mechanism can be employed, such as, for example, one or more of a detent and a latch.

The anastomosis actuation device 300 can include an approximation and ejection actuator 330, also referred to as an approximation actuator 330, which can include any suitable arrangement of structures configured to cooperate to effect movement of a clutch 319. In the illustrated embodiment, the approximation actuator 330 includes an outer lever 345 that is pivotally coupled to one or more inner links 346. At least one of the inner links 346 can contact the clutch 319 so as to move it in a distal direction. In the illustrated embodiment, the clutch 319 defines a central bore through which the cutter tube 309 extends, and the clutch 319 is configured to translate over the cutter tube 309.

The approximation actuator 330 can be moved from an un-actuated or resting state to an approximation stage, region or state, and further, can be moved from the approximation state to an ejection state. In some embodiments, transition from one state to another can be smooth or continuous, whereas in other embodiments, the different operational states can be discreet from each other (e.g., the outer lever 345 may transition through one or more detents). In the illustrated embodiment, the approximation actuator 330 is in the resting state when the outer lever 345 is in a forward or distal position. The cutter actuator 320 can be moved to the approximation state by rotating the outer lever 345 in a proximal direction. In the illustrated embodiment, the approximation state may first be reached when the outer lever 345 is at approximately a right angle relative to a longitudinal axis of the actuator tube 311, or when a distal end of the clutch 319 first contacts the actuator tube 311 and begins to move it in a distal direction. The cutter actuator 320 can remain in the approximation state as the outer lever 345 is rotated proximally through additional angles and the actuator tube 311 is moved distally. The approximation actuator 330 can transition to the ejection state when the outer lever 345 is proximally rotated to an even greater extent such that the actuator tube 311 is moved distally to an even greater extent. Angular orientations and arrangements for the outer lever 345 other than those just described are also possible.

Figure 13:
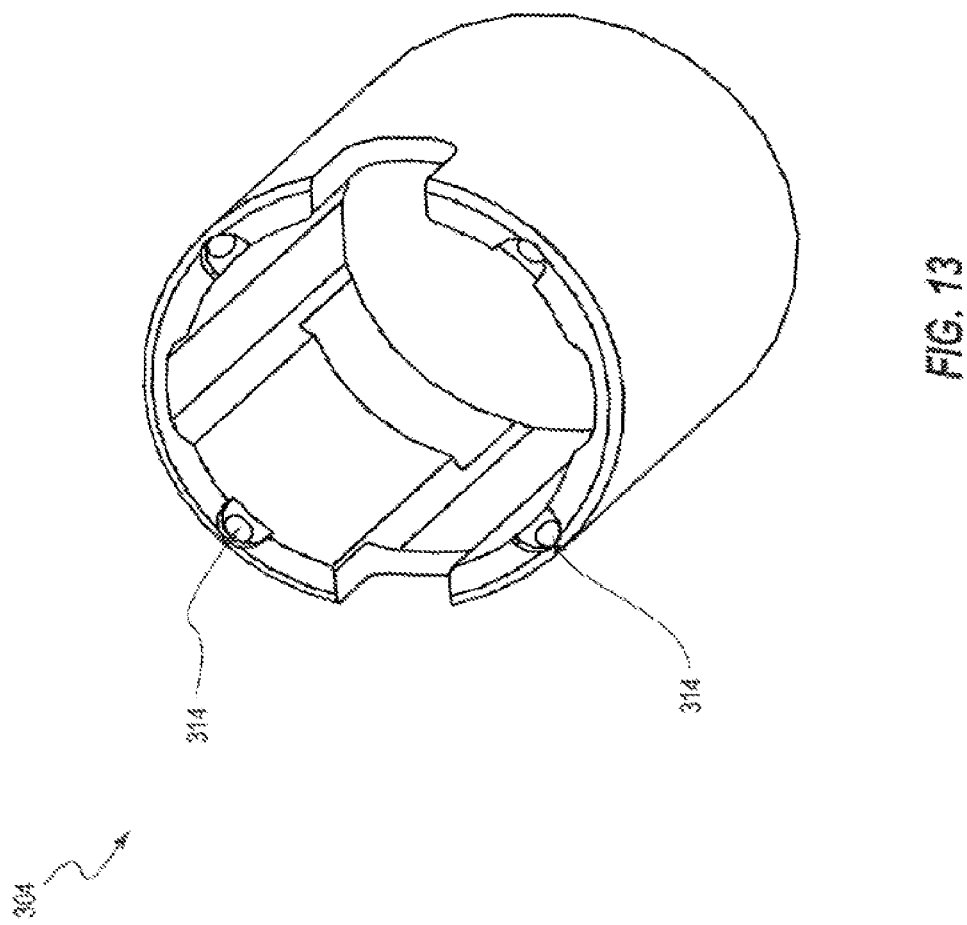
FIG. 13 is a perspective view of an embodiment of a retention adapter.

With reference to FIG. 13, in certain embodiments, the retaining adapter 304 includes one or more retention channels 314. The retention channels 314 can extend proximally from a distal end of the retaining adapter 304, and may extend into a sidewall of the adapter. In the illustrated embodiment, the retaining adapter 304 includes four retention channels 314, although more or fewer retention channels 314 are possible.

Figure 14:
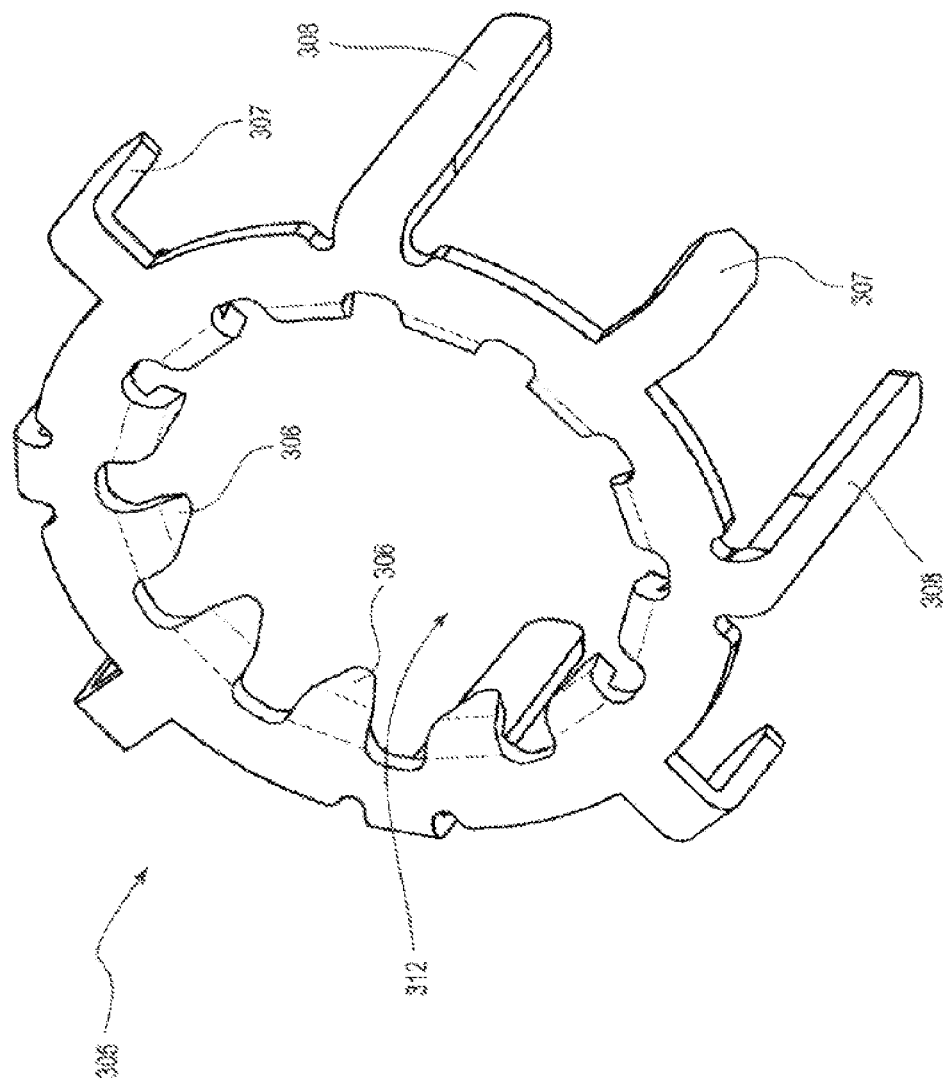
FIG. 14 is a perspective view of an embodiment of an anastomosis clip.

With reference to FIG. 14, in certain embodiments, an anastomosis clip 305 can be configured to couple with the retaining adapter 304 in a temporary manner. For example, the anastomosis clip 305 can include one or more retention legs 307 that can be received within the one or more retention channels 314 of the retaining adapter 304 in a friction-fit or interference-fit engagement. In the illustrated embodiment, the anastomosis clip 305 includes four retention legs 307, each of which can be received in a separate retention channel 314. More or fewer retention legs 307 are possible.

The anastomosis clip 305 can also include one or more connection legs 308. In some embodiments, the connection legs 308 are longer than the retention legs 307. Additionally, the connection legs 308 can be closer to an axial center of the anastomosis clip 305 than are the retention legs 307.

The anastomosis clip 305 can define a through hole 312 through which the clamp assembly 100, or at least a portion thereof, can pass. The anastomosis clip 305 can include one or more teeth 306 surrounding a through hole 312, which can extend proximally. The anastomosis clip 305 can be made from any suitable material, such as, for example, stainless steel. In some embodiments, the anastomosis clip 305 is coated with an antithrombogenic, anti-inflammatory, or cell proliferation inhibitor agent, such as heparin or rapamycin.

Figure 15:
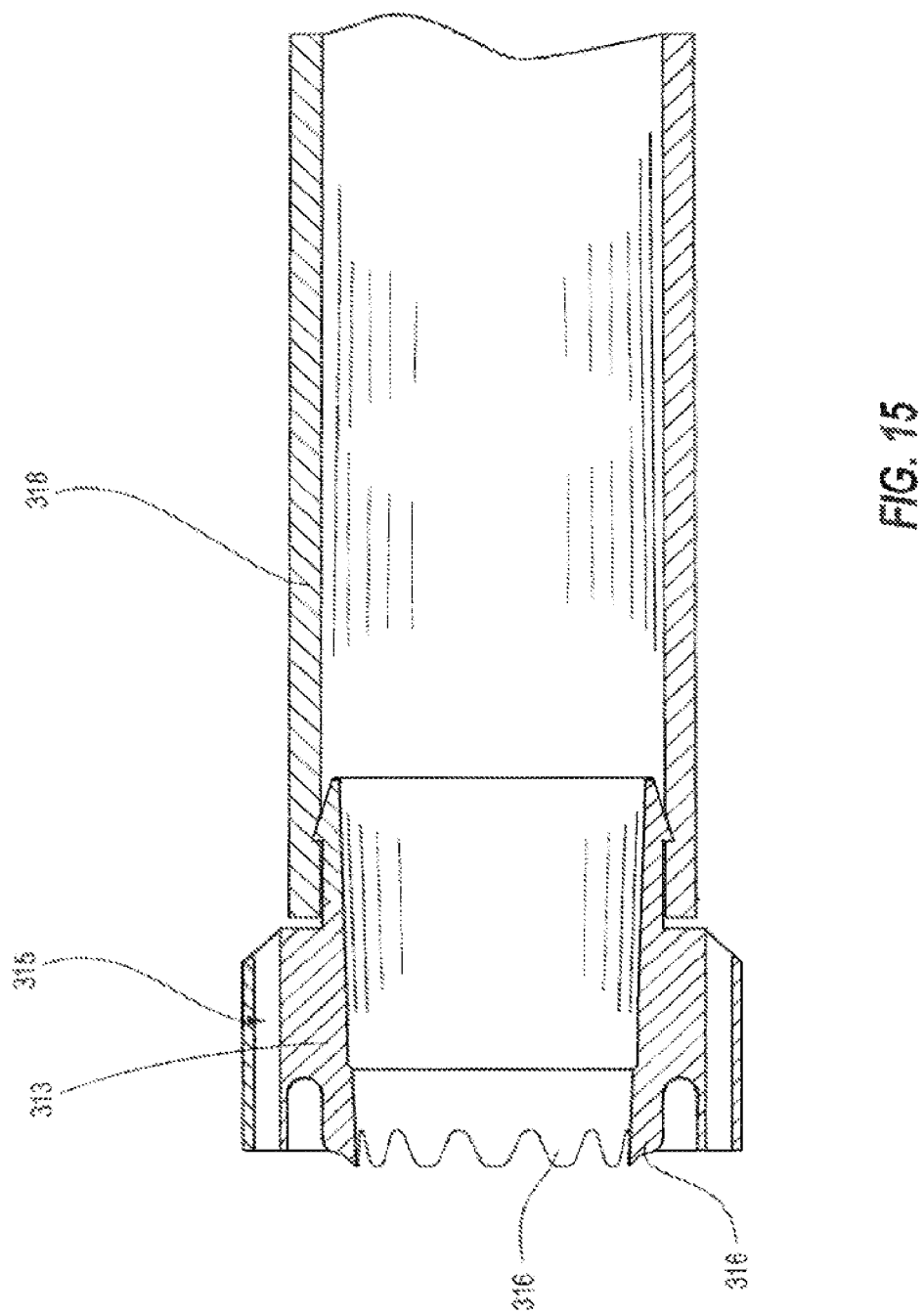
FIG. 15 is a cross-sectional view of an embodiment of an anastomosis conduit.

With reference to FIG. 15, in certain embodiments, an anastomotic implant or access device can include the conduit 318 through which blood may flow and/or through which blood access equipment may be passed after anastomosis of the device to a blood vessel 51. The conduit 318 can be substantially hollow, and can be made from any suitable material. For example, in various embodiments, the conduit 318 comprises one or more biocompatible materials, such as, for example, polytetrafluoroethylene (PTFE), polyurethane, silicone rubber, or other similar materials. The conduit 318, or at least a portion thereof, can be radiopaque. For example, one or more radiopaque agents, such as barium sulfate, bismuth trioxide, titanium dioxide, or the like can be dispersed throughout the conduit or can be formed into one or more stripes.

In certain embodiments, the anastomosis adapter or conduit adapter 313 is attached to a distal end of the conduit 318. The conduit adapter 313 can include one or more connection channels 315 therein or therethrough. In the illustrated embodiment, the connection channels 315 extend fully through a peripheral edge of the conduit adapter 313. In the illustrated embodiment, the conduit adapter 313 comprises four connection channels 315, each of which can receive one of the connection legs 308 of the anastomosis clip 305 in a friction-fit or interference-fit engagement. For example, in some embodiments, the connection channels 315 receive proximal tips of the connection legs 308 in an interference fit, and the strength of the interference fit is maintained or increased as the connection legs 308 are forced deeper into the connection channels 315. In other embodiments, the interference fit is created only when the connection legs 308 are fully inserted or nearly fully inserted into the connection channels 315. In either case, the interference fit can retain the anastomosis clip 305 and the conduit adapter 313 in a coupled arrangement, as further discussed below.

Figure 20:
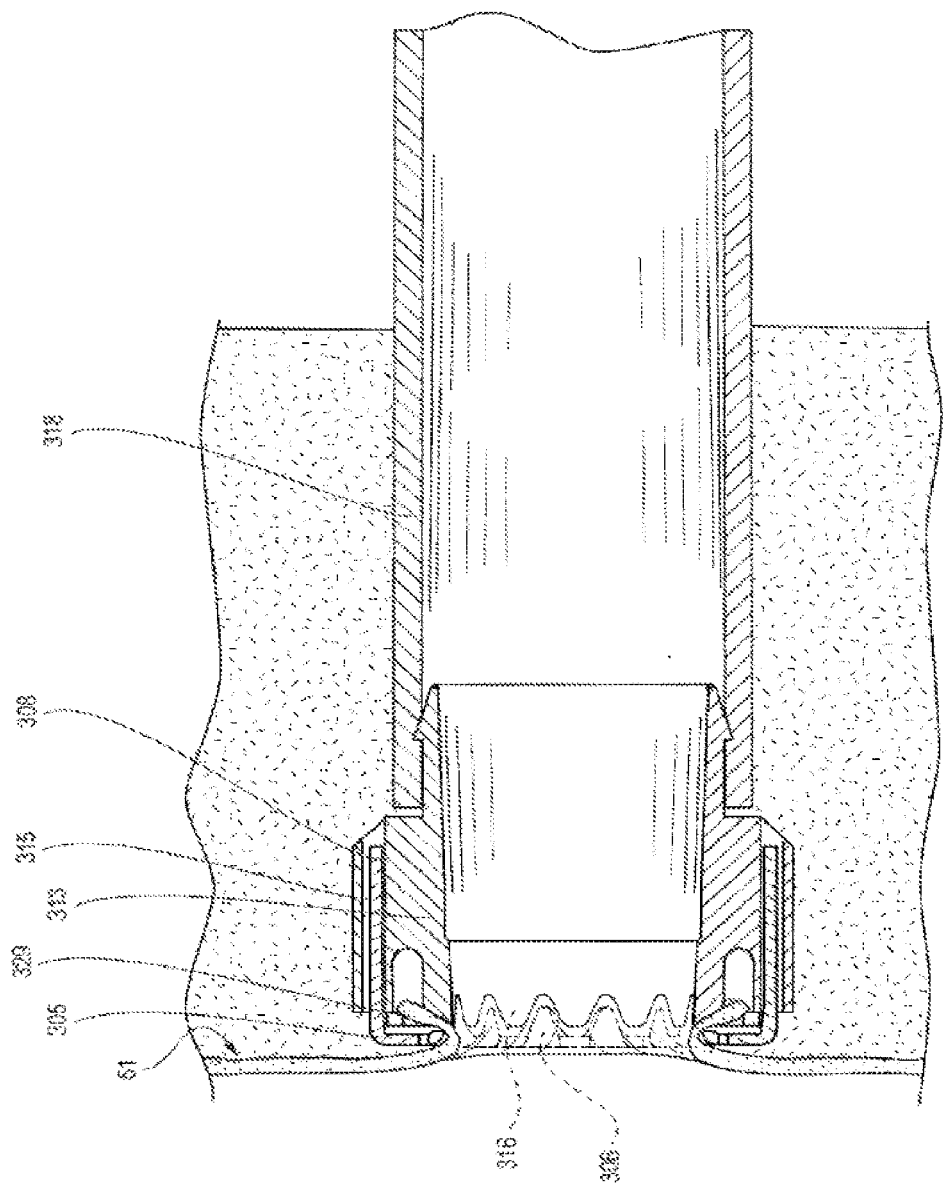
FIG. 20 is a cross-sectional view of a conduit anastomosed to a side of a blood vessel.

With continued reference to FIG. 15, the conduit adapter 313 can include projections or teeth 316 that extend in a distal direction. In some embodiments, when the connection legs 308 of the anastomosis clip 305 are received within the connection channels 315 of the conduit adapter 313, the teeth 316 of the conduit adapter 313 are rotationally offset relative to (e.g., are configured to interdigitate with) the teeth 306 of the clip 305. As shown in FIG. 20, in some embodiments, the contours of the teeth 316 of the conduit adapter 313 and the teeth 306 of the anastomosis clip 305 can be substantially complementary to each other.

Figure 16:
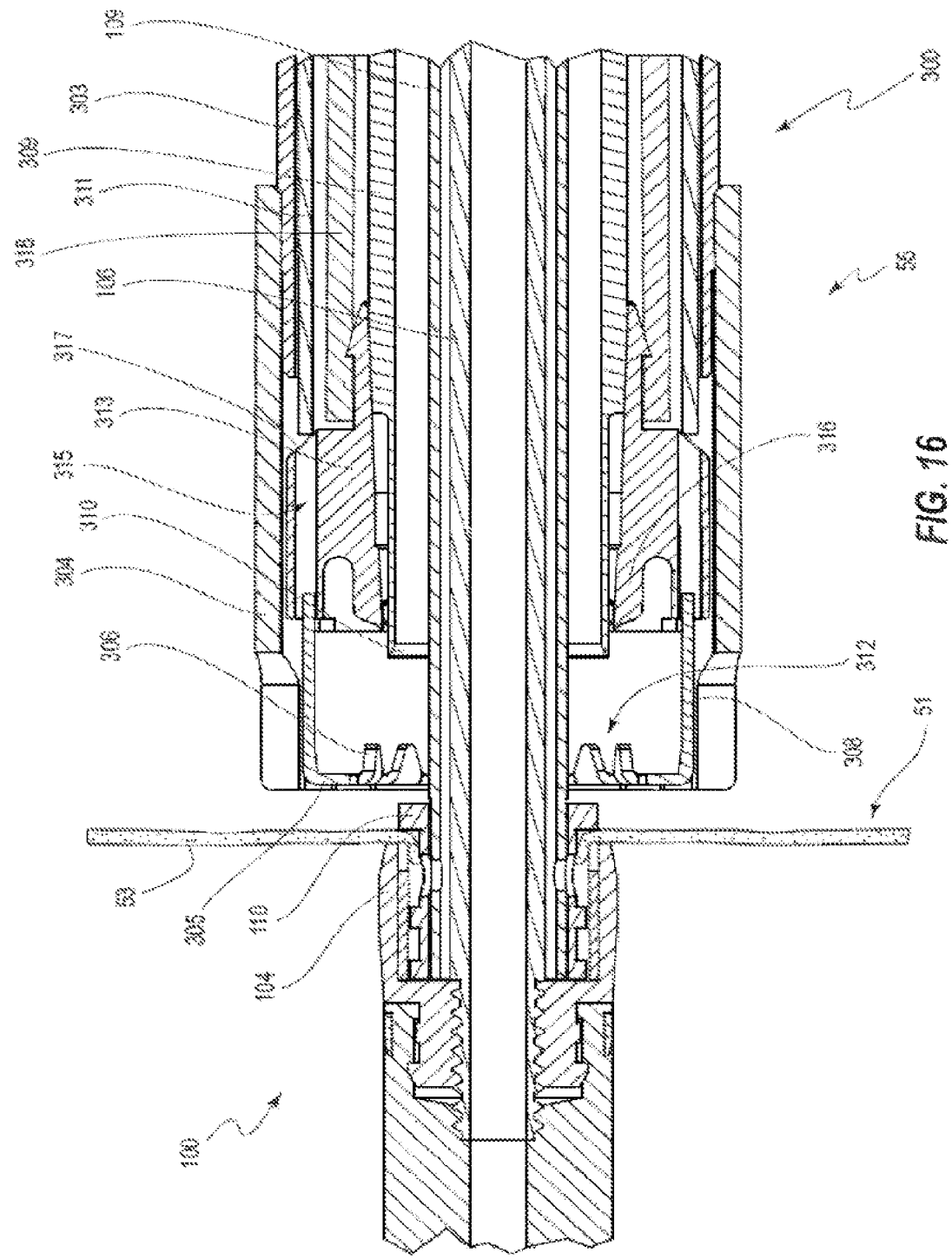
FIG. 16 is a cross-sectional view of the distal end of the anastomosis actuation device of FIG. 12 in an initial placement position.

FIG. 16 illustrates an embodiment of the anastomosis actuation device 300 being coupled with the clamp assembly 100. The anastomosis actuation device 300 is being advanced distally over the clamp assembly 100, and although not shown in FIG. 16, the catch member 342 of the clutch coupling tube 340 is about to be received in the recess between the proximal and distal shoulders 119, 124 of the clutch 108 (see FIGS. 3 and 12). Also not shown are the legs 201 of the tract dilator 200, which are maintaining the insertion tract 55 in an expanded state. Once the anastomosis actuation device 300 is fully coupled with the clamp assembly 100, its distal end (i.e., the distal end of the retaining adapter 304) will be in closer proximity to the vessel wall 53.

Each of the clamp assembly 100 and the anastomosis actuation device 300 are fully assembled. Accordingly, although they are not necessarily discussed at present, visible features previously discussed with respect to FIGS. 12-15 are identified in FIG. 16 for the sake of clarity. It can be seen that in the illustrated embodiment, when the conduit 318 is included in the anastomosis actuation device 300, the conduit adapter 313 frictionally engages an outer surface of the cutter tube 309. The conduit 318 itself is positioned between the cutter tube 309 and the actuator tube 311, but it does not frictionally engage either tube 309, 311. Accordingly, the conduit 318 is held in its pre-anastomosis position primarily by the interaction between the conduit adapter 313 and the cutter tube 309. A distal end of the actuator tube 311 can be in contact with or adjacent to a shoulder 317 of the conduit adapter 313.

Once the anastomosis actuation device 300 is fully coupled with the clamp assembly 100, the anvil pull tube 106 can be drawn in a proximal direction via actuation of the cutter actuator 320, as previously discussed. With the clamp assembly 100 being maintained in a closed configuration (e.g., due to the bias of the biasing member 111; see FIG. 3), movement of the anvil pull tube 106 in the proximal direction can cause the clamp tube 109 to move in the proximal direction as well such that the clamp foot 110, the anvil 104, and the portion of the vessel wall 53 that is between the clamp foot 110 and the anvil 104 can be pulled into the anastomosis actuation device 300. In particular, the clamp foot 110, the anvil 104, and the clamped vessel wall 53 can move proximally through the through hole 312 of the clip 305.

Figure 17:
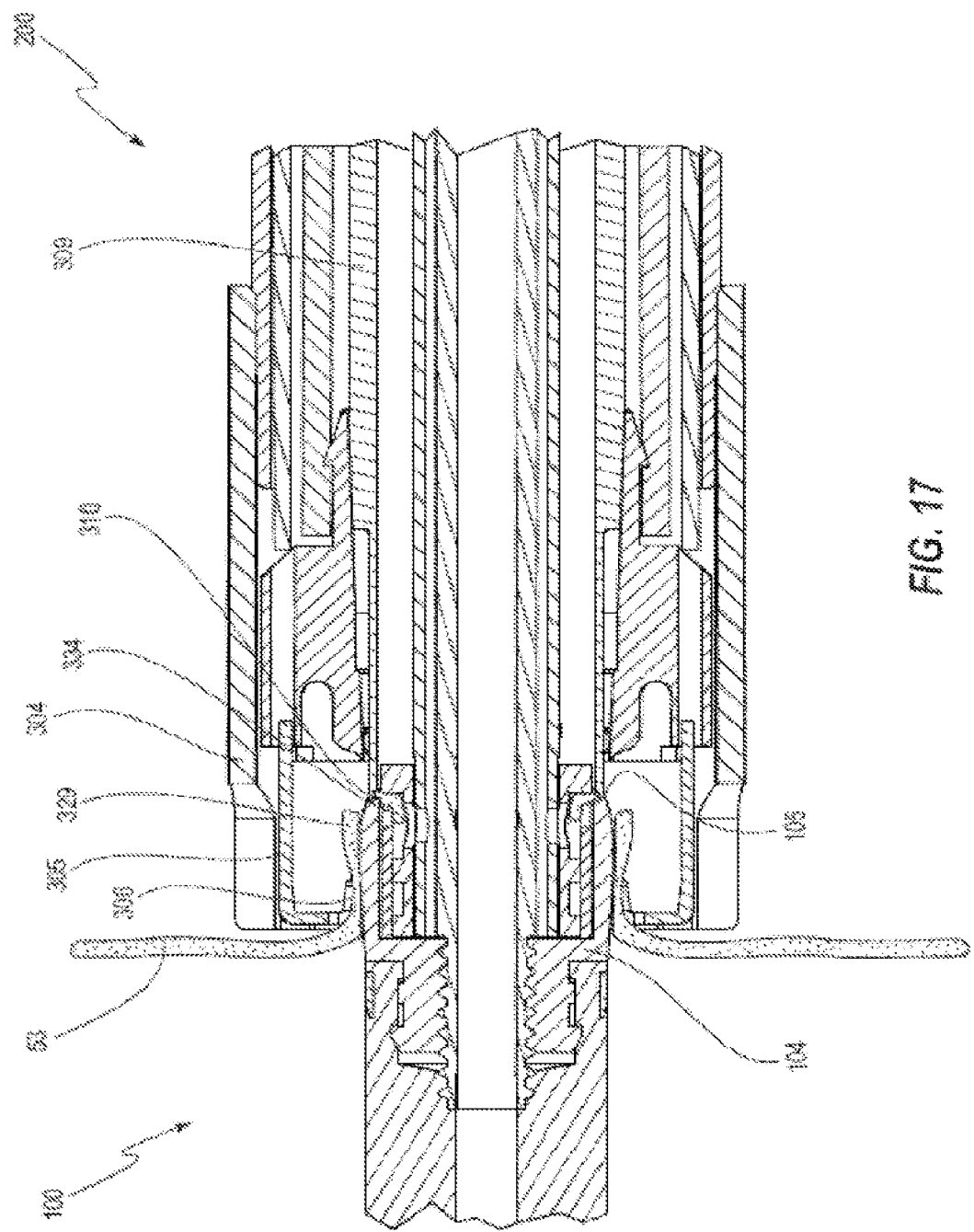
FIG. 17 is a cross-sectional view of the distal end of the anastomosis actuation device of FIG. 12 in a position following the cutting of a portion of the vessel wall.

FIG. 17 illustrates a point in time just after the clamp assembly 100 has been pulled into the anastomosis actuation device 300 sufficiently far for a cut portion 334 to have been severed from the vessel wall 53 by the blade 310 of the cutter tube 309, or stated otherwise, just after the cutter actuator 320 has been moved into the actuated state. In some embodiments, the blade 310 can cut through the vessel wall 53 and contact the proximal surface 105 of the anvil 104 or be embedded therein. In some embodiments, a circular hole in the vessel wall is created by the blade 310. Other shapes are also possible.

In other embodiments, the vessel wall 53 can be pulled through the through hole 312 of the clip 305, and the blade 310 can be advanced in a distal direction to cut the vessel wall 53. Accordingly, in some embodiments, the cutter tube 309 is not fixed relative to the housing.

With continued reference to FIG. 17, the portion of the vessel wall 53 that is pulled into the retaining adapter 304 (e.g., drawn through the through hole 312 of the anastomosis clip 305) can surround an outer surface of the anvil 104. The close proximity of the teeth 306 of the anastomosis clip 305 to the outer surface of the anvil 104 can squeeze the vessel wall 53 and prevent it from retracting from the clip 105. A peripheral edge 329 of the vessel wall 53, which results from the severing of the cut portion 334, can surround or encircle the outer surface of the anvil 104, whereas a portion of the vessel wall 53 that is more distal relative to the peripheral edge 329 of the vessel wall 53 can be captured between the clip 305 and the anvil 104, as just described. The cut portion 332 of the vessel wall 53 can remain in the clamp assembly 100 between the anvil 104 and the clamp foot 110. As previously discussed, in some embodiments, the cutter actuator 320 can be locked or selectively maintained in the actuated state, which in some instances can facilitate subsequent stages of an anastomosis procedure.

Figure 18:
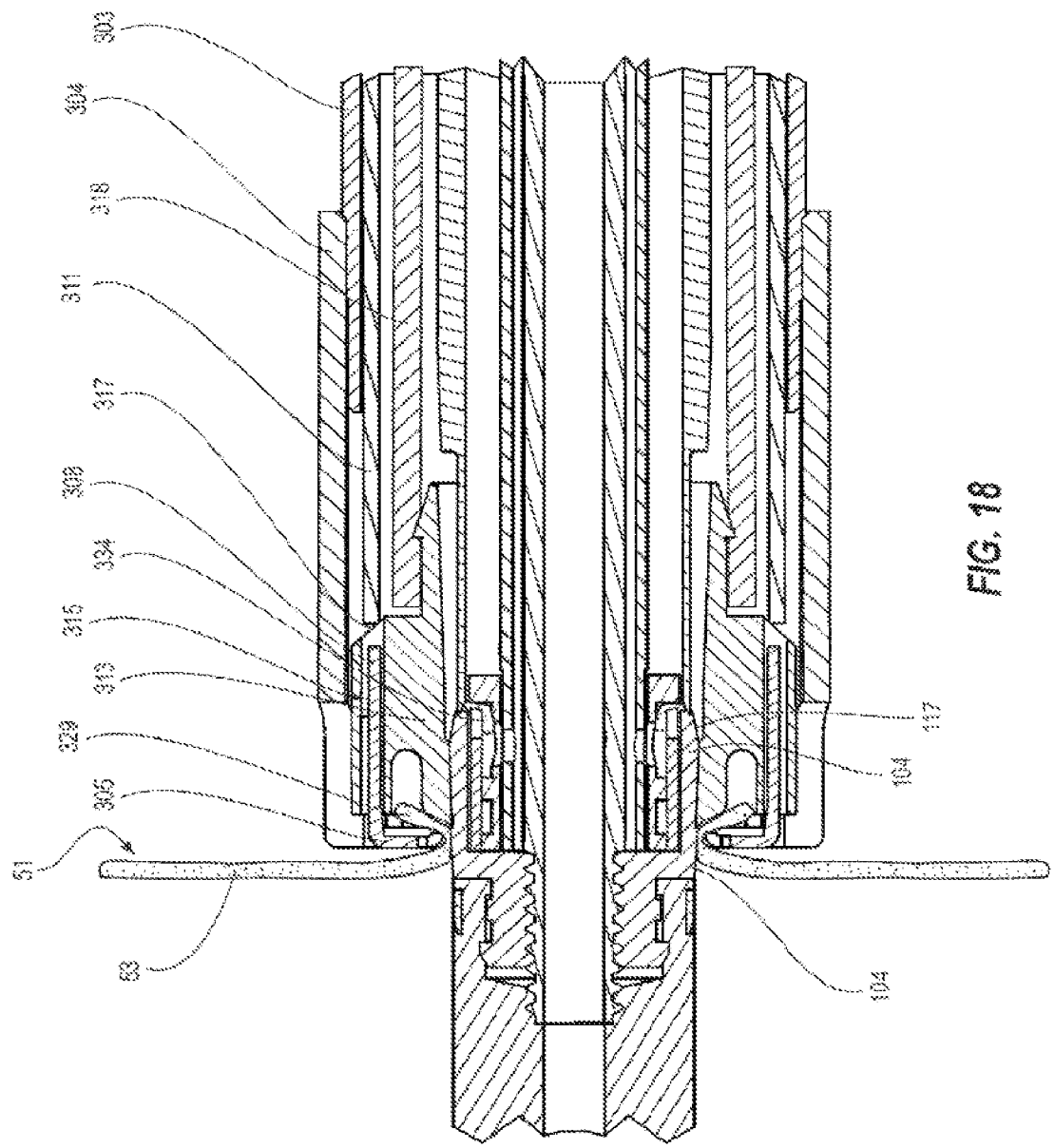
FIG. 18 is a cross-sectional view of the distal end of the anastomosis actuation device of FIG. 12 in a position in which a portion of the vessel wall is captured.

With reference to FIG. 18, once the cut portion 334 has been severed from the vessel wall 53 so as to form an opening therein, anastomosis of the conduit 318 to the blood vessel 51 can be completed. The approximation actuator 330 (FIG. 12) can be moved from the resting state to the approximation state. As previously discussed, such movement can cause the actuator tube 311 to move distally. As it does so, a distal end of the actuator tube 311 pushes against the shoulder 317 of the conduit adapter 313, thereby causing the conduit adapter 313 and the conduit 318 to move in the distal direction. The distal movement of the conduit adapter 313 results in the approximation of the conduit adapter 313 to the clip 305. Stated otherwise, the conduit adapter 313 moves distally and approaches the clip 305, which can result in the peripheral edge 329 of the vessel wall 53 everting over the teeth 306 of the clip 305 and being captured between the interdigitated teeth 306 of clip 305 and the teeth 316 of the conduit adapter 313 (see also FIG. 20).

Stated in yet another way, in the illustrated embodiment, an anastomosis between the conduit 318 and the blood vessel 51 can be accomplished by outwardly everting, via the conduit adapter 313, the portion of the vessel wall 51 that surrounds the anvil 104. A close fit between an inner surface of the conduit adapter 313 and an outer surface of the anvil 104 can cause the peripheral portion 329 of the vessel wall that surrounds the anvil to be everted so as to move outwardly and distally relative to the teeth 306 of the anastomosis clip 305 as the conduit adapter 313 moves distally relative to, and is in close contact with, the outer surface of the of the anvil 104. As previously discussed, in some embodiments, the anvil 104 can have a chamfer 117 at the periphery of its proximal end, which can aid in centering the conduit adapter 313 over the anvil 104 as the conduit adapter is moved distally. In some embodiments, the teeth 316 are flexible, and may define a slightly smaller diameter than the proximal surface of the anvil 104 such that they can effectively scoop the vessel wall away from the anvil 104.

In some embodiments, as the conduit adapter 313 is advanced distally, the connection legs 308 of the anastomosis clip 305 are advanced deeper into the connection channels 315 of the conduit adapter 313. As an interference is achieved, maintained, and/or increased between the connection legs 308 of the anastomosis clip 305 and the connection channels 315 of the conduit adapter 313, the anastomosis clip 305 is substantially fixed relative to the retaining adapter 304 due to the existing interference between the retention legs 307 of the anastomosis clip 305 and the retention channels 314 of the retaining adapter 304 (see FIGS. 13 and 14). As discussed above, the everted tissue 329 is captured between the teeth 306 of the anastomosis clip 305 and the teeth 316 of the conduit adapter 313, which can create a hemostatic seal between the conduit adapter 313 (and hence the conduit 318) and the vessel wall 53.

Figure 19:
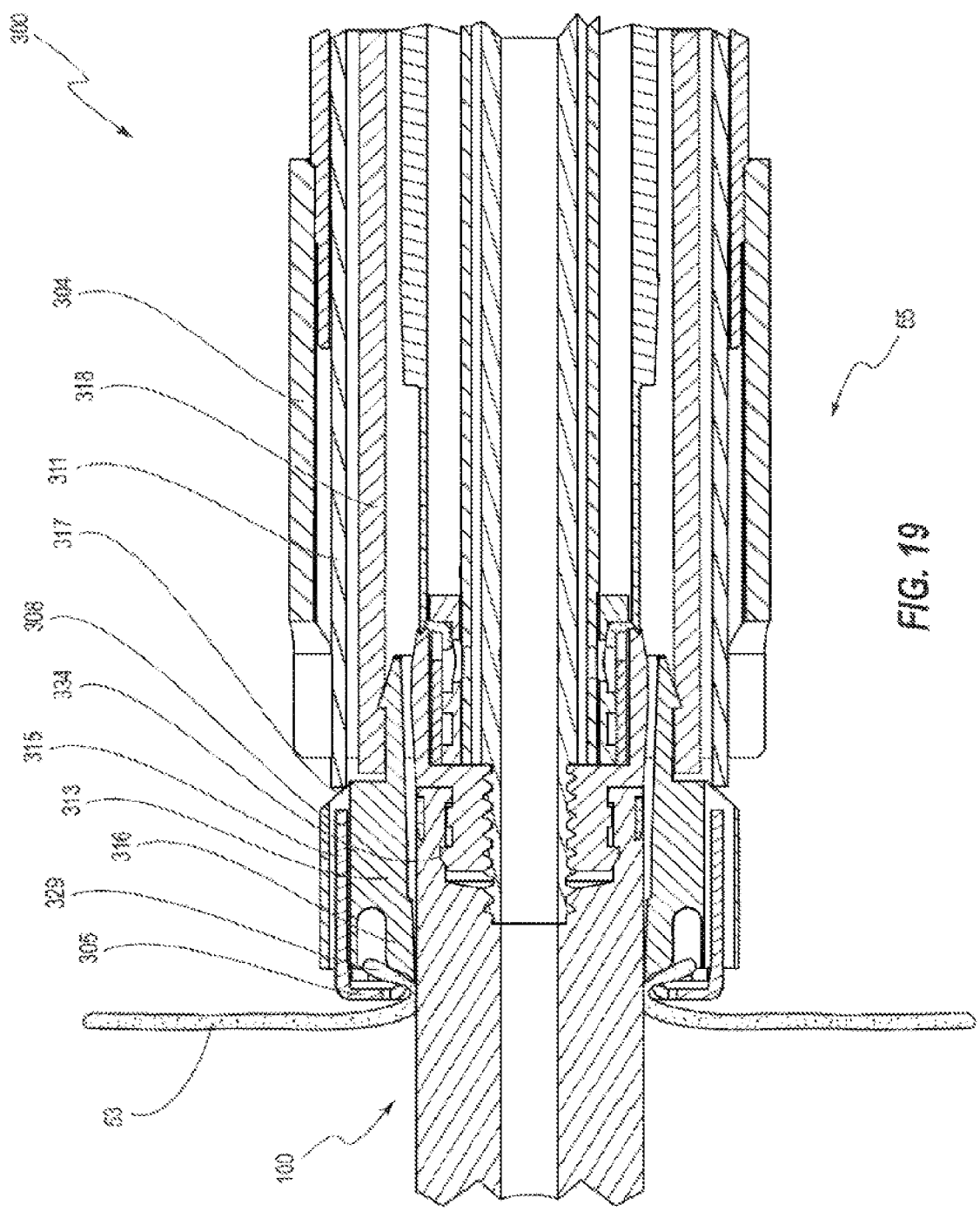
FIG. 19 is a cross-sectional view of the distal end of the anastomosis actuator assembly of FIG. 12 in a position configured to eject a conduit.

With reference to FIG. 19, as additional distally directed force is applied to the conduit adapter 313 via the actuator tube 311, or stated otherwise, as the approximation actuator 330 is moved through the approximation state to the ejection state, the retention legs 307 of the anastomosis clip 305 are eventually forced out of the retention channels 314 of the retaining adapter 304 (see FIGS. 13 and 14). In some embodiments, the force required to friction fit or otherwise attach the connection legs 308 of the anastomosis clip 305 to the connection channels 315 of the conduit adapter 313 is less than the force required to disengage the retention legs 307 of the anastomosis clip 305 from the retention channels 314 of the retaining adapter 304. In further embodiments, the force required to disengage the retention legs 307 of the anastomosis clip 305 from the retention channels 314 of the retaining adapter 304 is less than the force required to puncture or sever the vessel wall 53 via one or more teeth 306, 316 or otherwise compromise the hemostatic seal formed by the anastomosis clip 305 and the conduit adapter 313.

Once the anatomosis of the conduit 318 to the blood vessel 51 is complete, the anastomosis actuation device 300 and clamp assembly 100 can be removed from the insertion tract 55. With reference again to FIGS. 9 and 11, either before or after removal of the anastomosis actuation device 300 and the clamp assembly 100, the insertion tract 55 can be allowed to close by rotating the proximal housing 225 relative to the distal housing 222 of the tract dilator 200 such that the cam surface 224 moves in a proximal direction, thereby releasing a radial constriction on the proximal ends of the arms 221. With the insertion tract 55 in a closed or constricted configuration, the tract dilator 200 can be removed therefrom.

FIG. 20 illustrates the conduit 318 after the anastomosis procedure. As shown, the conduit 318 can provide a passageway that extends through the skin tissue 52 between the blood vessel 51 and a position outside of the skin tissue 52.

Other configurations and processes than those discussed above with respect to the anastomosis actuation device 300 are also possible. For example, in some embodiments, the anastomosis actuation device 300 can comprise spring-loaded or otherwise biased actuators 320, 330, which can move components of the anastomosis actuation device 300 via depression of one or more buttons. In other embodiments, threaded actuators that twist relative to a housing of the housing 302 can be used. As will be evident from the discussion of additional embodiments below, actuation of the anastomosis actuation device 300 can also be achieved via hydraulic systems.

Additionally, the clamp tube handle 120, tract dilator 200, and anastomosis actuator 300 are discussed above as separate tools that can be used in series to create an anastomosis of a conduit and a vessel. In some embodiments, the tools can be provided to the clinician as separate tools, and the clinician can assemble and utilize the tools in a proper sequence. In some embodiments the tools can be manufactured as a single tool capable of performing some or all of the functions discussed above in creating an anastomosis.

Figure 21:
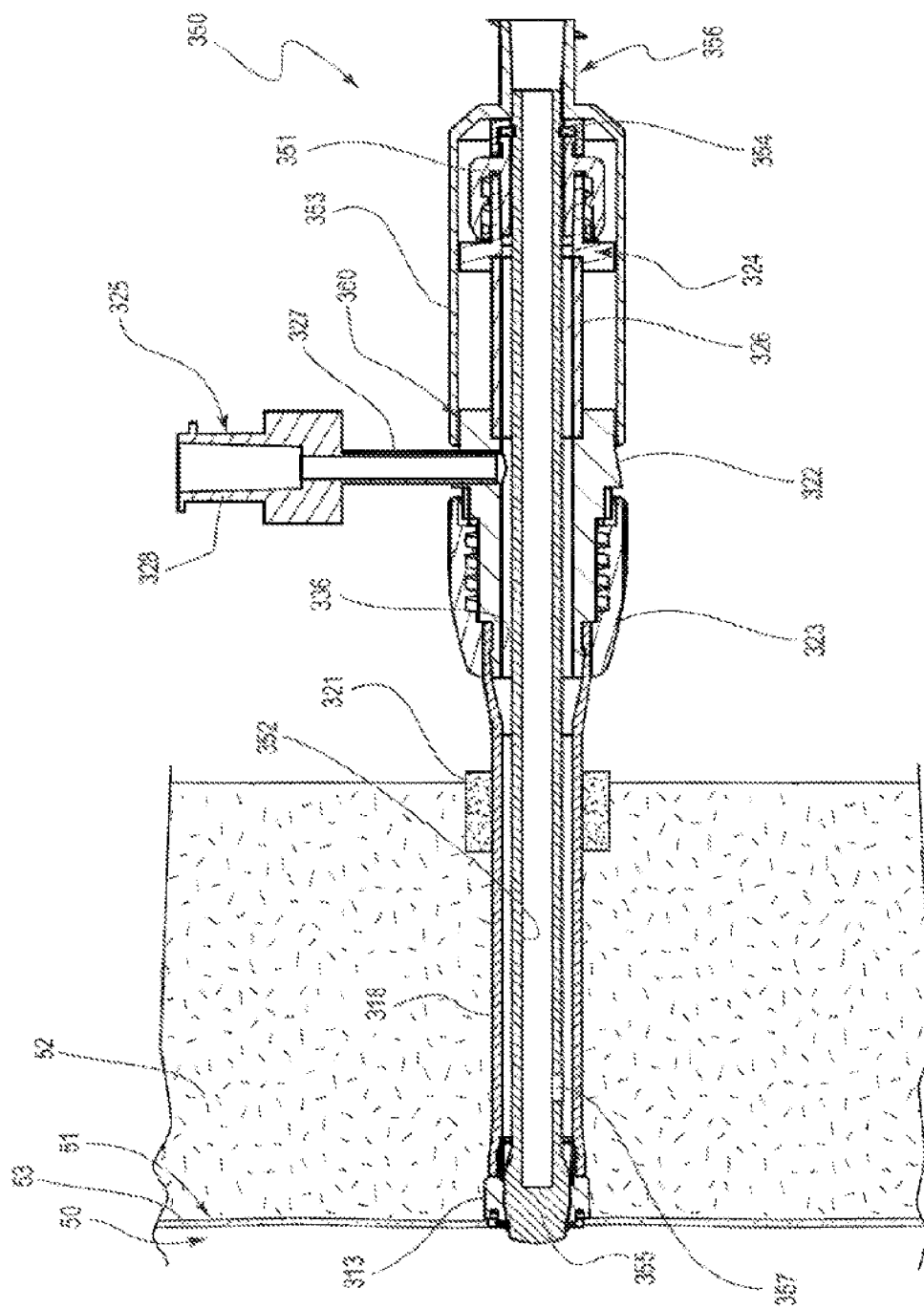
FIG. 21 is a perspective, partial cutaway view of an embodiment of a conduit anastomosed to a blood vessel and an embodiment of a hub and an embodiment of an obturator coupled with the conduit.

With reference to FIG. 21, a proximal end of the conduit 318 can be pulled through skin tissue 52 to a position remote from the anastomosis site, or an exit site, at an outer surface of the skin. For example, known reverse tunneling procedures may be employed. In some embodiments, the conduit 318 can comprise a tissue ingrowth sleeve 321 positioned near the proximal end of the conduit 318 such that the sleeve 321 is positioned in the subcutaneous region. In certain embodiments, tissue 52 can grow into the tissue ingrowth sleeve 321, and can secure the conduit 318 within the tissue 52. The tissue ingrowth sleeve 321 can aid in preventing pathogens from migrating along an external surface of the conduit 318 toward the anastomosis site.

In some embodiments, a hub 322 can be attached to the proximal end of the conduit 318. The attachment can be accomplished via a barb fitting 336 at the distal end of the hub 322 and a compression nut 323. The hub 322 can have two ports 324, 325. A proximal port 324 can be used to insert either one of a catheter and an obturator into the conduit 318, and the side port 325 can be used to infuse or withdraw fluids from the conduit 318. The hub 322 can also include a valve 326, such as a pinch valve or a duck bill valve, to allow for selective occlusion of the conduit 318 when an obturator or catheter is not positioned therein. The side port 325 can be directly associated with the hub 322 or can include a flexible extension tube 327 that is connected with the hub 322 at one end and connected with an adapter 328 at the opposite end.

When not in use for hemodialysis or other procedures that can benefit from the vascular access provided by the conduit 318, an obturator 350 can be used to maintain patency of the anastomosis opening and the conduit 318. The obturator 350 can provide selective fluid communication between the vessel 51 and the conduit 318. The obturator 350 can include a connector 351 configured to couple with the proximal port 324 of the conduit hub 322. The obturator 350 can further include a shaft 352 and a handle 353. The shaft 352 can be slidable within the connector 351, which can include sealing element 354, such as an o-ring, that is configured to contact the shaft 352 in a substantially fluid-tight engagement. The handle 353 can be attached to the proximal end of the shaft 352 and can engage a proximal portion of the conduit hub 322 with a locking mechanism 360 to prevent inadvertent removal of the obturator. Any suitable locking mechanism is contemplated, such as, for example, threading, a friction fit engagement, a snap, etc. The handle 353 can include a port 356 at its proximal end that provides fluid communication to a bore of the shaft 352. The shaft 352 can be covered by a flexible sleeve (not shown) to prevent contamination of the obturator 350 during insertion. For example, the flexible sleeve can be positioned over the shaft 352 between the handle 353 and the connector 351. As the handle 353 is advanced toward the connector 351 to thereby advance the shaft 352 into the conduit 318, the flexible sleeve can compress longitudinally to allow the handle 353 to approach the connector 351.

The obturator 350 can include a tip 355 at the distal end of the shaft that is configured to occlude the anastomosis opening. The tip 355 can plug the anastomosis opening to prevent blood from entering the conduit 318. The tip 355 can extend slightly into the blood vessel 51 when occluding the anastomosis opening. The tip 355 can include a coating that is configured to prevent cell growth and thrombus formation over the anastomosis opening. In some embodiments, the active agent of the coating can include one or more of heparin, rapamycin, and other similar or equivalent agents.

The obturator shaft 352 can be substantially hollow and flexible. In certain of such embodiments, the obturator 350 can include a stiffener (not shown) that can aid with the insertion of the obturator tip 355 through the conduit 318 and into the anastomosis opening. The stiffener can be positioned within the bore of the shaft 352, and in some embodiments, can be connected with the handle port 356. In some embodiments, the stiffener can be removed, and upon removal, can leave the handle port 356 exposed.

In some embodiments, fluid can be flushed through the port 356, through the hollow shaft 352, through an opening 357 in the distal end of the shaft, through the conduit 318, and out of the hub side port 325. In some embodiments, the shaft 352 can be coated with an antimicrobial and an antithrombogenic agent, such as EDTA, capable of being dissolved by the fluid that is flushed through the connector. The dissolved agent can create a lock solution within the conduit 318 that is capable of preventing the formation of biofilm by bacteria. The agent can also prevent the formation of blood clots within the conduit 318. In further or other embodiments, an antimicrobial and/or antithrombogenic solution can be injected through the obturator shaft 352 or the hub side port 325 and into the conduit lumen 352.

In use, the obturator connector 351 is secured to the proximal port 324 of the conduit hub 322 with the shaft 352 extending proximally from the connector 351. The obturator shaft 352 and the tip 355 are then advanced into the conduit 318 and the tip 355 is seated in the anastomosis opening. The obturator stiffener (not shown) is then removed from the obturator 350. Fluid, such as a normal saline solution, heparin flush solution, and/or an antimicrobial lock solution, can be injected into the bore of the shaft 352 via the obturator handle port 356. A cap (not shown) can be connected to the handle port 356 to prevent leakage of fluid therefrom.

The obturator 350 can be selectively inserted into and removed from the conduit hub 322 as desired. For example, in some embodiments, the obturator 350 is inserted after the anastomosis is originally formed and thereby occludes the anastomosis opening. When fluid communication between the blood vessel 51 and the conduit 318 is desired, the obturator 350 can be removed, thereby opening the anastomosis opening. In some embodiments, upon removal of the obturator 350, a catheter (such as may be used for hemodialysis) can then be inserted through the conduit hub 322, through the conduit 318, and into the blood vessel 51 as described below. At the conclusion of a hemodialysis session, the catheter can be removed from the vessel 51 and the conduit 318. The obturator 350 then can again be inserted into the conduit 318 to occlude the anastomosis opening until a subsequent hemodialysis session. Additional apparatus and methods related to obturators configured to maintain the patency of an anastomosis site can be found, for example, in U.S. Pat. No. 7,118,546, titled APPARATUS AND METHODS FOR FACILITATING REPEATED VASCULAR ACCESS, which issued on Oct. 10, 2006, the entire contents of which are hereby incorporated by reference herein.

Any suitable variety of catheter can be coupled with the conduit hub 322 for any suitable procedure in which access to the blood vessel 51 is desired. For example, in some embodiments, a dual-lumen catheter suitable for use in hemodialysis may be employed. In some embodiments, only a distal tip of the catheter is inserted into the vessel 51, which can reduce the incidence of trauma to the intima layer of the vessel wall 53 as a catheter passes through the anastomosis site and into the vessel lumen 50. Hemodialysis can be performed by drawing blood into one lumen of the distal tip of the catheter and returning filtered blood through the other lumen of the distal tip. Following a dialysis session, the catheter can be removed and replaced with the obturator 350, or it can be stored or otherwise positioned in the conduit 318. In some embodiments, the catheter itself can act as the obturator when the catheter is retracted into the conduit 318. For example, the distal end of the catheter can be configured to occlude the anastomosis opening in a manner such as that described with respect to the obturator tip 355.

FIGS. 22A and 22B illustrate an embodiment of a tract dilator 400, which can resemble the tract dilator 200 described above in certain respects. Accordingly, like features may be designate with like reference numerals, with the leading hundreds numeral incremented to "4." Any suitable combination of the features described with respect to the tract dilator 200 can be employed with the tract dilator 400, and vice versa. As with the tract dilator 200, the tract dilator 400 can be configured for use with embodiments of the clamp assembly 100 and of the anastomosis actuation device 300.

In the illustrated embodiment, the tract dilator 400 can include an actuator 420, which can be connected with one or more legs 401 via one or more arms 421. In some embodiments, the legs 401 and the arms 421 are pivotally connected to each other, whereas in other embodiments, they are substantially fixed relative to each other. In the illustrated embodiment, each of the legs 401 and arms 421 is formed as an integral piece, which may be capable of flexing. When in a closed or constricted orientation, the legs 401 can define a small insertion tract 55.

The actuator 420 can include a lever 430, with which the arms 421 can be mechanically linked or otherwise operatively connected. The actuator 420 can be positioned adjacent to a handle 432 to facilitate its actuation via a squeezing action. Actuation of lever 430 can move the arms 421 radially outward. In some embodiments, the ratchet lever 430 can be ratcheted such that multiple squeeze cycles are used to effect the desired amount of dilation of the tract 55. As shown in FIG. 22B, in some embodiments, the tract 55 is dilated such that a proximal end thereof is wider than a distal end thereof. A second grip handle 434 can be provided for stabilization and ease of use in handling the actuator 420.

In certain embodiments, the actuator 420 can be transitioned from the expanded orientation shown in FIG. 22B back to the constricted orientation shown in FIG. 22A by deactivating a lock, or via any other suitable release mechanism, such that the arms 421 are released and the legs 401 are moved radially inward due to the resilience of the separated portions of the skin tissue 52.

In other embodiments, the actuator 420 may be coupled with the legs 401 and arms 221 discussed above with respect to the tract dilator 200, and it may be used in place of the dilation actuator 220 (see FIGS. 9 and 11). In such embodiments, the actuator 420 can be configured to cause the proximal ends of the arms 221 to move radially inward upon actuation, rather than radially outward as discussed with respect to the arms 421, such that the movement of the arms 221 and the legs 201 is substantially the same as it is with the illustrated embodiment of the tract dilator 200.

FIGS. 23A-23H illustrate additional embodiments of a tract dilator 500, which can resemble the tract dilators 200, 400 described above in certain respects. Any suitable combination of the features described with respect to the tract dilators 200, 400 can be employed with the tract dilators 500, and vice versa. As with the tract dilators 200, 400, the tract dilators 500 can be configured for use with embodiments of the clamp assembly 100 and of the anastomosis actuation device 300.

Figures 23A, 23B:
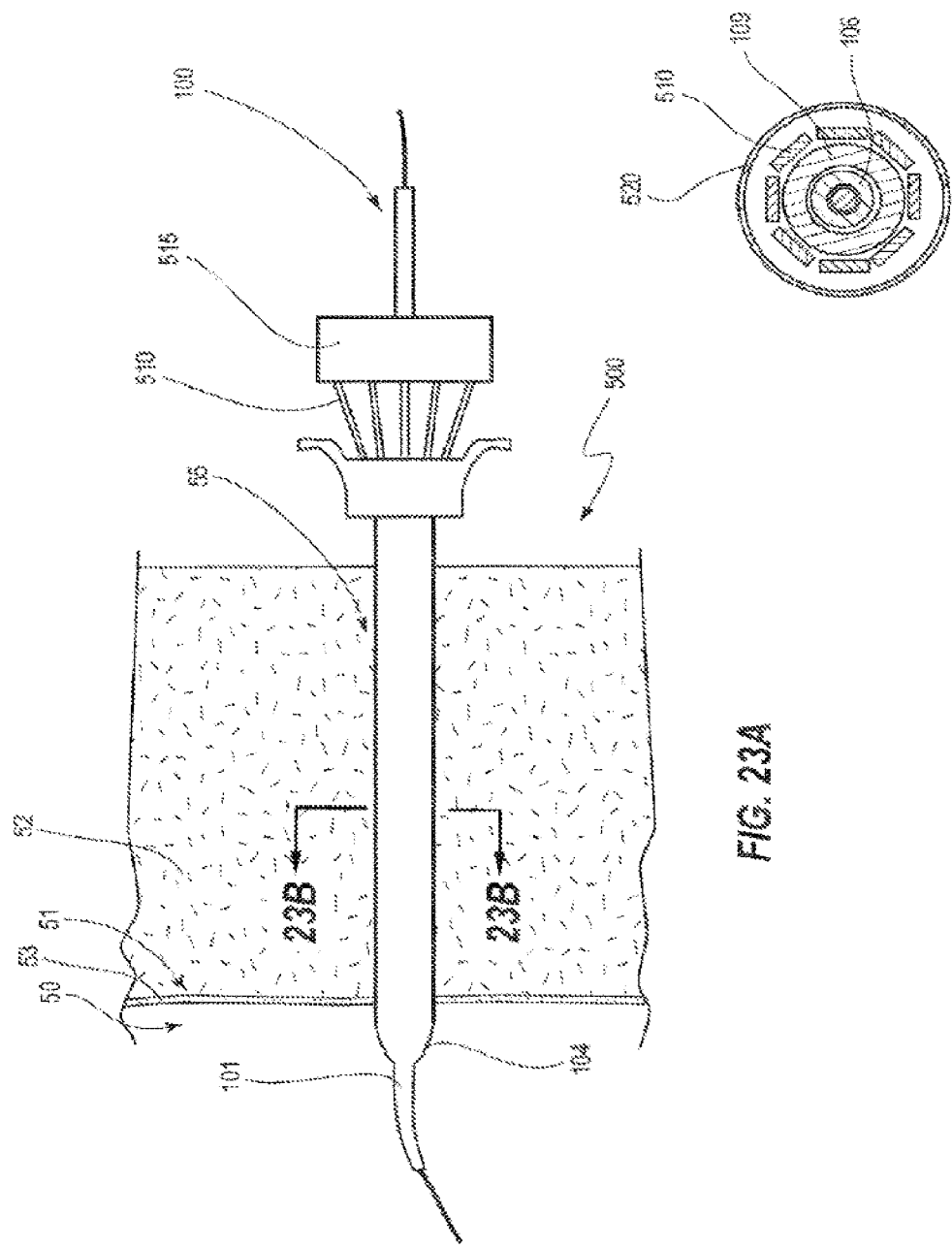
FIG. 23A illustrates an elevation view of another embodiment of a tract dilator that includes ribbons and a separable sheath.
FIG. 23B illustrates a cross-sectional view of the tract dilator of FIG. 23A

As shown in FIGS. 23A-23C, a tract dilator 500 can include a plurality of longitudinal ribbons 510 attached to a hub or ring 515 at their proximal ends. In various embodiments, the tract dilator 500 includes three or more, four or more, five or more, six or more, seven or more, or eight or more ribbons 510. The ribbons 510 can be positioned over the clamp assembly 100 prior to insertion of the clamp assembly 100 into the blood vessel 51, or can be positioned over the clamp assembly 100 following clamping of the vessel wall 53. A sheath 520 can cover the ribbons during insertion (see FIGS. 23A and 23B). The sheath 520 can be split and separated, or peeled away, prior to expansion of the ribbons 510, or the sheath 520 can be split automatically during the expansion process. The sheath 520 can facilitate insertion of the ribbons 510 into the insertion tract 55, in some embodiments. As can be appreciated by comparing FIGS. 23A and 23C, after being split, the sheath 520 can be removed from the insertion tract 55.

As shown in FIG. 23D, in some embodiments, the ribbons 510 can have features to prevent their backout from the insertion tract 55. The features can comprise one or more barbs 525 along a longitudinal face or a longitudinal edge of the ribbons 510. In some embodiments, the backout-prevention features can define a dog-bone shape (not shown) or other suitable configuration at the distal end of the ribbons 510.

Figure 23F:
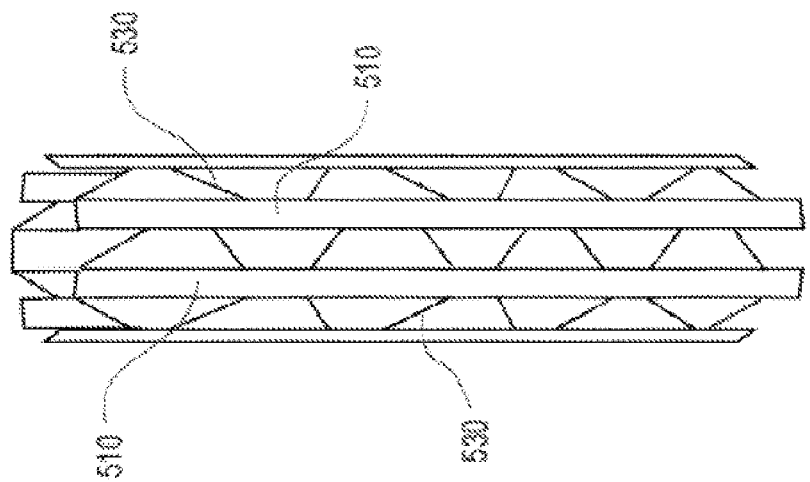
FIG. 23F is a perspective view of the ribbons and linkages of FIG. 23E in an expanded state.
Figure 23E:
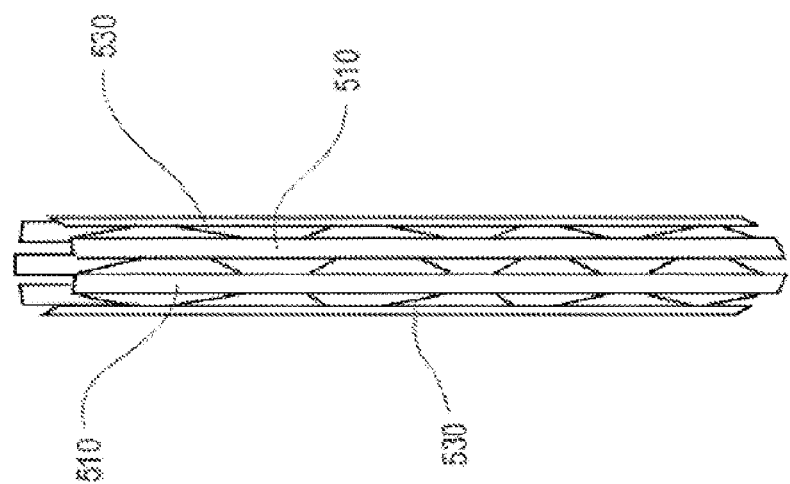
FIG. 23E is a perspective view of a set of ribbons and linkages that is compatible with the tract dilator of FIG. 23A shown in a non-expanded or constricted state.

As shown in FIGS. 23E and 23F, the ribbons 510 can be connected via flexible linkages 530. The linkages 530 can be initially substantially longitudinally oriented (see FIG. 23E). As the tract dilator 500 is radially expanded such that the distance between the ribbons 510 increases, the linkages 530 can bend at points or positions at lateral edges of the ribbons 510 such that the orientation of the linkages 530 can become more transverse relative to the longitudinal axis of the tract dilator 500 (see FIG. 23F). The interconnecting linkages 530 can help to prevent dilated tissue 52 from collapsing into the insertion tract 55. The interconnected ribbons 510 can be produced utilizing a laser cutting process or any other suitable technique. In other embodiments, the tract dilator 500 can comprise a braided wire or stent-like device.

With reference again to FIG. 23C, in some embodiments the ribbons 510 can be radially expanded via a plunger 530, which can be inserted through the hub 515. The plunger 530 can be a unitary device or it can comprise a series of nested tubes having increasing diameters. The plunger 530 can be a separate component or it can be integrated into the anastomosis actuation device 300. The plunger 530 can comprise a tip 535, which can be relatively blunt in some embodiments or tapered in other embodiments, which may reduce dilatation forces. The plunger 530 can be driven by hand (e.g., manually urged in a distal direction). In other embodiments, the plunger 530 can be mechanically driven, such as by a piston utilizing hydraulic or pneumatic pressure.

In certain embodiments, as the plunger tip 535 moves toward the distal end of the ribbons 510, the ribbons 510 are forced radially outwardly so as to expand the insertion tract 55. Following tract dilation, the plunger 530 can be removed from the tract dilator 500. In some embodiments of the tract dilators 200, 400 discussed above, the legs 201, 401, respectively, can be dilated via a plunger in a similar manner, rather than via the actuators 220, 420.

Figure 23H:
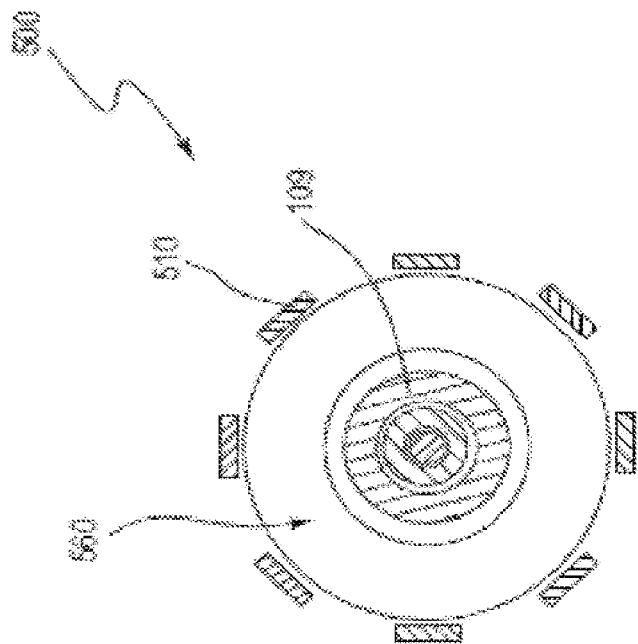
FIG. 23H is a cross-sectional view of another embodiment of a tract dilator that includes a balloon.
Figure 23G:
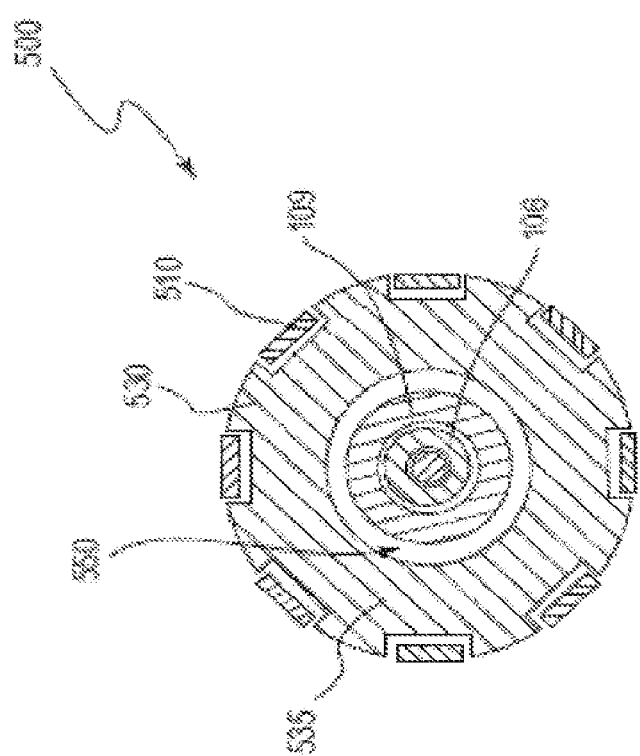
FIG. 23G is a cross-sectional view of another embodiment of a tract dilator such as the tract dilator of FIG. 23A that includes a plunger tip having grooves that are configured to receive at least a portion of ribbons therein.

As illustrated in FIG. 23G, in certain embodiments, the plunger tip 535 can have grooves or notches 540 that engage the ribbons 510 of the dilator 500 as the plunger 530 is advanced distally. Engagement between the notches 540 and the ribbons 241 can inhibit or prevent the plunger 530 from rotating relative to the ribbons 510 during insertion. Additionally, in some embodiments, the plunger 530 defines an opening 550 sized to receive the clamp tube 109. The plunger 530 can be configured to translate relative to (e.g., to slide over) the clamp tube 109. As mentioned above, the anvil pull tube 106 can be received within the clamp tube 109, which is also shown in FIG. 23G.

With reference to FIG. 23H, in some embodiments a tract dilator 500 can include a balloon 560 that is configured to expand the ribbons 510, rather than the plunger 530. The balloon 560 is shown in an expanded state. The balloon 560 can be positioned between the ribbons 510 and the clamp tube 109. The balloon 560 can comprise a material that is compliant (e.g., stretchy or elastomeric), and thus capable of stretching so as to expand, or can be non-compliant (e.g., substantially inextensible), and thus configured to unroll, unfold, or expanding in some other manner. Following vessel clamping, the balloon 560 can be expanded using air or liquid. As the balloon 560 expands, the ribbons 510 can be forced radially outward, thereby causing the insertion tract 55 to be dilated. Following dilation, the balloon 560 can be removed from the tract dilator 500. In some embodiments of the tract dilators 200, 400, the legs 201, 401, respectively, can be dilated via a balloon in a similar manner, rather than via the actuators 220, 420.

FIGS. 24A-24F illustrate embodiments of a tract dilator 600, which can resemble the tract dilators 200, 400, 500 described above in certain respects. Any suitable combination of the features described with respect to the tract dilators 200, 400, 500 can be employed with the tract dilators 600, and vice versa. As with the tract dilators 200, 400, 500, the tract dilators 600 can be configured for use with embodiments of the clamp assembly 100 and of the anastomosis actuation device 300.

In some embodiments the tract dilator 600 can comprise a foldable sleeve 610 attached to a handle or hub device 615. In various embodiments, the sleeve 610 can define a diameter of from about 15 French to about 30 French, no less than about 15 French, no less than about 20 French, no less than about 25 French, or no less than about 30 French when in an unfolded or expanded state. Other sizes are also contemplated. For insertion into the insertion tract 55, the sleeve 610 can be folded tightly around the clamp assembly 100 such that an inner diameter of the sleeve 610 closely matches the outer diameter of the clamp tube 109.

As shown in FIGS. 24A-24C, to facilitate a smooth insertion of the sleeve into the insertion tract 55 and to maintain the sleeve 610 in a folded state, the sleeve 610 can be covered or encircled with a splittable or peel-away sheath 620. In some embodiments, the sheath 620 can be manually split prior to expansion of the sleeve 610, and in other embodiments, the sheath 620 can be split automatically during the expansion of the sleeve 620.

Figure 24D:
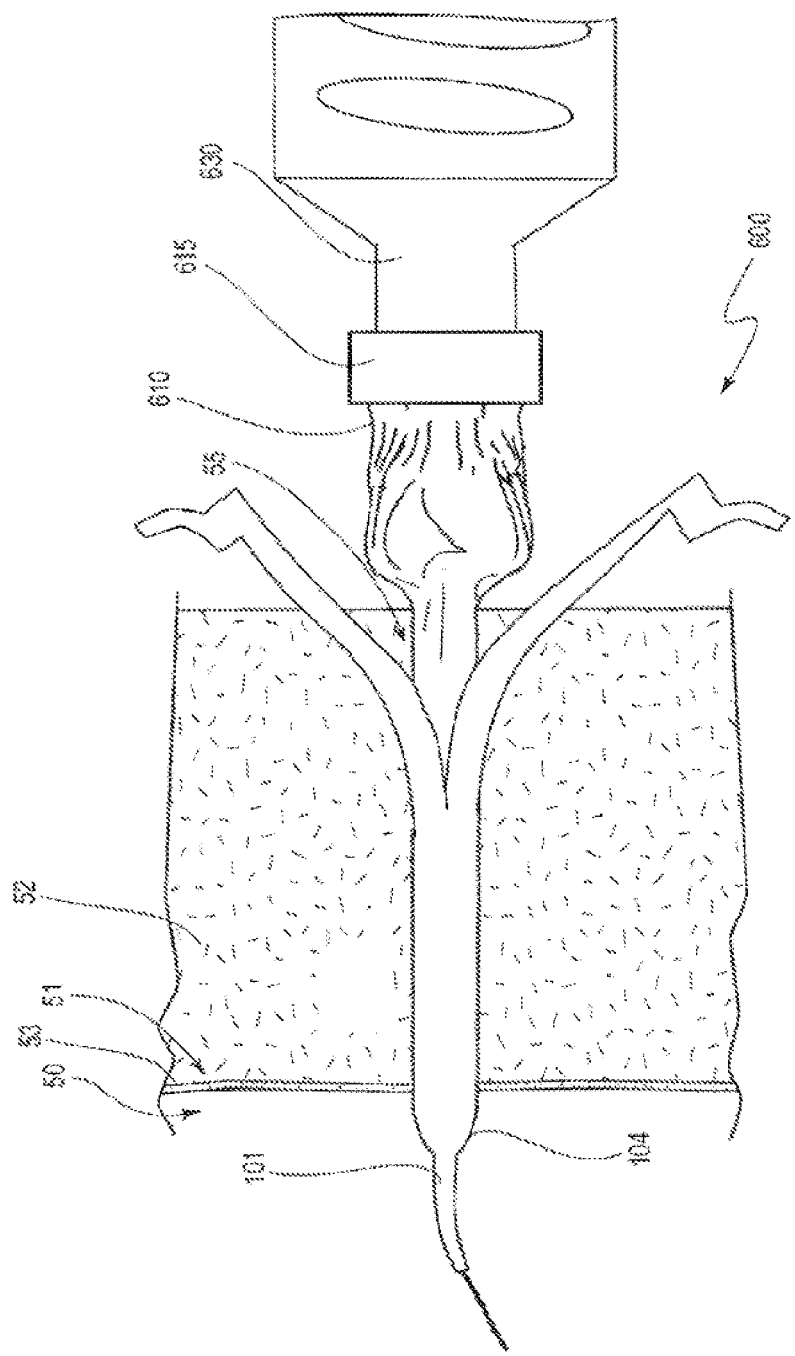
FIG. 24D is an elevation view of the tract dilator of FIG. 24A showing the sleeve being expanded by the insertion of a plunger therein.
Figure 24E:
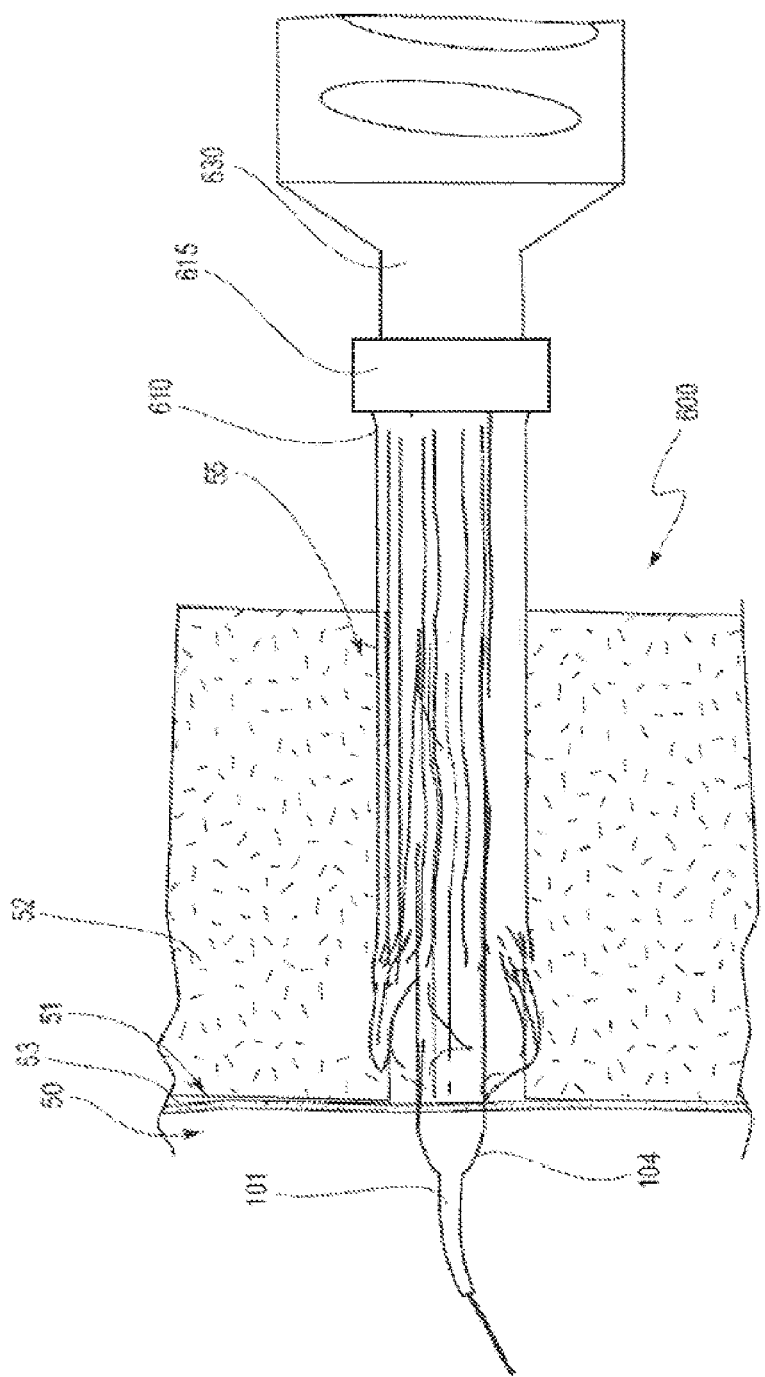
FIG. 24E is an elevation view of the tract dilator of FIG. 24A showing the sleeve in a substantially fully expanded state with the plunger inserted to a distal end thereof.

With reference to FIGS. 24D and 24E, in some embodiments the dilator sleeve 610 can be radially expanded via a plunger 630, which can be inserted into the sleeve 610 through the hub 615. The plunger 630 can be a unitary device or it can comprise a series of nested tubes having increasing diameters. The plunger 630 can be a separate component or can be a part of the anastomosis actuation device 300. The plunger 630 can comprise a tip 635, which can be relatively blunt in some embodiments or tapered in other embodiments so as to reduce dilatation forces. The plunger 630 can be driven by hand (e.g., manually urged in a distal direction). In other embodiments, the plunger 630 can be mechanically driven, such as by a piston utilizing hydraulic or pneumatic pressure.

In certain embodiments, as the plunger tip 635 moves toward the distal end of the sleeve 610, the sleeve 620 is forced radially outwardly so as to be unfolded and thereby dilate the insertion tract 55. In some embodiments, the sleeve 610 is fully expanded by the plunger 630, such that the insertion tract 55 can be dilated to any of the widths previously recited. Following tract dilation, the plunger 630 can be removed from the tract dilator 600.

Figure 24F:
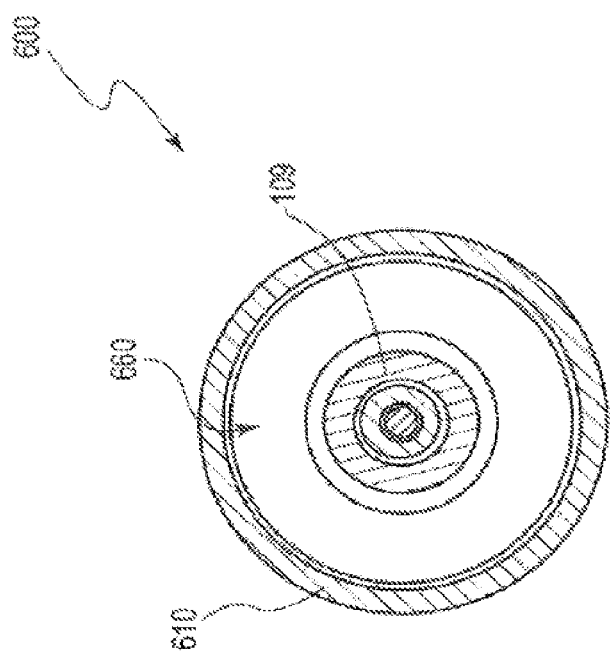
FIG. 24F is a cross-sectional view of another embodiment of a tract dilator that includes a balloon.

With reference to FIG. 24F, in some embodiments a tract dilator 600 can include a balloon 660 such as the balloon 560 instead of the plunger 630. The balloon 660 can be positioned between the sleeve 610 and the clamp tube 109, and can be expanded using air or liquid. As the balloon expands the sleeve 610 can be forced radially outward causing dilation of the insertion tract 55. Following dilation, the balloon 660 can be removed from the tract dilator 660.

Figure 25:
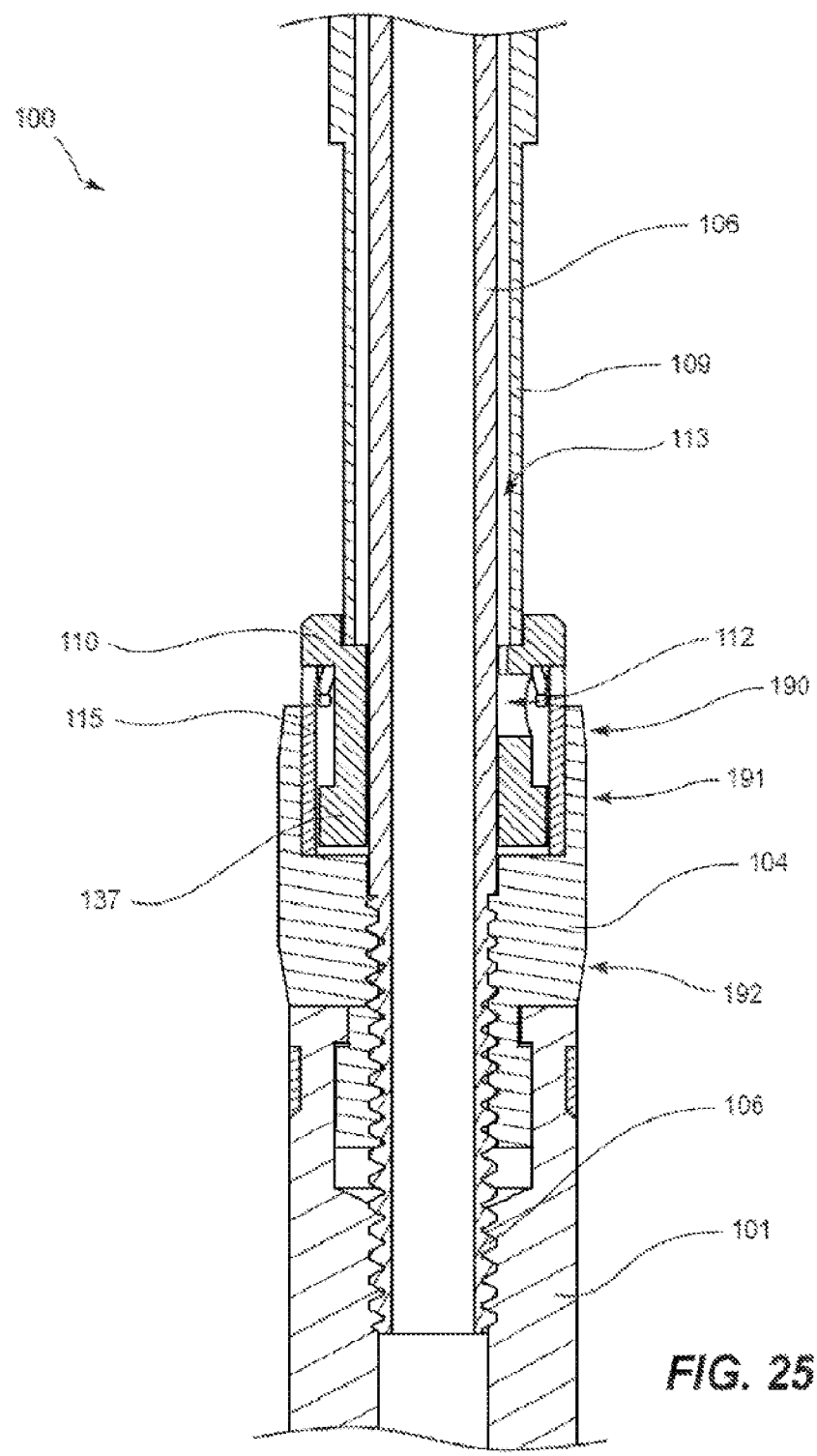
FIG. 25 is a cross-sectional view of another embodiment of a clamp assembly.
Figure 26:
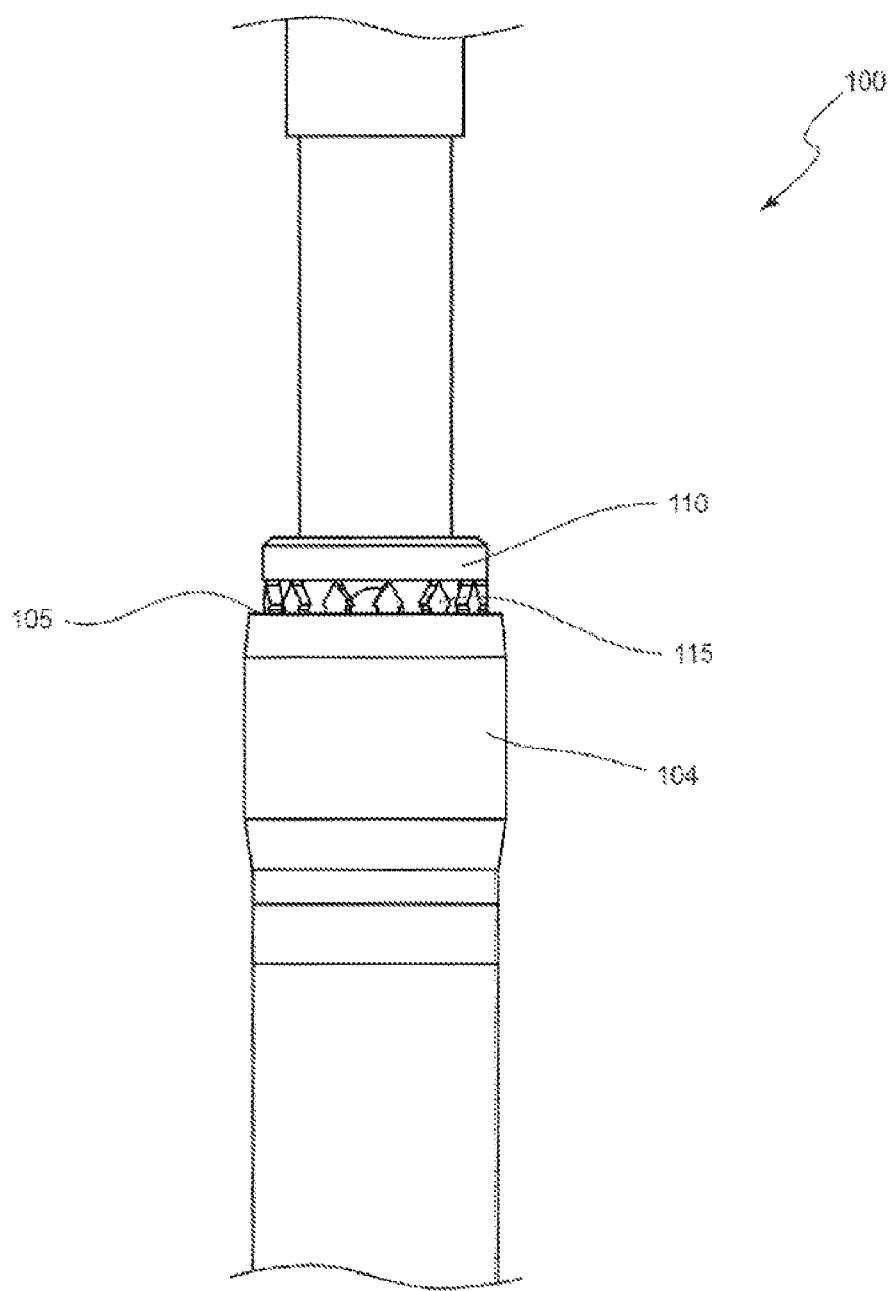
FIG. 26 is an elevation view of the clamp assembly of FIG. 25.
Figure 27:
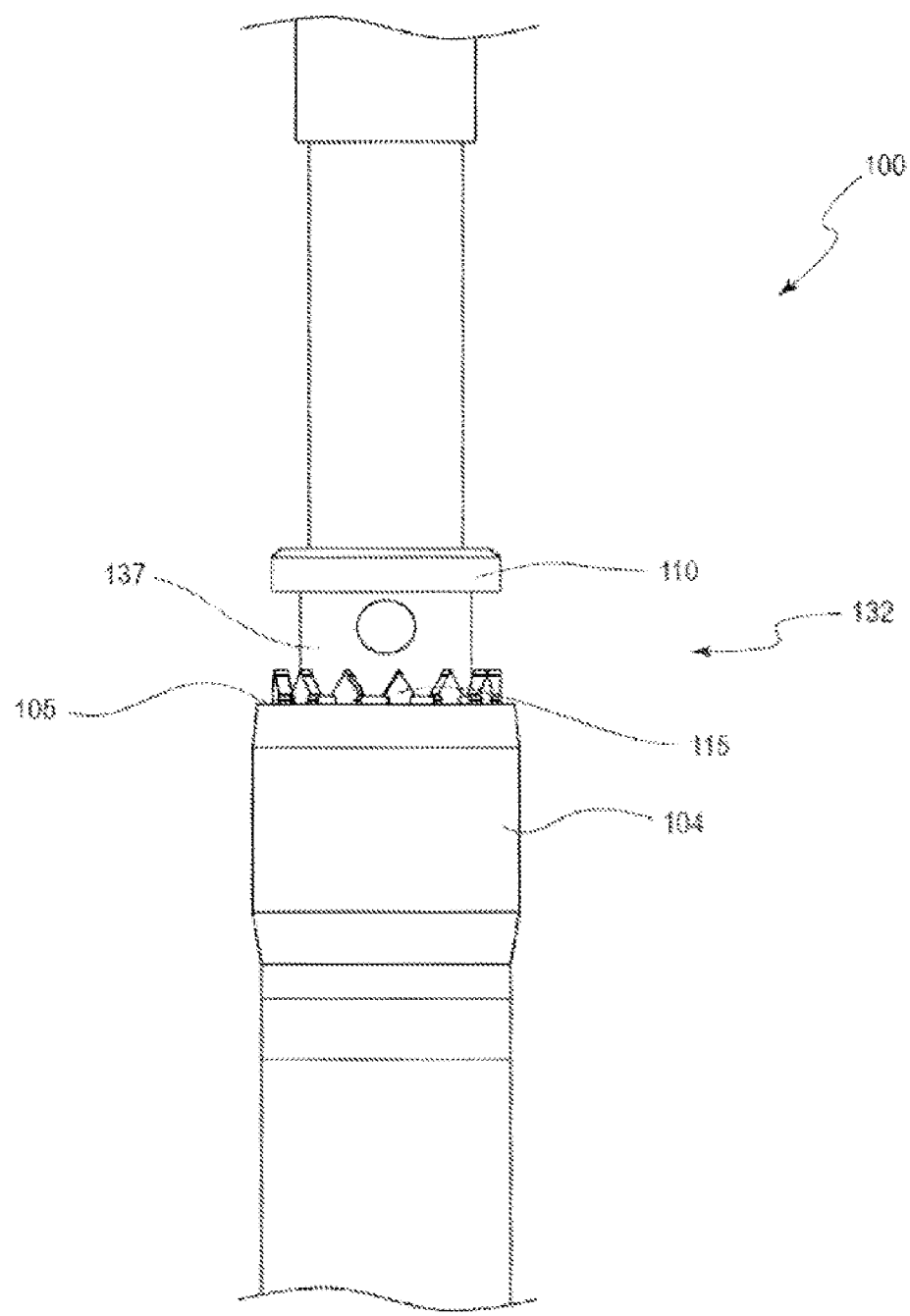
FIG. 27 is an elevation view of the clamp assembly of FIG. 25 in another operational state.

FIGS. 25-27 illustrate another embodiment of the clamp assembly 100, such as the clamp assembly shown FIGS. 2, 6, and 8. The proximal end surface 105 of the anvil 104 is perpendicular to a longitudinal axis of the anvil 104. The proximal end surface 105 can be configured to engage the cutter blade 310 during the cutting stage of an anastomosis procedure, as described above. A proximal portion 190 of a peripheral surface of the anvil 104 can be chamfered to facilitate passage of an anastomotic implant over the anvil 104 during the approximation stage of an anastomosis procedure. A middle portion 191 of the peripheral surface of the anvil 104 can be parallel to a longitudinal axis of the anvil 104. The middle portion 190 can provide an area to which the vessel wall 53 retracts following cutting of the vessel wall 53 by the cutter tube 309. A distal portion 192 of the peripheral surface of the anvil 104 can be chamfered to provide a smooth transition from the introducer tip 101 to the anvil 104. The smooth transition facilitates an easy insertion of the anvil 104 into a blood vessel 51 during the insertion procedure. The anvil 104 can be made from a plastic material such as Delrin®, PVC, polyurethane or other materials that facilitate cutting of vessel wall tissue when the cutter blade 310 and the anvil 104 engage. Embodiments of the anvil 104 can be manufactured using known manufacturing methods such as injection molding, machining, or casting.

With continued reference to FIGS. 25-27, a tissue capturing tubular structure 133 is shown nested in the anvil 104. The tubular structure 133 can have at least one spike like projection or tooth 115 extending proximally beyond the proximal end face 105 of the anvil 104. In some embodiments, the number of teeth can be from 12 to 18. The teeth 115 can be barbed shape with a single barb or double barbs. In some embodiments, the tissue capture tube 133 can be made from stainless steel using a laser to cut the tube from a tube.

As shown in FIG. 25, the distal end of the anvil pull tube 106 is securely fastened not only to the anvil 104, but also the introducer tip 101. As shown in FIGS. 26 and 27, when the clamp assembly 100 is in the closed orientation, a distal surface of the clamp foot 110 can contact the proximal tips or spike-like projections of the teeth 115. The clamp foot 110 can be devoid of notches (see FIG. 26), but blood can still be permitted to flow into the opening 112 through spaces between adjacent teeth 115.

In the illustrated embodiment, the teeth 115 are fixedly secured to the anvil 104, rather than to the clamp foot body 137. Accordingly, when the clamp assembly 100 is moved to the open orientation shown in FIG. 33, the clamp foot 110 can be spaced from the teeth 115 by a relatively larger amount. In some cases, this can permit the vessel wall 53 (see, e.g., FIG. 6) to more easily resiliently close around the clamp foot body 137 within the region of the gap 132. A diameter of the clamp foot 110 can be approximately equal to the diameter of the tissue capture tube 133 such that the clamp foot 110 rests on the teeth 115 when the clamp is in the clamp closed position. When the clamp assembly 100 is moved to the closed orientation, the clamp foot 110 can compress the vessel wall 53 onto the portions of the teeth 115 that extend above a proximal surface 105 of the anvil 104 to provide a secure capture of the vessel wall 53.

Figure 28:
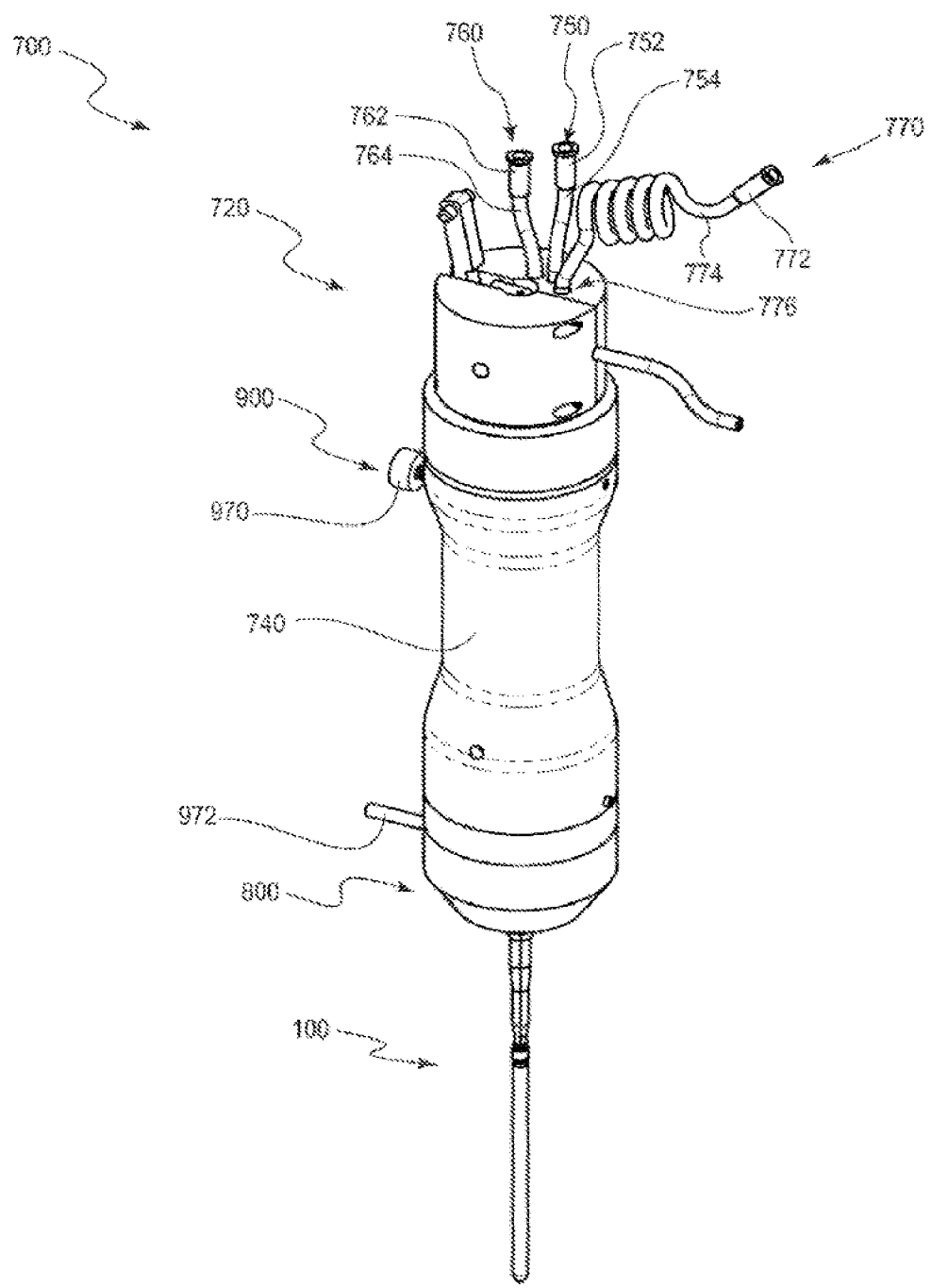
FIG. 28 is a perspective view of an embodiment of an vascular access implantation device.
Figure 29:
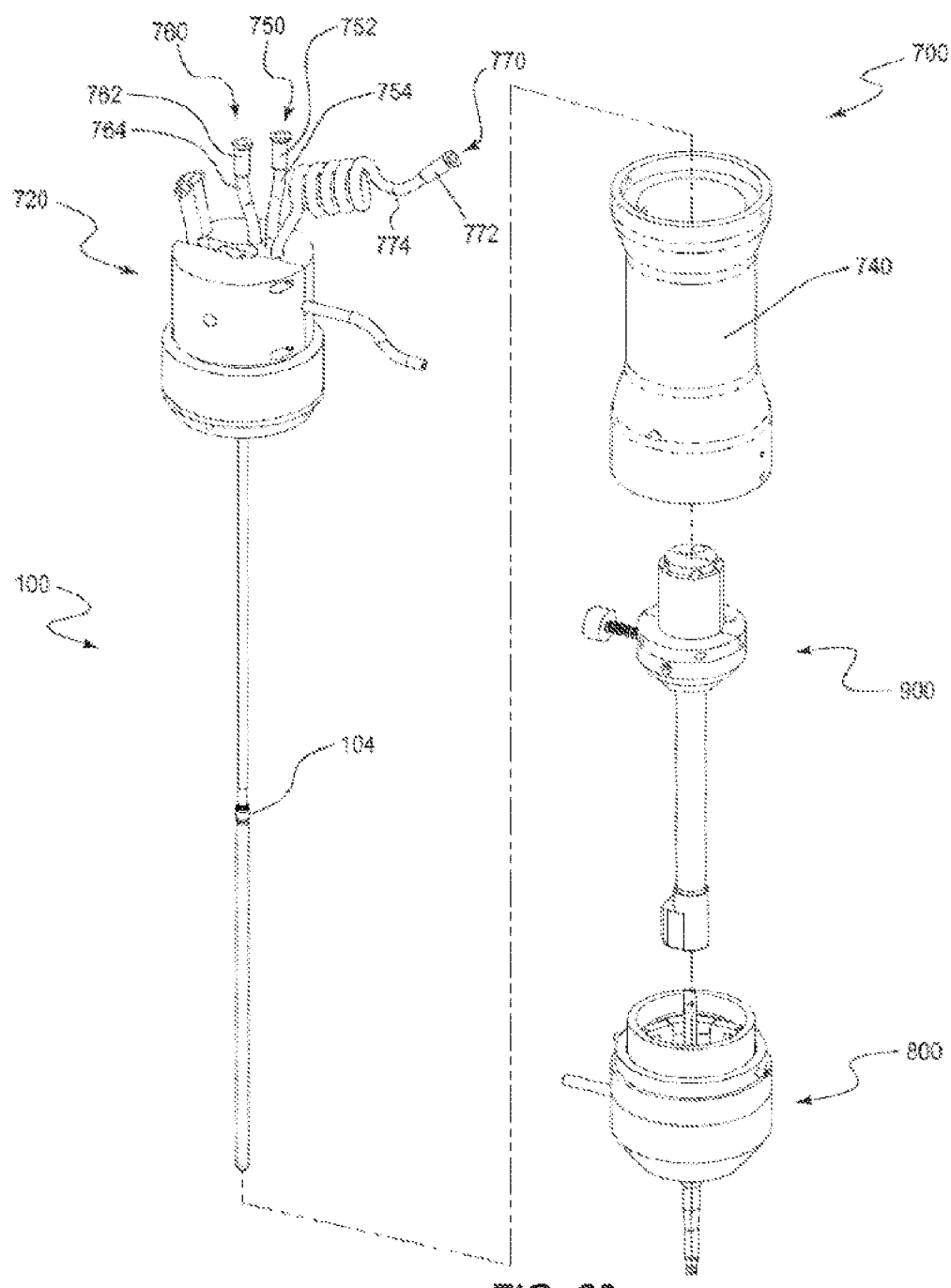
FIG. 29 is an exploded perspective view of the vascular access implantation device of FIG. 28.

FIGS. 28 and 29 illustrate an embodiment of a vascular access implantation device 700, which can be configured for implanting a vascular access port within a patient. The implantation device 700 can be configured to manage tissue during an anastomosis procedure and likewise to form the anastomosis itself. The implantation device 700 is described hereafter with respect to the implantation of a subcutaneous access port. However, other embodiments can be suitable for implantation of percutaneous devices, such as the conduit 318 and conduit adapter 304 described above. Accordingly, the specific examples provided hereafter should not be construed to limit the disclosure.

The implantation device 700 can include a clamp actuation device 720, which can resemble the clamp actuation device 120 discussed above in many respects, and thus like features are identified with like reference numerals with a leading hundreds numeral incremented to the value "7." The implantation device 700 can further include a tract dilator 800, which can resemble the tract dilator 200 discussed above in many respects, and thus like features are identified with like reference numerals with a leading hundreds numeral incremented to the value "8." The implantation device 700 can further include an approximation assembly or anastomosis actuation device 900, which can resemble the anastomosis actuation device 300 discussed above in many respects, and thus like features are identified with like reference numerals with a leading hundreds numeral incremented to the value "9." Therefore, the foregoing discussion regarding similarly numbered features is equally applicable hereafter and, accordingly, might not be repeated. For example, method steps or procedural stages for preparing an anastomosis site and performing an anastomosis described above, although not explicitly recited hereafter, may be performed via the implantation device 700. It is further noted that any suitable combination of the features described with respect to one or more of the clamp actuation device 120, the tract dilator 200, and the anastomosis actuation device 300 can be employed with the clamp actuation device 720, the tract dilator 800, and the anastomosis actuation device 900, respectively. The converse is also true.

The implantation device 700 can further include the clamp assembly 100. Numerous embodiments of the clamp assembly 100 are described above, and any suitable embodiment may be used with the implantation device 700. Likewise, any variations of the clamp assembly 100 that may be noted hereafter can be used in the embodiments described above. Accordingly, the foregoing discussion regarding the clamp assembly 100 is equally applicable hereafter and might not be repeated.

Embodiments of the implantation device 700 can differ from certain of the previously discussed embodiments in other respects. For example, in the illustrated embodiment, the clamp actuation device 720, the tract dilator 800, and the anastomosis actuation device 900 are assembled as a single unit so as to be able to function substantially without disassembly of the implantation device 700. Stated otherwise, each of the clamp actuation device 720 and the anastomosis actuation device 900 can be simultaneously physically connected to the tract dilator 800, whether the physical connection is direct or indirect.

Moreover, in the illustrated embodiment, the functionalities of each of the dilation actuator 220, the cutter actuator 320, and the approximation actuator 330 discussed above can be achieved via pressurized fluids. In other embodiments of the implantation device 700, pressurized fluids may be used for only one or only two of the foregoing actuator functionalities, or may be used for other (and/or additional) functionalities. As discussed in greater detail below, the implantation device 700 can include a dilation pressure port 750, a cutter pressure port 760, and/or an approximation pressure port 770 via which the actuator functionalities may be controlled. Each of the ports 750, 760, 770 can include a connector 752, 762, 772, respectively, which can be configured to couple with a pressurizing device, and each connector 752, 762, 772 can be in fluid communication with a separate fluid line or tube 754, 764, 774, respectively, that can deliver fluid to a specific region of the implantation device 700. The distal ends of the tubes 754, 764, 774 are not shown in FIGS. 28 and 29, but they are discussed hereafter.

In the illustrated embodiment, one or more of the connectors 752, 762, 772 comprise one or more of a luer connector that is configured to couple with an inflation syringe and/or a stopcock that is configured to selectively release or maintain a pressure provided to the ports 750, 760, 770. Suitable varieties of inflation syringes that can be used to pressurize portions of the implantation device 700 are known in the art, including inflation syringes that are generally used in angioplasty procedures.

With continued reference to FIGS. 28 and 29, the implantation device 700 can include a primary housing 740. In the illustrated embodiment, the primary housing 740 is connected to and/or interacts with each of the clamp actuation device 720, the tract dilator 800, and the anastomosis actuation device 900. Specifically, the clamp actuation device 720 is fixedly attached to a proximal end of the primary housing 740, the anastomosis actuation device 900 is received within and is selectively movable relative to the primary housing 740, and the tract dilator is fixedly attached to a distal end of the primary housing 740. The fixed connections between the clamp actuation device 720 and the primary housing 740 and between the tract dilator 800 and the primary housing 740 can be of any suitable variety, including, for example, hardware connections (e.g., nuts, bolts, screws, pins, etc.), adhesive bonds, and/or ultrasonic welds. The connection and the interaction between the anastomosis actuation device 900 and the primary housing 740 are discussed further below.

Figure 30:
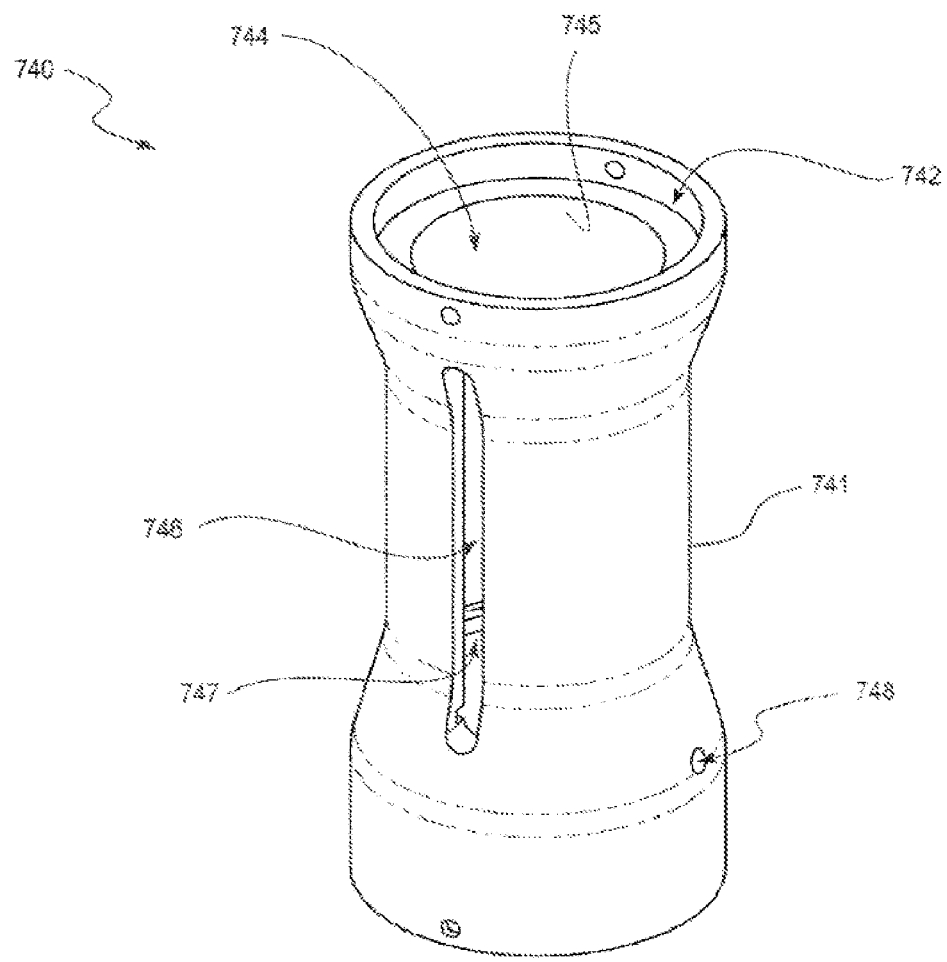
FIG. 30 is a perspective view of an embodiment of a primary housing.
Figure 31:
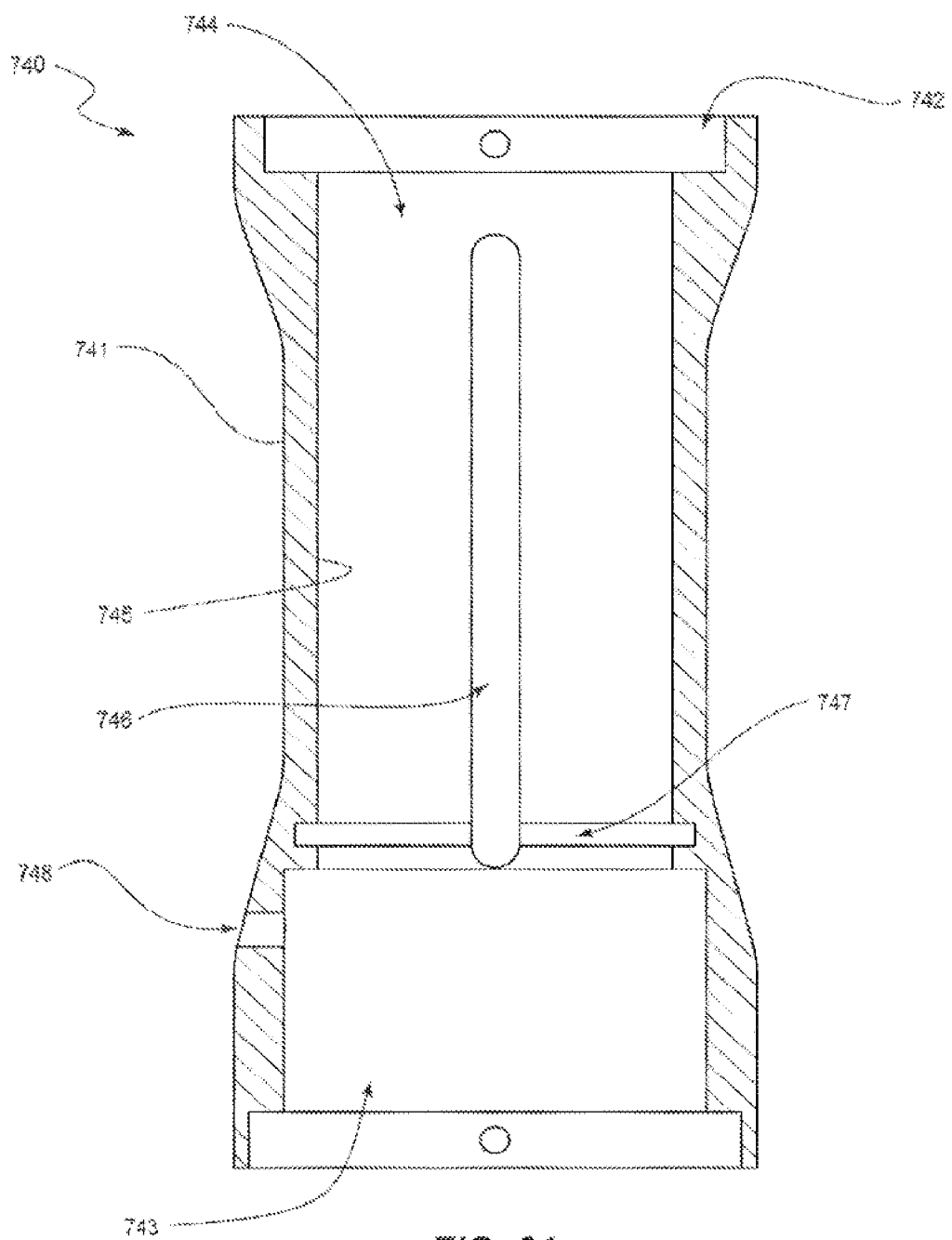
FIG. 31 is a cross-sectional view of the primary housing of FIG. 30.

With reference to FIGS. 30 and 31, in certain embodiments, the primary housing 740 can be sized, shaped, or otherwise configured to function substantially as a handle. For example, in the illustrated embodiment, the primary housing 740 is shaped substantially as a hollow cylinder open at both ends, and can be generally circular in cross-section. Other cross-sectional configurations are also possible, including generally elliptical, generally rectangular, etc. A longitudinal contour of an exterior surface 741 of the primary housing 740 can be generally shaped as an hourglass or dumbbell, such that the proximal and distal ends define larger outer diameters than does a central region.

The proximal end of the primary housing 740 can define a recess 742 configured to receive a distal portion of the clamp actuation device 720. Similarly, the distal end of the primary housing 740 can define a recess 743 configured to receive a proximal portion of the tract dilator 800. In the illustrated embodiment, the distal recess 743 is stepped, and is somewhat larger than the proximal recess 742.

An insertion channel 744 can extend between the proximal and distal recesses 742, 743. As further discussed below, the insertion channel 744 can be configured to permit the anastomosis actuation device 900, or a proximal portion thereof, to slide or otherwise translate therein. The insertion channel 744 can be defined by an interior surface 745 of the primary housing 740, which, in the illustrated embodiment, substantially defines a cylinder.

The primary housing 740 can define a slot 746, which can extend almost the full length or a substantial portion of the insertion channel 744. In the illustrated embodiment, the slot 746 is substantially parallel to a longitudinal axis of the primary housing 740. The slot 746 can fully extend through a sidewall of the primary housing 740 (e.g., through both the interior surface 745 and the exterior surface 741). One or more locking recesses 747 can be formed at or near a distal end of the slot 746. In the illustrated embodiment, a single locking recess 747 extends transversely about a periphery (e.g., about the circumference) of the inner surface 745 that defines the insertion channel 744. As further discussed below, the locking recess 747 can be used to secure the anastomosis actuation device 900 in an extended position.

In some embodiments, the primary housing 740 can define a viewing window 748, which can aid in detecting a position of the tract dilator 800, as further discussed below. The viewing window 748 can extend through a wall of the housing near a proximal end of the distal recess 743. The primary housing 740 can be formed from any suitable material, such as, for example, metal or plastic material, utilizing any suitable manufacturing technique, such as, for example, machining or injection molding.

Figure 32:
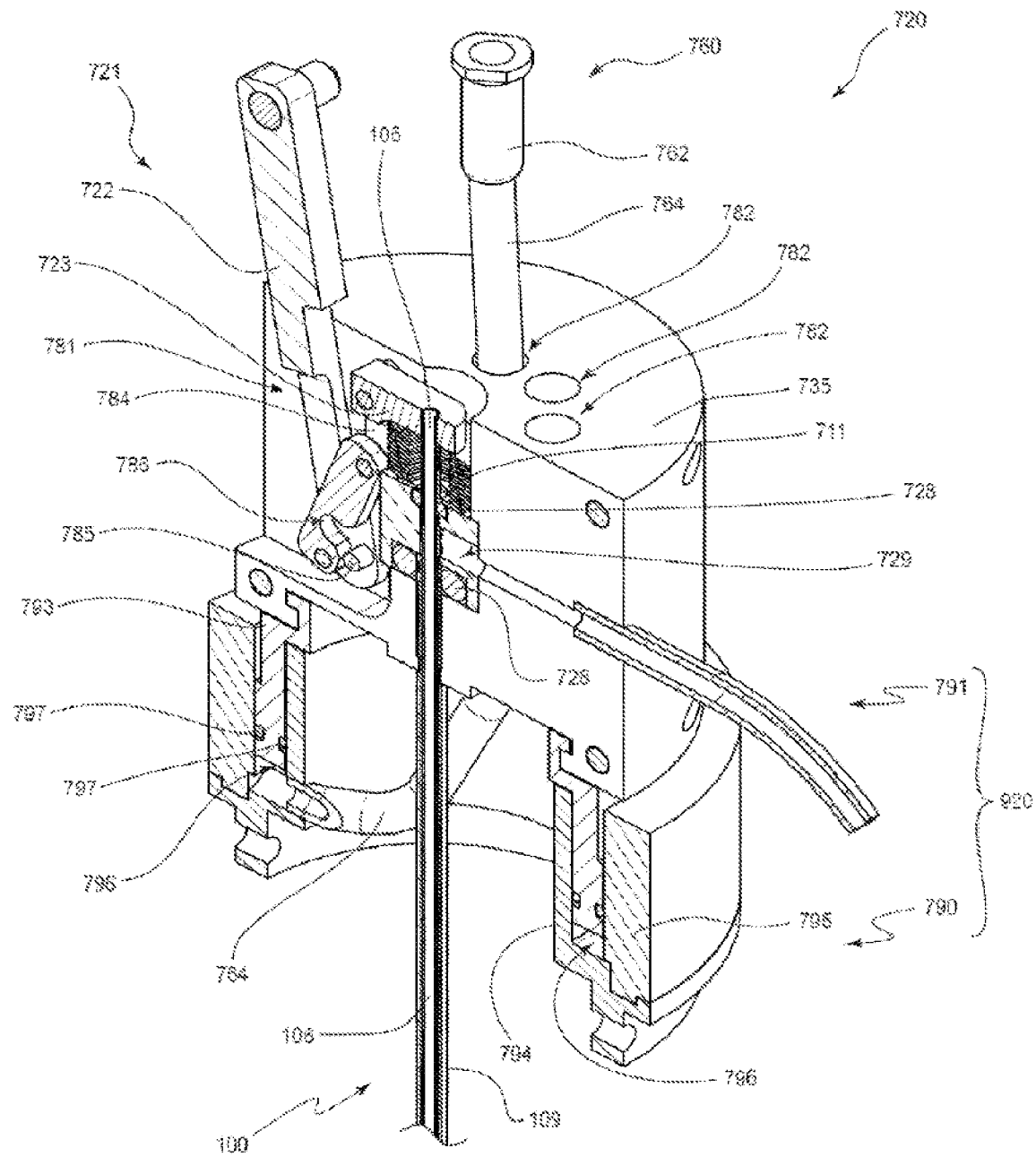
FIG. 32 is a perspective view of an embodiment of a clamp actuation device in a closed state.

With reference to FIG. 32, the clamp actuation device 720 can include a housing 735. In some embodiments, the housing 735 comprises two portions having a clam shell configuration. The portions of the housing 735 can be secured together in any suitable manner, such as with fasteners (e.g., bolts, nuts, screws, etc.), a snap fit, ultrasonic welding, etc. A first of the two portions is shown in FIG. 32, and the second can be seen in FIGS. 28 and 29. As with other housings described above and hereafter, the housing 735 can comprise any suitable material, such as a medical grade plastic or metal, and can be formed via any suitable manufacturing method, such as by machining or injection molding.

The housing 735 can define a recess 781 to accommodate movement of a clamp actuator 721, which is discussed further below. Additionally, in some embodiments, the housing 735 can define one or more channels 782 through which one or more of the tubes 754, 764, 774 can pass. For clarity, only tube 764 is shown in FIG. 32. The clamp tube 109 of the clamp assembly 100 can be fixedly attached to the housing 735.

As with the clamp actuation device 120, the clamp actuation device 720 can allow for withdrawal of blood and/or air from the vicinity of an anastomosis site via the clamp assembly 100 in order to determine a position of the distal portions of the clamp assembly 100. The clamp actuation device 120 can include a bodily fluid marker chamber 729 that is in fluid communication with a tube 74 and with the channel 113 between the clamp tube 109 and the anvil pull tube 106 (see FIG. 32). The clamp actuation device 120 can further include sealing devices 728 (e.g., o-rings) at either side of the bodily fluid marker chamber 729 to prevent leakage of blood or air. In the illustrated embodiment, the bodily fluid marker chamber 729 includes a channel that is positioned at the interface of the two joined portions of the housing 735. In other embodiments, the channel comprises a bore through a single portion of the housing 735, which can aid in preventing leakage of blood or air from the channel through the interface.

Figure 33:
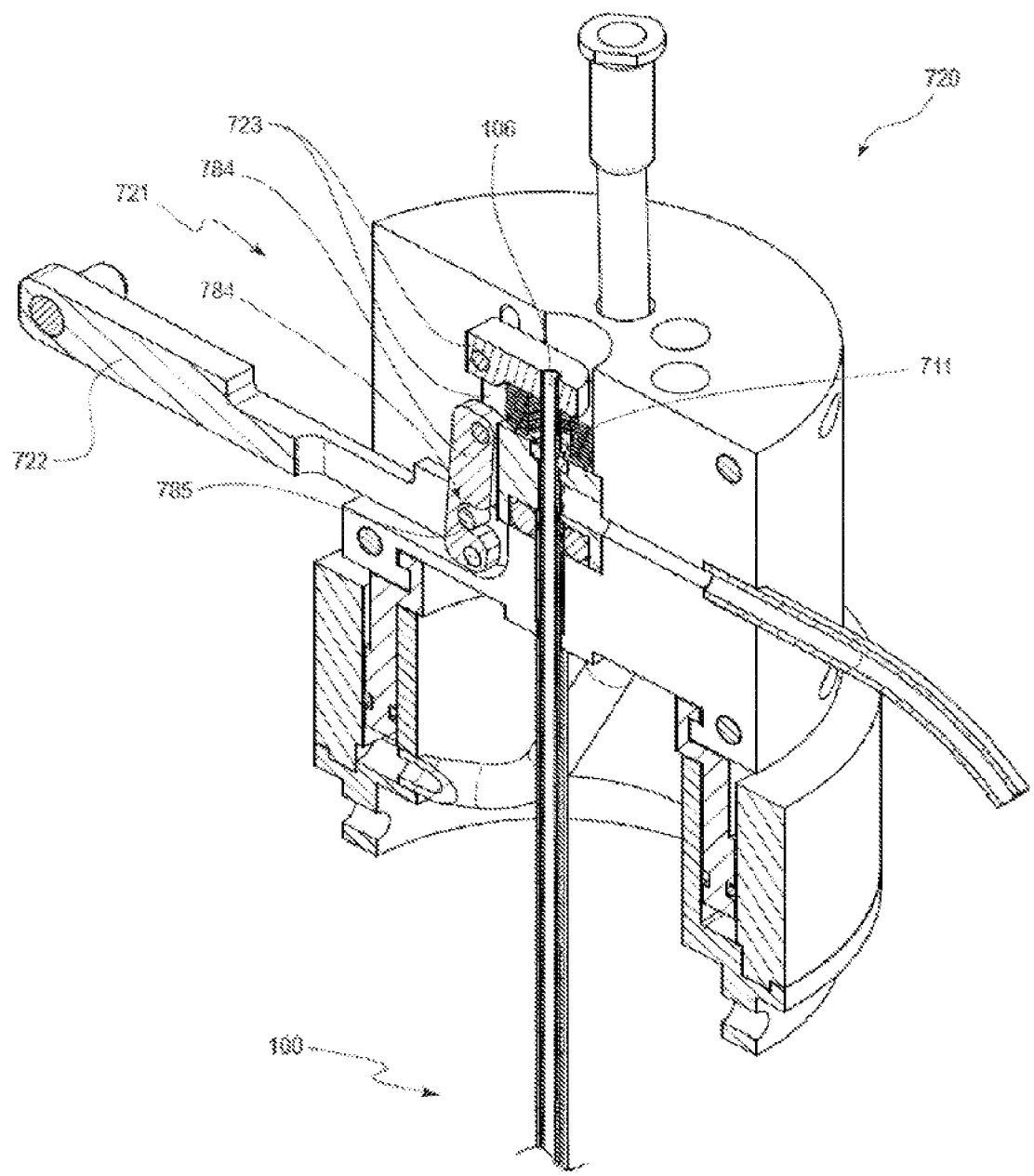
FIG. 33 is a perspective view of the clamp actuation device of FIG. 32 in an open state.
Figure 34:
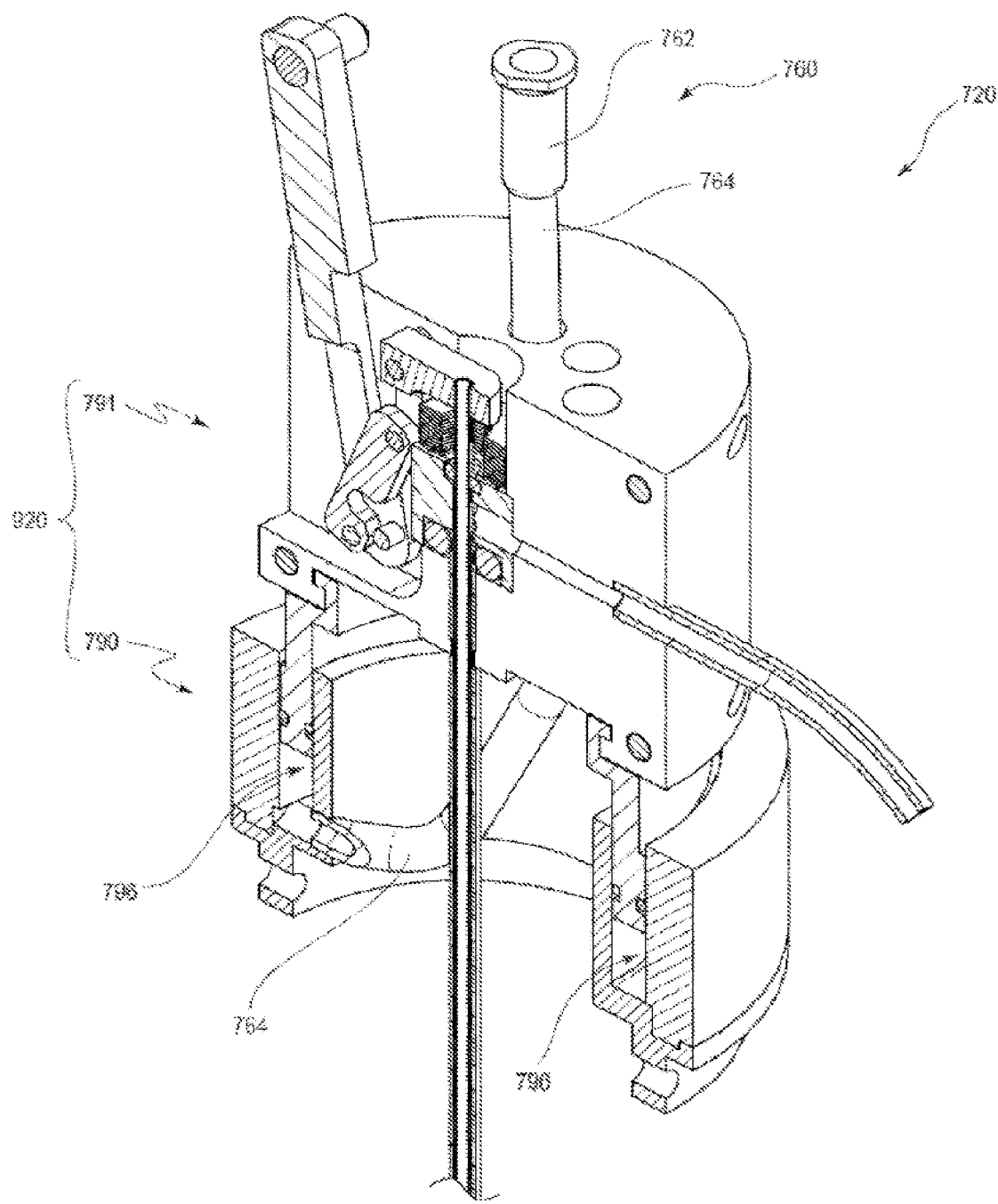
FIG. 34 is a perspective view of the clamp actuation device of FIG. 32 in the closed state and displaced as a cutting piston.

With reference to FIGS. 32 and 33, the clamp actuator 721 can include an outer arm 722 and an inner arm 723 that are pivotally coupled to each other via a linking arm 784. The inner arm 723 can be substantially L-shaped, with a first section extending in a direction substantially parallel to a longitudinal axis of the clamp actuator 721 and a second section extending substantially transverse thereto. In the illustrated embodiment, the transverse section of the inner arm 723 is fixedly attached to a proximal end of the anvil pull tube 106. The transverse section of the inner arm 723 can also contact a biasing member 711, which can provide a proximally directed longitudinal biasing force to the inner arm 723. The biasing force thus can bias the clamp actuator 721 to the closed orientation shown in FIG. 32. The biasing member 711 can comprise any suitable biasing device, such as a compression spring or one or more Bellville washers.

The clamp actuator 721 can be moved between closed orientation (FIG. 32) and the open orientation (FIG. 33), which can move the clamp assembly 100 between the closed orientation and the open orientation (as discussed above), respectively. In the illustrated embodiment, the clamp actuator 721 can be moved to the open state by rotating the outer arm 722 toward a distal end of the clamp actuation device 720. The outer arm 722 can be substantially perpendicular to a longitudinal axis of the actuation device 720 when in the open state. The clamp actuator 721 can be in the closed state when the outer arm 722 is rotated toward a proximal end of the clamp actuation device 720 so as to be substantially parallel to the longitudinal axis of the clamp actuation device 720.

In the illustrated embodiment, the outer arm 722 includes a pin 785 and the linking arm 784 includes a slot 786. As shown in FIG. 33, when the outer arm 722 is moved to the open orientation, the pin 785 can be received in the slot 786. In some embodiments, the pin-and-slot arrangement can provide for a compact actuator 721. In other or further embodiments, the slot 786 can interact with the pin 785 to maintain the actuator 721 in the open orientation. For example, in some embodiments, the slot 786 can frictionally engage the pin 785, or snap over the pin 785, so as to overcome the biasing force of the biasing element 711. A user than can selectively maintain the actuator 721 in the open orientation, which in some cases can facilitate manipulation of clamp assembly 100 to capture the vessel wall 53 (see FIG. 5). Other methods for selectively locking or maintaining the clamp actuator 721 in the open orientation are also possible.

With reference to FIG. 32, the clamp actuation device 720 can be coupled with a base 790 and can function as a cutter piston 791. In the illustrated embodiment, the clamp actuation device 720 is coupled with a plunger 793 that extends distally. The plunger 793 can be substantially cylindrical. The base 790 can include an inner wall 794 and an outer wall 795. In the illustrated embodiment, the inner and outer walls 794, 795 are formed of separate pieces, but they can be formed of a unitary piece in other embodiments. The inner and outer walls 794, 795 cooperate to define a pressure channel 796. In the illustrated embodiment, the pressure channel 796 is substantially cylindrical, and is closed at its distal end by a distal wall of the base 790.

The tube 764 can be coupled with the pressure channel 796 so as to provide fluid communication between the connector 764 and the pressure channel 796. For example, in the illustrated embodiment, the tube 764 can extend through one of the channels 782 through the housing 735, and a distal end of the tube 764 can extend through the inner wall 794 of the base so as to provide fluid communication between the connector 762 and the pressure channel 796. In other embodiments, the tube 794 can extend through the outer wall 795, and in further embodiments, the tube 794 can merely be coupled with the base 790 in a fluid-tight engagement without extending through the inner or outer walls 794, 795.

A proximal end of the pressure channel 796 can be sealed by the plunger 793. For example, in the illustrated embodiment, the cylindrical plunger 793 fits snugly within the cylindrical pressure channel 796. Sealing members 797, such as o-rings, can be positioned between the plunger 793 and each of the inner and outer walls 794, 795 to seal the upper end of the pressure channel 796. In the illustrated embodiment, an upper or proximal end of the plunger 793 has a reduced diameter, and a distal surface of the reduced-diameter portion interferes with an upper end of the inner wall 794 to prevent the plunger 793 from completely filling the pressure channel 796 and/or from blocking a fluid path at the distal end of the tube 764.

The cutter piston 791 and the base 790 can cooperate to effect cutting of a vessel wall 53, and thus together can be considered as a cutter actuator 920, such as the cutter actuator 320. For example, as previously discussed, the anvil pull tube 106 is fixedly attached to the inner arm 723 of the clamp actuation device 720 such that proximal movement of the cutter piston 791 effects proximal movement of the anvil pull tube 106. The implantation device 700 can include a cutter tube 909 (see FIG. 36), and sufficient proximal movement of the anvil pull tube 106 can bring the anvil 104 (see FIGS. 28 and 29) into contact with a blade 910 of the cutter tube 909 in a manner similar to that describe above with respect to the anastomosis actuation device 300.

The cutter piston 791 can be caused to move proximally relative to the base 790 by introduction of pressurized fluid into the pressure channel 796. In the illustrated embodiment, a inflation syringe (not shown) can be coupled with the connector 762 and pressurized fluid can be delivered to the pressure channel 796 via the tube 764. The pressurized fluid can apply pressure to a distal end of the plunger 793, thereby causing the cutter piston 791 to move proximally. In various embodiments, the pressure of the fluid within the pressure channel 796 at which cutting of the vessel wall 53 takes place and/or at which the blade 910 embeds within the anvil 104 is from about 2 atmospheres to about 6 atmospheres, no less than about 2 atmospheres, no less than about 3 atmospheres, no less than about 4 atmospheres, no less than about 5 atmospheres, or no less than about 6 atmospheres.

In some embodiments, once the cutting has taken place, the elevated pressure within the pressure channel 796 can be maintained. For example, a stopcock (not shown) can be adjusted to seal the pressurized fluid within the pressure channel 796, or the inflation syringe can remain coupled with the connector 762. Maintaining the pressure within the pressure channel 796 can have a similar effect to locking the cutter actuator 320 in the actuated orientation. As previously discussed, in some embodiments, it can be desirable to maintain the anvil 104 and the cutter tube 309 (or, in the present case, the cutter tube 909) in contact throughout final stages of an anastomosis procedure, such that a cut portion 334 of the vessel wall 53 is maintained between the clamp assembly 100 and the cutter tube 309 (or 909).

Figure 35:
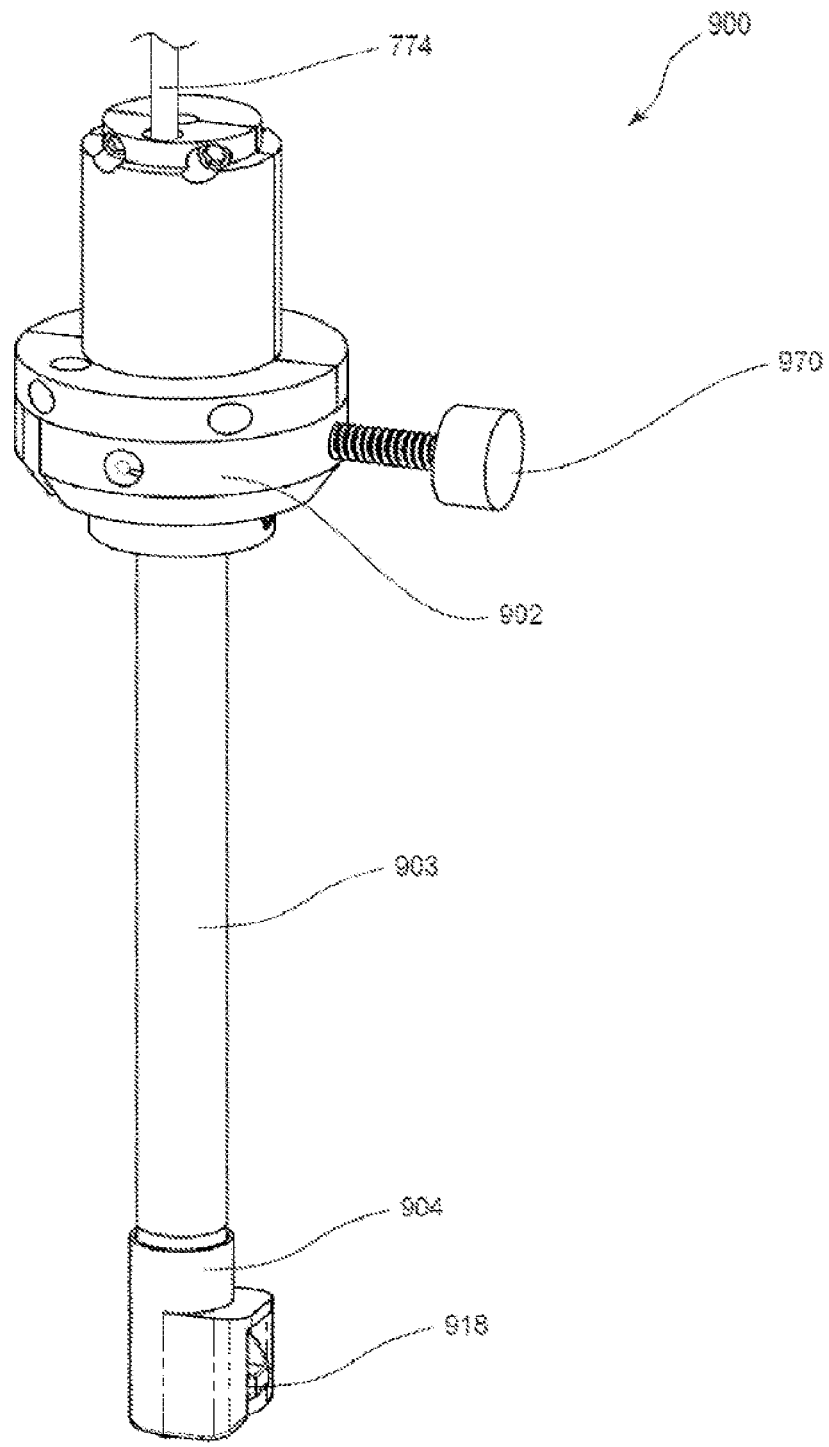
FIG. 35 is a perspective view of an embodiment of an anastomosis actuation device.
Figure 36:
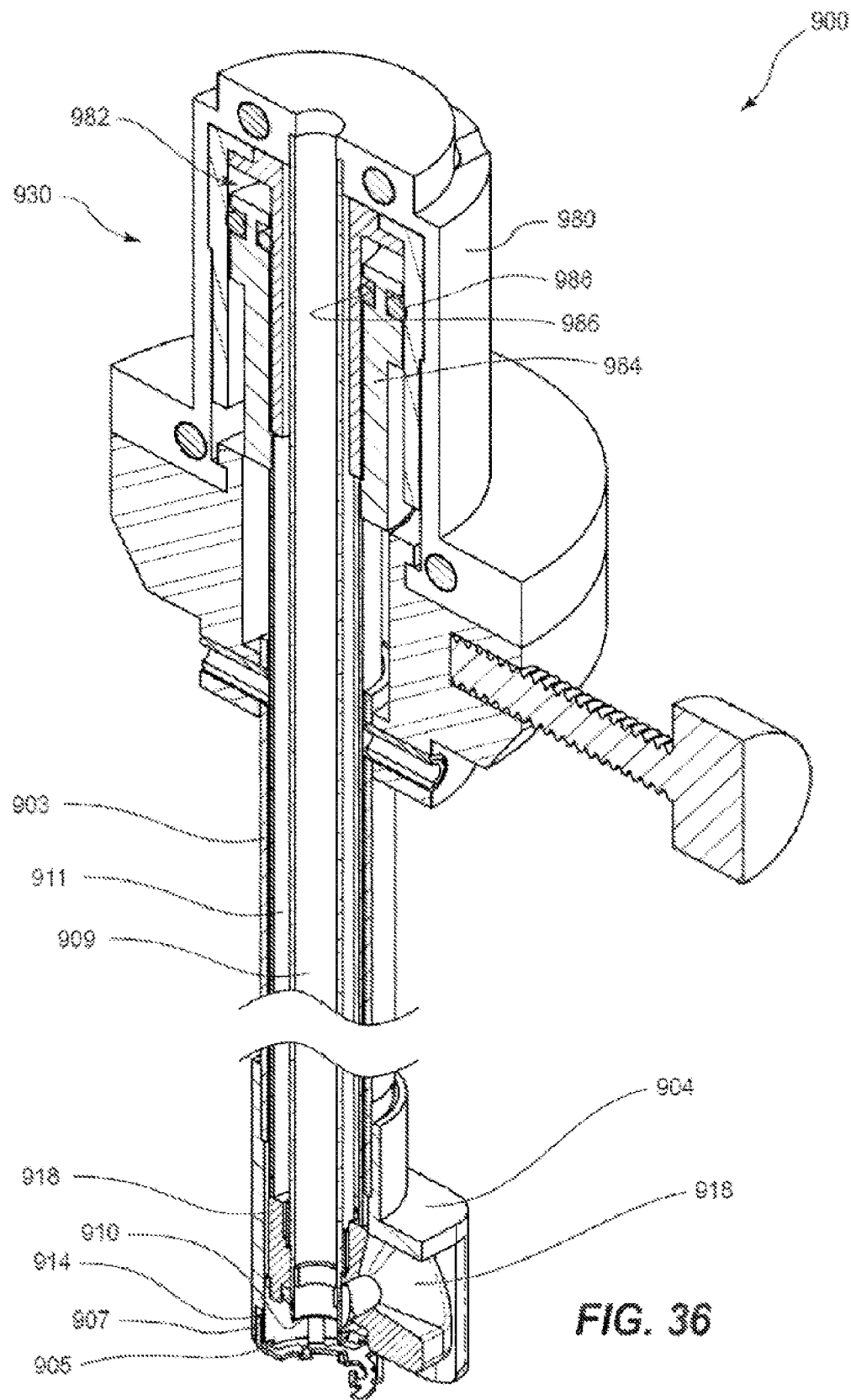
FIG. 36 is a cross-sectional view of the anastomosis actuation device of FIG. 35.

FIGS. 35 and 36 illustrate an embodiment of the anastomosis actuation device 900. Much of the anastomosis actuation device 900 can be the same as or similar to the anastomosis actuation device 300 discussed above. For example, the anastomosis actuation device 900 can include a lower housing 902, an adapter tube 903 fixedly attached to the lower housing 902 at a proximal end thereof and connected to a retaining adapter 904 at a distal end thereof, an anastomosis implant 918 temporarily attached to the retaining adapter 904, an actuator tube 911 inside the adapter tube 903, and a cutter tube 909 inside the actuator tube 911.

The anastomosis actuation device 900 can be telescopically positioned over the clamp tube 109 and within the primary housing 740, and can be slidable or translatable from an initial, retracted position to an actuated, extended position. In certain embodiments, the lower housing 902 can include an extension actuator 970, such as a pin or a knob, that can extend radially outward from the lower housing 902. As partially shown in FIG. 28, the extension actuator 970 can extend through the longitudinal slot 746 of the primary housing 740. The extension actuator 970 can function as a handle or grip to facilitate movement of the anastomosis actuation device 900 from the retracted position to the extended position. In some embodiments, a protrusion 972 can extend from the implantation device 700 at a position distal of the extension actuator 970, such as from a side of the tract dilator 800. The protrusion 972 can aid in the deployment of the anastomosis actuation device 900 from the retracted position to the extended position, as both protrusion 972 and the extension actuator 970 can be held simultaneously and squeezed toward each other.

When moved to the extended position, the anastomosis actuation device 900 can lock into place to prevent inadvertent retraction of the anastomosis actuation device 900. The locking can be achieved by one or more spring pins that extend radially outwardly from the lower housing 902 being released outwardly into the one or more locking recesses 747. The spring pin can be compressed by the primary housing 740 when the anastomosis actuation device 900 is in its initial retracted position, as well as during translation of the anastomosis actuation device 900 toward the extended position, and can be released to its biased state upon reaching the one or more locking recesses 747.

The retaining adapter 904 can be similar to the retaining adapter 304. For example, the retaining adapter 904 can include one or more retention channels 914 that are configured to interface with one or more retention legs 907 of an anastomosis clip 905. However, in some embodiments, the retaining adapter 904 can exhibit certain differences. For example, in the illustrated embodiment, the retaining adapter 904 is shaped to accommodate the positioning of an anastomosis implant 918 therein. The illustrated embodiment of the retaining adapter 904 is radially nonsymmetrical to accommodate an anastomosis implant 918 that has an access port 980 at one side thereof (see also FIG. 40).

Although the anastomosis implant 918 can be different from the conduit 318, as further discussed below, the anastomosis implant 918 can include an anastomosis adapter 913 (FIG. 40) that is similar to the conduit adapter 313. The anastomosis implant 918 can be attached to the anastomosis adapter 913 or can be integrally formed therewith such that the anastomosis adapter 913 and the anastomosis implant 918 form a unitary structure. The anastomosis adapter 913 can include connection channels configured to interface with connection legs of the clip 905 in the same manner that the connection channels 313 interface with the connection legs 308 of the clip 305.

The anastomosis procedures described above with respect to the conduit 318 and the conduit adapter 313 can be substantially the same as those by which the anastomosis implant 918 is connected to a vessel. However, in the illustrated embodiment, an approximation actuator 930 takes the place of the approximation actuator 330. With reference to FIG. 36, the approximation actuator 930 can comprise an upper housing 980 that defines an annular pressure channel 982 and a plunger 984. The upper housing 980 can be comprised of one or multiple pieces. The plunger 984 can be positioned in the pressure channel 982, and may include a separate sealing member 986, such as an o-ring, at each of an inner and an outer interface with the upper housing 980. The plunger 984 thus can have a fluid-tight seal with the upper housing 980 so as to close a distal end of the pressure channel 982. The cutter tube 909 may be fixedly attached to the upper housing 980.

Figure 37:
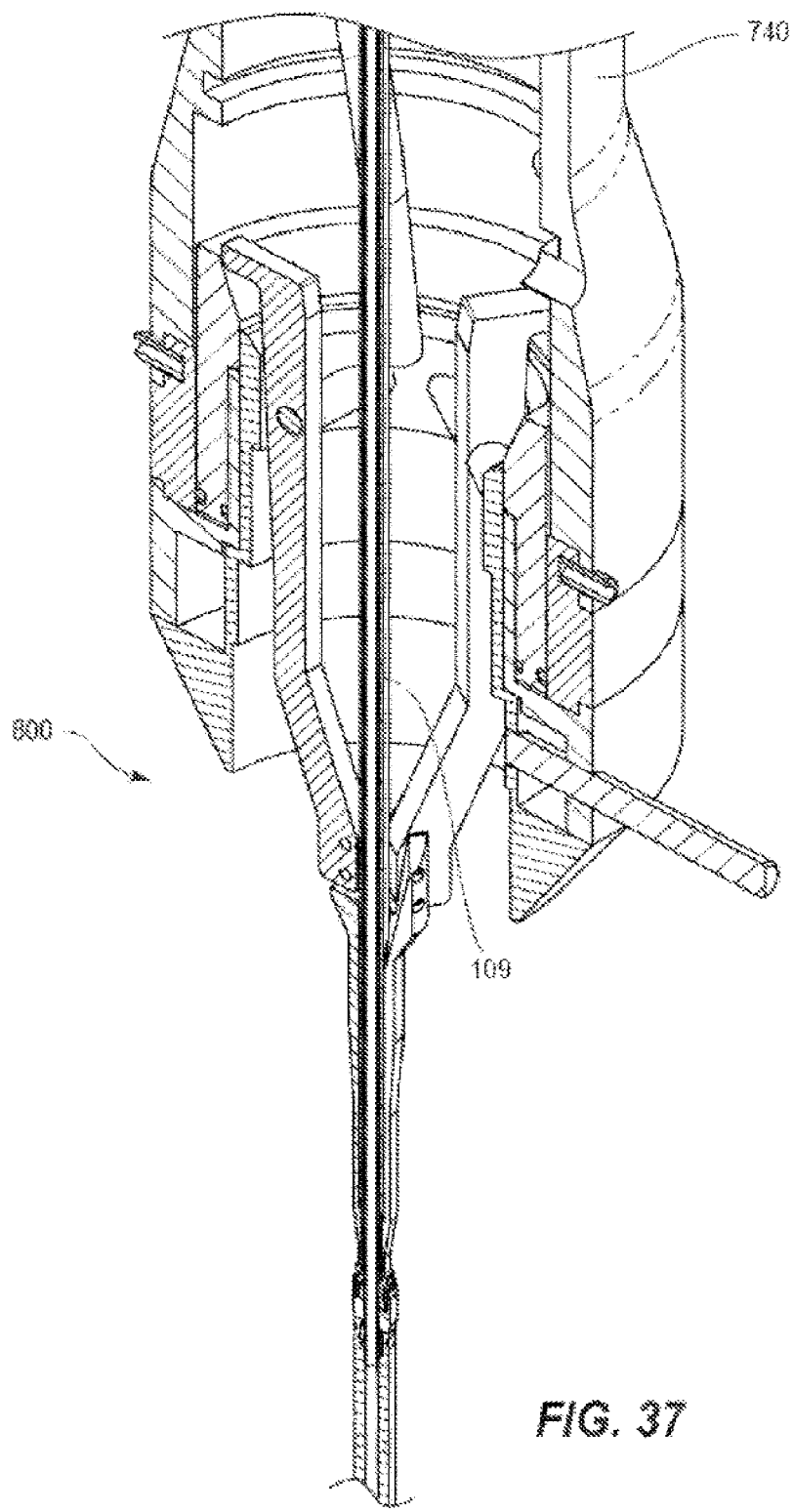
FIG. 37 is a cross-sectional view of another embodiment of a tract dilator in a pre-assembled state and a closed configuration.
Figure 38:
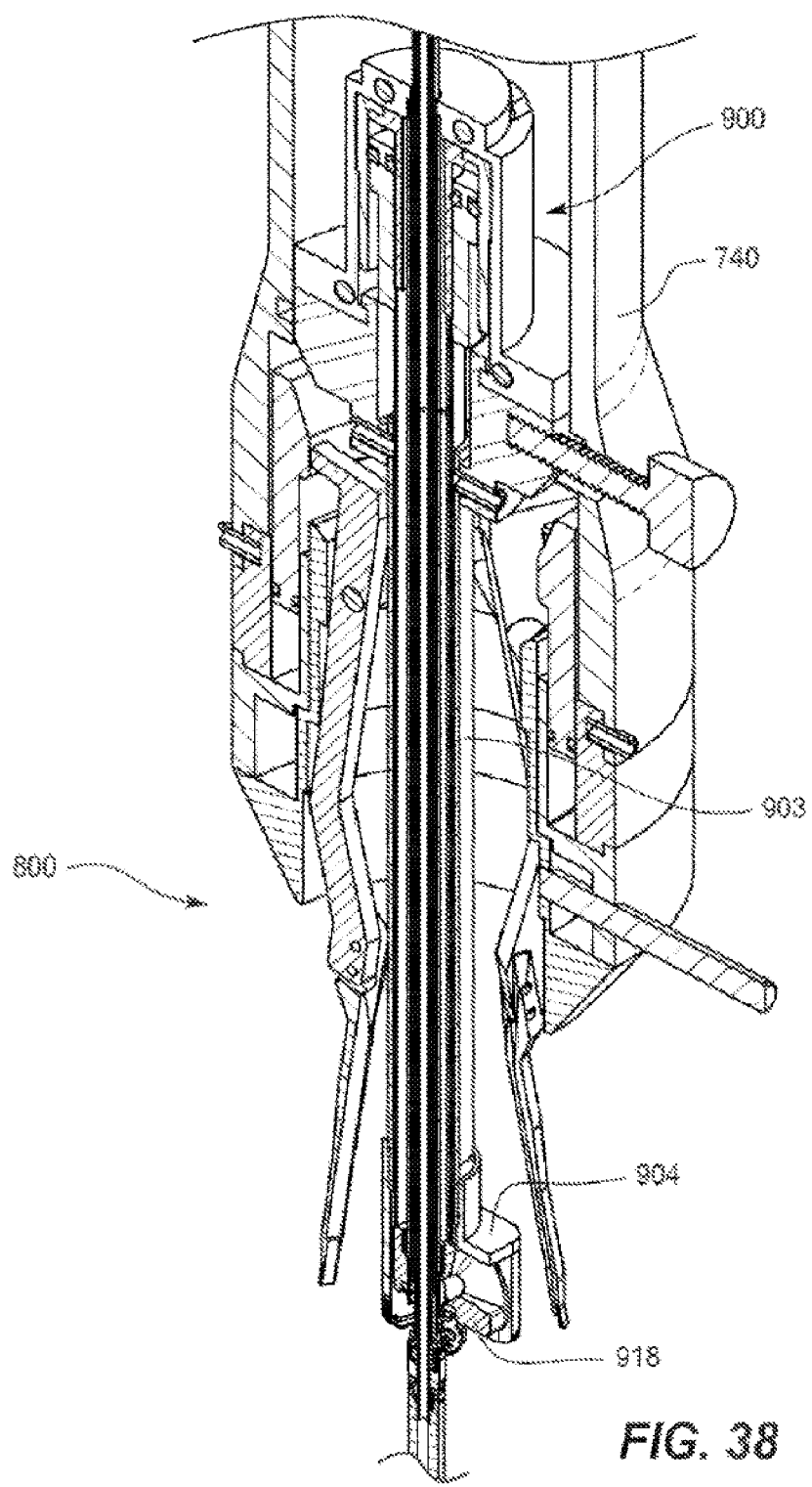
FIG. 38 is a cross-sectional view of the dilator of FIG. 37 in an assembled state and an open configuration.
Figure 39:
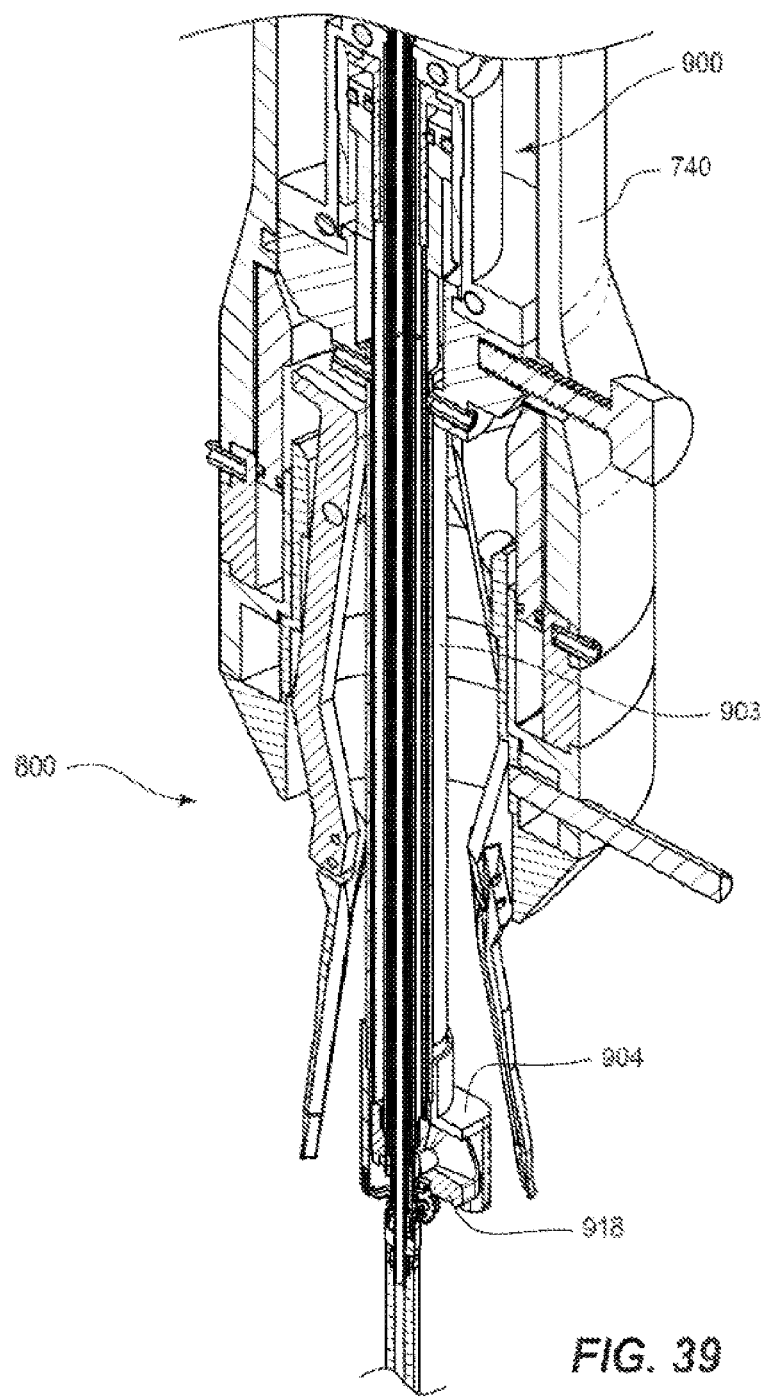
FIG. 39 is a cross-sectional view of the dilator of FIG. 37 in an assembled state and in a retraction configuration.

Referring to FIGS. 37-39, an embodiment of a tract dilation assembly (or tract dilator) 800 is shown. The tract dilation assembly can include a dilator handle, a dilator pressure port and one or more dilator legs. The tract dilation assembly 800 proximal end can engage the tool housing 740 distal end. The tract dilation assembly 800 can be telescopically positioned over the clamp tube 109 with the clamp tube 109 extending beyond the proximal and distal ends of the tract dilation assembly 800. The distal portion of the approximation assembly 900 can extend into the tract dilation assembly 800 when the approximation assembly 900 is in its initial position. When the approximation assembly 900 is in its extended position, the approximation assembly 900 distal end can align with the tract dilation assembly 800 distal end.

The tract dilation handle can be generally cylindrical in shape with a bore passing through the handle. The tract dilation pressure port can engage the proximal end of the dilator handle. The pressure port can include a port body and a plunger. The port body can have an inner wall and an outer wall with an annular space between them. The annular space can be closed at its distal end and open at its proximal end. The plunger can be telescopically positioned at least partially within the annular space. O-rings near the distal end of the plunger facilitate a liquid seal of the annular space. A fluid channel through the port body inner wall or outer wall can provide fluid communication from outside the tract dilator to the annular space to facilitate pressurization of the annular space. The plunger proximal portion can extend proximally beyond the annular space. The proximal portion can have an inner surface that is tapered. The tapered surface can be a cam surface for interaction of the proximal end of the dilation leg.

The tract dilation assembly 800 can include three dilation legs. The legs can be pivotally secured to the interior of the dilation handle and extend distally beyond the dilation handle. The leg can be made integrally as a single component or can be made of two or more components, a dilation portion and a lever portion. The two components can be secured together using methods such as welding, screws, pins or other known methods. The leg can be made from a rigid material such as stainless steel. The leg dilation portion can be configured to closely surround the clamp tube. The leg dilation portion can be radiussed exteriorly and interiorly such that the leg conforms to the shape of the clamp tube. Each leg can cover approximately 120° of the clamp tube 109 circumference to form a nearly solid surface. The leg distal end can abut the clamp foot 110 flange. The diameter of the three legs at the distal end can be approximately equal to the diameter of the clamp foot 110 flange to facilitate a smooth insertion of the dilation legs through the tissue and vessel wall. The leg outside surface can be tapered just proximal to the leg distal end. The increased thickness of the leg at its mid and proximal portions can increase stiffness to prevent flexing of the leg during tract dilation.

The dilation leg lever portion can be configured to accommodate the approximation assembly adapter when the approximation assembly is in the retracted position. The leg lever portion proximal end can be configured to engage the plunger cam surface. A pivot pin near the lever portion proximal end can secure the leg to the tract dilator handle and function as a pivot point for the leg.

In use, the annular space of the tract dilator pressure port can be pressurized with a fluid through the fluid channel. The plunger can be forced by the pressurized fluid to move in a proximal direction. As the plunger moves proximally, the leg lever portion proximal end can engage the plunger cam surface. The leg lever proximal end can pivot inward around the pin and the leg dilation portion can move radially outward to dilate the tissue of the insertion tract. The dilated tract can be a triangular shape sized to accommodate the passage of the approximation adapter when the approximation assembly is moved to an extended position.

As previously mentioned, methods for using the implantation device 700 will be evident from the disclosure herein. Additional examples of such methods are now provided. In some instances, a method of anastomosing the anastomosis implant 918 to a vessel wall 53 can include passing the implantation device 700 over a guidewire 103 which has been positioned in the lumen 50 of a blood vessel 51 using known techniques. The guidewire 103 can pass through the tip 101, the anvil 104, into the anvil pull tube 106 and exit the proximal end of the anvil pull tube 106. The tip 101, the anvil 104 and the clamp foot 110 can be inserted through the subcutaneous tissue and through the vessel wall 53 into the lumen 50 of the blood vessel 51. The distal portion of the dilator legs can also be inserted into the vessel lumen 50. When the clamp foot is in the vessel lumen, blood can be drawn through the port 112 in the clamp foot 110 into the annular space between the anvil pull tube 106 and the clamp tube 109. The blood can flow into the bodily fluid marker channel in the clamp handle and exit into the lumen of the flexible tube attached to the external orifice of the channel. The blood can be visualized by the clinician and can confirm insertion of the anvil 104 and clamp foot 110 into the lumen 50 of the vessel 51.

The clamp lever can be moved from the clamp closed position to the clamp open position. Movement of the clamp lever can move the anvil pull tube 106 distally resulting in a separation of the anvil 104 and clamp foot 110 and the formation of a gap between the anvil 104 and clamp foot 110. Separation of the anvil 104 and clamp foot 110 can expose the projections 115 of the tissue capture tube 133. The guidewire 103 can be removed from the vessel 51 and the anastomosis tool 700. The anastomosis tool 700 can be moved proximally allowing the vessel wall 53 to slide over the clamp foot 110 flange and into the gap. As the vessel wall 53 passes into the gap, the dilated hole in the vessel wall 53 reduces in diameter due to the elasticity of the vessel wall tissue. The vessel wall 53 is caught by the projections 115 of the tissue capture tube 133. The clinician can sense a resistance to further proximal movement of the anastomosis tool 700 due to the capture of the vessel wall 53 by the tissue capture tube 133. Blood can stop flowing into the bodily fluid marker tube due to capture of the vessel wall 53 distal to the bodily fluid marker port 112 in the clamp foot 110. The stoppage of blood flow through the bodily fluid marker can confirm vessel wall capture in the gap between the anvil 104 and clamp foot 110 flange. The clamp lever can be moved to the clamp closed position. This can result in proximal movement of the anvil 104 and closing of the gap between the anvil 104 and clamp foot 110. The anvil pull tube 106 can be biased proximally by the springs in the clamp handle resulting in compression of the vessel wall tissue onto the projections 115 of the tissue capture tube 133.

The insertion tract surrounding the implant tool 700 can be dilated to facilitate positioning of the implant 918 adjacent to the vessel wall 53. The tract dilation pressure port can be pressurized. When the port is pressurized, the plunger can move proximally. The cam at the proximal end of the plunger can engage the dilation leg proximal end causing the leg proximal portions to pivot radially inward around the pivot pin. The dilator leg distal portion can pivot radially outward away from the clamp tube 109. As the legs move outward, tissue surrounding the legs can be moved away from the anastomosis tool 700. A tract dilator having three legs can form an expanded triangular shaped insertion tract 55 around the clamp tube 109 of the tool 700. A tract dilator having four legs can form a generally square or rectangular shaped insertion tract 55. The expanded tract 55 can be formed from the epidermis to the outer surface of the blood vessel wall 53. In some embodiments, all layers of skin, subcutaneous tissue and facia layers to the outer surface of the blood vessel 51 can be cleared from the insertion tract 55 surrounding the anastomosis tool 700.

The approximation assembly 900 can be moved distally from its retracted position to its extended position. The adapter 904 can pass between the dilator legs into the expanded insertion tract 55. The adapter 904 distal end and the implant 918 assembly can be positioned adjacent to the vessel wall 53. The approximation assembly 900 handle can be locked into the extended position relative to the tool housing 740.

An anastomosis opening can be cut in the vessel wall 53 by pressurizing the cutter pressure port with fluid causing the cutter plunger 793 and inner arm 723 of the clamp actuation device 720 to move proximally. Proximal movement of the inner arm 723 of the clamp actuation device 720 can result in proximal movement of the anvil pull tube 106. The anvil pull tube 106 can pull the anvil 104 and the captured vessel wall 53 into the implant 918. Continued movement of the cutter plunger 793 can pull the anvil 104 and the captured vessel wall 53 against the cutting blade 910 of the cutter tube 909. The blade 910 can cut through the vessel wall tissue and partially embed into the anvil 104 proximal end. The cut vessel wall 53 partially retracts distally along the anvil 104. The opening of the implant 918 can be sized to facilitate compression of the vessel wall 53 against the anvil 104. The compression of the vessel wall 104 prevents the vessel wall 104 from full retraction out of the implant 918.

The anastomosis of the implant 918 to the vessel wall 53 can be completed by approximating the implant 918 and clip 905. The approximation port can be pressurized with fluid. When pressurized, the approximation port plunger 984 can move distally. As the plunger 984 moves distally, the approximation tube 911 can engage the implant 918 and move the implant 918 distally. With continued movement, the implant 918 can engage the partially retracted vessel wall 53 and evert the vessel wall 53 over the clip 905. The everted vessel wall 53 can be compressed between the implant 918 and the clip 905.

Following approximation of the clip 905 and the implant 918, additional pressurization of the approximation pressure port increases the force applied to the implant 918 by the approximation tube 911. The increased force can result in ejection of the implant 918 from the implant tool 700. The implant tool 700 can then be removed from the insertion site.

The implant tool 700 can be provided to a clinician pre-assembled in a sterile package (not shown). Also, provided in the package can be ancillary medical devices to facilitate utilization of the implant tool 700. The ancillary medical devices can include a micropuncture set, a guidewire, dilators, syringes, needles and a scalpel. The implant tool 700 can be a onetime use medical device. In other embodiments, the implant tool 700 can be configured to be used for multiple vascular access port implantations.

What is claimed is:

1. A method of attaching an implant to a vessel, the method comprising:
   inserting through a wall of a vessel within a patient an implantation device having a clamp foot and an anvil apparatus that includes tissue capture teeth, the clamp foot and the anvil apparatus being positioned within the lumen of the vessel after inserting the implantation device;
   clamping a portion of the vessel wall between the clamp foot and the anvil apparatus such that the tissue capture teeth capture a portion of the vessel wall on its luminal side without extending completely through the vessel wall;
   positioning an implant adjacent to an outer surface of the wall of the vessel, the implant including an access port at one side of the implant and a lumen in fluid communication with the access port;

cutting the wall of the vessel about the portion of the wall that has been clamped via a cutting blade that is attached to a cutter tube of which a portion is positioned within the lumen of the implant and of which no portion is positioned within the access port of the implant;

passing the portion of the wall that has been clamped and that has been cut about through the lumen of the implant to remove the portion of the wall from the patient and to provide an opening in the vessel; and securing the implant to the vessel such that the access port is in direct fluid communication with an interior of the vessel via the lumen of the implant and the opening in the vessel.

2. The method of claim 1, wherein the access port of the implant is at an angle relative to the lumen of the implant.

3. The method of claim 1, wherein the clamping step includes drawing the captured portion of the vessel wall radially inward toward the clamp foot.

4. The method of claim 3, wherein the securing step includes approximating the implant to a clip such that the captured portion of the vessel wall is compressed between the implant and the clip.

5. The method of claim 1, wherein the implantation device further includes a tract dilator for dilating tissue surrounding the implantation device, and the tissue is dilated before the positioning step, thereby facilitating positioning of the implant adjacent to the outer surface of the wall of the vessel.

6. The method of claim 5, wherein the tract dilator includes at least two dilation legs and the tissue is dilated by pivoting the dilation legs radially outward from the implantation device.

7. The method of claim 6, wherein the tract dilator includes three or four dilation legs.

8. The method of claim 6, wherein a distal portion of the at least two dilator legs is inserted through the vessel wall prior to dilation of the tissue.

9. The method of claim 1, wherein the inserting step includes passing the implantation device over a guide wire that has been positioned in the lumen of the vessel.

10. The method of claim 1, wherein the clamping step includes:

separating the clamp foot from the anvil apparatus to create a gap therebetween, thereby exposing the tissue capture teeth;

moving the implantation device proximally until the clamp foot is outside of the vessel and the tissue capture teeth capture the portion of the vessel wall on its luminal side, the anvil apparatus remaining within the vessel lumen; and urging the clamp foot towards the anvil apparatus to close the gap.

\* \* \* \* \*